(12) United States Patent
Curran et al.

(10) Patent No.: US 8,870,960 B2
(45) Date of Patent: *Oct. 28, 2014

(54) TOTAL DISC REPLACEMENT SYSTEM AND RELATED METHODS

(71) Applicant: NuVasive, Inc., San Diego, CA (US)

(72) Inventors: Matthew Curran, Carlsbad, CA (US); Luiz Pimenta, Sao Paulo (BR); Scot Martinelli, Mountain Top, PA (US); G. Bryan Cornwall, San Diego, CA (US); Jonathan D. Spangler, Del Mar, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/711,561

(22) Filed: Dec. 11, 2012

(65) Prior Publication Data

US 2013/0289726 A1    Oct. 31, 2013

Related U.S. Application Data

(63) Continuation of application No. 11/989,686, filed as application No. PCT/US2006/029196 on Jul. 28, 2006, now Pat. No. 8,328,851.

(60) Provisional application No. 60/721,805, filed on Sep. 28, 2005, provisional application No. 60/703,645, filed on Jul. 28, 2005.

(51) Int. Cl.
  *A61B 17/88* (2006.01)
  *A61F 2/30* (2006.01)
  *A61F 2/46* (2006.01)
  *A61F 2/44* (2006.01)

(52) U.S. Cl.
  CPC ....... *A61F 2/442* (2013.01); *A61F 2002/30369* (2013.01); *A61F 2002/4629* (2013.01);

(Continued)

(58) Field of Classification Search
  USPC ....... 606/246, 279, 99, 102, 86 A; 623/17.11, 623/17.14, 17.15, 17.16
  See application file for complete search history.

(56) References Cited

U.S. PATENT DOCUMENTS

| 208,227 A | 9/1878 | Dorr |
| 972,983 A | 10/1910 | Arthur |

(Continued)

FOREIGN PATENT DOCUMENTS

| CA | 2015507 | 1/1999 |
| DE | 299 08 259 | 7/1999 |

(Continued)

OTHER PUBLICATIONS

Anatomy of the Lumbar Spine in MED TM MicroEndoscopic Discectomy (1997 Ludann Grand Rapids MI), 14 pgs.

(Continued)

*Primary Examiner* — Pedro Philogene
*Assistant Examiner* — David Comstock
(74) *Attorney, Agent, or Firm* — Jonathan Spangler; Rory Schermerhorn

(57) ABSTRACT

A total disc replacement (TDR) system for lateral insertion into the spine, involving a first anchor plate having a first surface for engaging a first vertebra and a second surface including a cutout region, a second anchor plate having a first surface for engaging a second vertebra and a second surface including a cutout region, at least one pair of intradiscal inserts, each insert having a first surface for engaging with said anchor plates and a second surface for engaging with an intradiscal element, and an intradiscal element including a first articular surface having a generally arcuate cross-section for articulating with said first intradiscal insert, and a second generally planar surface for interacting with a second intradiscal insert.

23 Claims, 36 Drawing Sheets

(52) U.S. Cl.
CPC ....... *A61F 2/4684* (2013.01); *A61F 2002/4627* (2013.01); *A61F 2002/30331* (2013.01); *A61F 2220/0033* (2013.01); *A61F 2002/4622* (2013.01); *A61F 2002/30649* (2013.01); *A61F 2002/4635* (2013.01); *A61F 2002/30601* (2013.01); *A61F 2310/00239* (2013.01); *A61F 2002/443* (2013.01); *A61F 2002/30841* (2013.01); *A61F 2002/30433* (2013.01); *A61F 2310/00011* (2013.01); *A61F 2002/305* (2013.01); *A61F 2220/0025* (2013.01); *A61F 2002/30364* (2013.01); *A61F 2310/00203* (2013.01); *A61F 2/4425* (2013.01); *A61F 2220/0041* (2013.01); *A61F 2002/30616* (2013.01); *A61F 2002/4628* (2013.01); *A61F 2/4611* (2013.01)
USPC ........................................ 623/17.11; 606/279

(56) References Cited

U.S. PATENT DOCUMENTS

| | | |
|---|---|---|
| 1,328,624 A | 1/1920 | Graham |
| 1,548,184 A | 8/1925 | Cameron |
| 2,704,064 A | 6/1955 | Fizzell et al. |
| 2,736,002 A | 2/1956 | Oriel |
| 2,808,826 A | 10/1957 | Reiner et al. |
| 3,364,929 A | 1/1968 | Ide et al. |
| 3,486,505 A | 12/1969 | Morrison |
| 3,518,993 A | 7/1970 | Blake |
| 3,604,487 A | 9/1971 | Gilbert |
| 3,664,329 A | 5/1972 | Naylor |
| 3,682,162 A | 8/1972 | Colyer |
| 3,745,995 A | 7/1973 | Kraus |
| 3,785,368 A | 1/1974 | McCarthy et al. |
| 3,830,226 A | 8/1974 | Staub et al. |
| 3,848,601 A | 11/1974 | Ma et al. |
| 3,867,728 A | 2/1975 | Stubstad et al. |
| 3,957,036 A | 5/1976 | Normann |
| 4,026,304 A | 5/1977 | Levy |
| 4,026,305 A | 5/1977 | Brownlee et al. |
| 4,099,519 A | 7/1978 | Warren |
| 4,164,214 A | 8/1979 | Stark et al. |
| 4,207,897 A | 6/1980 | Lloyd et al. |
| 4,224,949 A | 9/1980 | Scott et al. |
| 4,226,228 A | 10/1980 | Shin et al. |
| 4,235,242 A | 11/1980 | Howson et al. |
| 4,285,347 A | 8/1981 | Hess |
| 4,291,705 A | 9/1981 | Severinghaus et al. |
| 4,309,777 A | 1/1982 | Patil |
| 4,349,921 A | 9/1982 | Kuntz |
| 4,401,112 A | 8/1983 | Rezian |
| 4,461,300 A | 7/1984 | Christensen |
| 4,501,269 A | 2/1985 | Bagby |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,018 A | 6/1986 | Rantala |
| 4,611,597 A | 9/1986 | Kraus |
| 4,633,889 A | 1/1987 | Talalla |
| 4,646,738 A | 3/1987 | Trott |
| 4,657,550 A | 4/1987 | Daher |
| 4,658,835 A | 4/1987 | Pohndorf |
| 4,743,256 A | 5/1988 | Brantigan |
| 4,744,371 A | 5/1988 | Harris |
| 4,759,377 A | 7/1988 | Dykstra |
| 4,759,766 A | 7/1988 | Buettner-Janz et al. |
| 4,759,769 A | 7/1988 | Hedman |
| 4,781,591 A | 11/1988 | Allen |
| 4,784,150 A | 11/1988 | Voorhies et al. |
| 4,807,642 A | 2/1989 | Brown |
| 4,834,757 A | 5/1989 | Brantigan |
| 4,863,477 A | 9/1989 | Monson |
| 4,877,020 A | 10/1989 | Vich |
| 4,878,915 A | 11/1989 | Brantigan |
| 4,892,105 A | 1/1990 | Prass |
| 4,913,134 A | 4/1990 | Luque |
| 4,926,865 A | 5/1990 | Oman |
| 4,932,975 A | 6/1990 | Main et al. |
| 4,950,296 A | 8/1990 | McIntyre |
| 4,961,740 A | 10/1990 | Ray et al. |
| 4,962,766 A | 10/1990 | Herzon |
| 4,964,411 A | 10/1990 | Johnson et al. |
| 4,997,432 A | 3/1991 | Keller |
| 5,007,902 A | 4/1991 | Witt |
| 5,015,247 A | 5/1991 | Michelson |
| 5,026,373 A | 6/1991 | Ray et al. |
| 5,047,055 A | 9/1991 | Bao et al. |
| 5,052,373 A | 10/1991 | Michelson |
| 5,055,104 A | 10/1991 | Ray |
| 5,058,602 A | 10/1991 | Brody |
| 5,062,845 A | 11/1991 | Kuslich et al. |
| 5,071,437 A | 12/1991 | Steffee |
| 5,081,990 A | 1/1992 | Deletis |
| 5,092,344 A | 3/1992 | Lee |
| 5,092,572 A | 3/1992 | Litwak et al. |
| 5,123,926 A | 6/1992 | Pisharodi |
| 5,127,403 A | 7/1992 | Brownlee |
| 5,133,717 A | 7/1992 | Chopin |
| 5,133,755 A | 7/1992 | Brekke |
| 5,161,533 A | 11/1992 | Prass et al. |
| 5,171,278 A | 12/1992 | Pisharodi |
| 5,171,279 A | 12/1992 | Mathews |
| 5,192,327 A | 3/1993 | Brantigan |
| 5,195,541 A | 3/1993 | Obenchain |
| 5,196,015 A | 3/1993 | Neubardt |
| 5,217,497 A | 6/1993 | Mehdian |
| 5,236,460 A | 8/1993 | Barber |
| RE34,390 E | 9/1993 | Culver |
| 5,255,691 A | 10/1993 | Otten |
| 5,258,031 A | 11/1993 | Salib |
| 5,263,953 A | 11/1993 | Bagby |
| 5,269,785 A | 12/1993 | Bonutti |
| 5,282,468 A | 2/1994 | Klepinski |
| 5,284,153 A | 2/1994 | Raymond et al. |
| 5,284,154 A | 2/1994 | Raymond et al. |
| 5,290,494 A | 3/1994 | Coombes et al. |
| 5,295,994 A | 3/1994 | Bonutti |
| 5,299,563 A | 4/1994 | Seton |
| 5,300,076 A | 4/1994 | Lerich |
| 5,304,210 A | 4/1994 | Crook |
| 5,306,307 A | 4/1994 | Senter et al. |
| 5,306,309 A | 4/1994 | Wagner et al. |
| 5,312,417 A | 5/1994 | Wilk |
| 5,313,956 A | 5/1994 | Knutsson et al. |
| 5,313,962 A | 5/1994 | Obenchain |
| 5,314,477 A | 5/1994 | Marnay |
| 5,320,644 A | 6/1994 | Baumgartner |
| 5,322,505 A | 6/1994 | Krause et al. |
| 5,327,902 A | 7/1994 | Lemmen |
| 5,331,975 A | 7/1994 | Bonutti |
| 5,333,618 A | 8/1994 | Lekhtman et al. |
| 5,334,205 A | 8/1994 | Cain |
| 5,336,223 A | 8/1994 | Rogers |
| 5,342,384 A | 8/1994 | Sugarbaker |
| 5,364,400 A | 11/1994 | Rego, Jr. et al. |
| 5,375,067 A | 12/1994 | Berchin |
| 5,375,594 A | 12/1994 | Cueva |
| 5,383,876 A | 1/1995 | Nardella |
| 5,395,317 A | 3/1995 | Kambin |
| 5,395,372 A | 3/1995 | Holt et al. |
| 5,397,363 A | 3/1995 | Gelbard |
| 5,397,364 A | 3/1995 | Kozak |
| 5,401,269 A | 3/1995 | Buttner-Janz |
| 5,405,391 A | 4/1995 | Henderson et al. |
| 5,413,602 A | 5/1995 | Metz-Stavenhagen |
| 5,425,772 A | 6/1995 | Brantigan |
| 5,425,773 A | 6/1995 | Boyd et al. |
| 5,431,658 A | 7/1995 | Moskovich |
| 5,443,514 A | 8/1995 | Steffee |

(56) References Cited

U.S. PATENT DOCUMENTS

| | | |
|---|---|---|
| 5,443,515 A | 8/1995 | Cohen et al. |
| 5,445,639 A | 8/1995 | Kuslich et al. |
| 5,450,845 A | 9/1995 | Alexgaard |
| 5,454,811 A | 10/1995 | Huebner |
| 5,458,638 A | 10/1995 | Kuslich et al. |
| 5,458,642 A | 10/1995 | Beer |
| 5,474,057 A | 12/1995 | Makower et al. |
| 5,474,558 A | 12/1995 | Neubardt |
| 5,480,440 A | 1/1996 | Kambin |
| 5,480,442 A | 1/1996 | Bertagnoli |
| 5,482,038 A | 1/1996 | Ruff |
| 5,484,403 A | 1/1996 | Yoakum et al. |
| 5,484,437 A | 1/1996 | Michelson |
| 5,489,307 A | 2/1996 | Kuslich et al. |
| 5,489,308 A | 2/1996 | Kuslich et al. |
| 5,509,893 A | 4/1996 | Pracas |
| 5,514,153 A | 5/1996 | Bonutti |
| 5,514,180 A | 5/1996 | Heggeness et al. |
| 5,522,879 A | 6/1996 | Scopelianos |
| 5,522,899 A | 6/1996 | Michelson |
| 5,524,624 A | 6/1996 | Tepper et al. |
| 5,527,312 A | 6/1996 | Ray |
| 5,534,029 A | 7/1996 | Shima |
| 5,534,030 A | 7/1996 | Navarro et al. |
| 5,540,235 A | 7/1996 | Wilson |
| 5,540,688 A | 7/1996 | Navas |
| 5,545,222 A | 8/1996 | Bonutti |
| 5,549,656 A | 8/1996 | Reiss |
| 5,556,431 A | 9/1996 | Buttner-Janz |
| 5,560,372 A | 10/1996 | Cory |
| 5,562,736 A | 10/1996 | Ray et al. |
| 5,562,738 A | 10/1996 | Boyd |
| 5,565,005 A | 10/1996 | Erickson et al. |
| 5,566,678 A | 10/1996 | Cadwell |
| 5,571,149 A | 11/1996 | Liss et al. |
| 5,571,190 A | 11/1996 | Ulrich |
| 5,571,192 A | 11/1996 | Schonhoffer |
| 5,579,781 A | 12/1996 | Cooke |
| 5,593,409 A | 1/1997 | Michelson |
| 5,593,429 A | 1/1997 | Ruff |
| 5,599,279 A | 2/1997 | Slotman et al. |
| 5,609,636 A | 3/1997 | Kohrs et al. |
| 5,611,800 A | 3/1997 | Davis et al. |
| 5,611,810 A | 3/1997 | Arnold et al. |
| 5,630,813 A | 5/1997 | Kieturakis |
| 5,632,747 A | 5/1997 | Scarborough et al. |
| 5,645,598 A | 7/1997 | Brosnahan et al. |
| 5,653,761 A | 8/1997 | Pisharodi |
| 5,653,762 A | 8/1997 | Pisharodi |
| 5,658,336 A | 8/1997 | Pisdharodi |
| 5,658,337 A | 8/1997 | Kohrs et al. |
| 5,662,710 A | 9/1997 | Bonutti |
| 5,665,122 A | 9/1997 | Kambin |
| 5,667,508 A | 9/1997 | Errico et al. |
| 5,669,909 A | 9/1997 | Zdeblick et al. |
| 5,671,752 A | 9/1997 | Sinderby et al. |
| 5,674,296 A | 10/1997 | Bryan |
| 5,676,701 A | 10/1997 | Yuan et al. |
| 5,676,702 A | 10/1997 | Ratron |
| 5,676,703 A | 10/1997 | Gelbard |
| 5,681,265 A | 10/1997 | Maeda et al. |
| 5,683,394 A | 11/1997 | Rinner |
| 5,683,400 A | 11/1997 | McGuire |
| 5,683,464 A | 11/1997 | Wagner et al. |
| 5,683,465 A | 11/1997 | Shinn |
| 5,690,629 A | 11/1997 | Asher et al. |
| 5,700,264 A | 12/1997 | Zucherman et al. |
| 5,700,291 A | 12/1997 | Kuslich et al. |
| 5,700,292 A | 12/1997 | Marguiles |
| 5,702,449 A | 12/1997 | McKay |
| 5,702,450 A | 12/1997 | Bisserie |
| 5,702,451 A | 12/1997 | Biedermann et al. |
| 5,702,453 A | 12/1997 | Rabbe et al. |
| 5,702,454 A | 12/1997 | Baumgartner |
| 5,702,455 A | 12/1997 | Saggar |
| 5,703,451 A | 12/1997 | Yamamichi |
| 5,707,359 A | 1/1998 | Bufalini |
| 5,707,373 A | 1/1998 | Sevrain et al. |
| 5,711,307 A | 1/1998 | Smits |
| 5,711,957 A | 1/1998 | Patat et al. |
| 5,716,415 A | 2/1998 | Steffee |
| 5,720,748 A | 2/1998 | Kuslich et al. |
| 5,720,751 A | 2/1998 | Jackson |
| 5,728,046 A | 3/1998 | Mayer et al. |
| 5,728,159 A | 3/1998 | Stroever et al. |
| 5,741,253 A | 4/1998 | Michelson |
| 5,741,261 A | 4/1998 | Moskovitz et al. |
| 5,755,796 A | 5/1998 | Ibo et al. |
| 5,755,797 A | 5/1998 | Baumgartner |
| 5,755,798 A | 5/1998 | Papavero |
| 5,759,159 A | 6/1998 | Masreliez |
| 5,762,629 A | 6/1998 | Kambin |
| 5,766,252 A | 6/1998 | Henry et al. |
| 5,772,661 A | 6/1998 | Michelson |
| 5,775,331 A | 7/1998 | Raymond et al. |
| 5,775,797 A | 7/1998 | Henstra |
| 5,776,144 A | 7/1998 | Leysieffer et al. |
| 5,779,642 A | 7/1998 | Nightengale |
| 5,782,830 A | 7/1998 | Farris |
| 5,782,832 A | 7/1998 | Larsen |
| 5,782,919 A | 7/1998 | Zdeblick et al. |
| 5,785,658 A | 7/1998 | Benaron |
| 5,785,710 A | 7/1998 | Michelson |
| 5,792,044 A | 8/1998 | Foley et al. |
| 5,797,854 A | 8/1998 | Hedgecock |
| 5,797,909 A | 8/1998 | Michelson |
| 5,800,549 A | 9/1998 | Bao et al. |
| 5,800,550 A | 9/1998 | Sertich |
| 5,814,073 A | 9/1998 | Bonutti |
| 5,814,084 A | 9/1998 | Grivas et al. |
| 5,824,094 A | 10/1998 | Serhan |
| 5,827,328 A | 10/1998 | Butterman |
| 5,830,151 A | 11/1998 | Hadzic et al. |
| 5,851,191 A | 12/1998 | Gozani |
| 5,851,208 A | 12/1998 | Trott |
| 5,853,373 A | 12/1998 | Griffith et al. |
| 5,860,973 A | 1/1999 | Michelson |
| 5,861,041 A | 1/1999 | Tienboon |
| 5,862,314 A | 1/1999 | Jeddeloh |
| 5,865,845 A | 2/1999 | Thalgott |
| 5,865,846 A | 2/1999 | Bryan |
| 5,865,848 A | 2/1999 | Baker |
| 5,872,314 A | 2/1999 | Clinton |
| 5,885,210 A | 3/1999 | Cox |
| 5,885,219 A | 3/1999 | Nightengale |
| 5,885,299 A | 3/1999 | Winslow et al. |
| 5,888,196 A | 3/1999 | Bonutti |
| 5,888,219 A | 3/1999 | Bonutti |
| 5,888,223 A | 3/1999 | Bray |
| 5,888,224 A | 3/1999 | Beckers et al. |
| 5,888,226 A | 3/1999 | Rogozinski |
| 5,891,147 A | 4/1999 | Moskovitz et al. |
| 5,893,889 A | 4/1999 | Harrington |
| 5,893,890 A | 4/1999 | Pisharodi |
| 5,895,428 A | 4/1999 | Berry |
| 5,902,231 A | 5/1999 | Foley et al. |
| 5,904,719 A | 5/1999 | Errico et al. |
| 5,910,315 A | 6/1999 | Stevenson et al. |
| 5,928,139 A | 7/1999 | Koros et al. |
| 5,928,158 A | 7/1999 | Aristides |
| 5,928,284 A | 7/1999 | Mehdizadeh |
| 5,931,777 A | 8/1999 | Sava |
| 5,935,131 A | 8/1999 | Bonutti et al. |
| 5,938,688 A | 8/1999 | Schiff |
| 5,942,698 A | 8/1999 | Stevens |
| 5,944,658 A | 8/1999 | Koros et al. |
| 5,954,769 A | 9/1999 | Rosenlicht |
| 5,968,098 A | 10/1999 | Winslow |
| 5,976,094 A | 11/1999 | Gozani et al. |
| 5,993,474 A | 11/1999 | Ouchi |
| 6,001,130 A | 12/1999 | Bryan |
| 6,003,426 A | 12/1999 | Kobayashi et al. |
| 6,004,262 A | 12/1999 | Putz et al. |
| 6,004,312 A | 12/1999 | Finneran |

(56) References Cited

U.S. PATENT DOCUMENTS

| | | |
|---|---|---|
| 6,004,326 A | 12/1999 | Castro et al. |
| 6,007,487 A | 12/1999 | Foley et al. |
| 6,008,433 A | 12/1999 | Stone |
| 6,015,436 A | 1/2000 | Schunhuffer |
| 6,019,792 A | 2/2000 | Cauthen |
| 6,024,696 A | 2/2000 | Hoftman et al. |
| 6,027,456 A | 2/2000 | Feler et al. |
| 6,033,405 A | 3/2000 | Winslow et al. |
| 6,038,469 A | 3/2000 | Karlsson et al. |
| 6,038,477 A | 3/2000 | Kayyali |
| 6,039,761 A | 3/2000 | Li et al. |
| 6,039,763 A | 3/2000 | Shekolov |
| 6,042,582 A | 3/2000 | Ray |
| 6,045,579 A | 4/2000 | Hochshuler |
| 6,045,580 A | 4/2000 | Scarborough et al. |
| 6,048,342 A | 4/2000 | Zucherman et al. |
| 6,050,992 A | 4/2000 | Nichols |
| 6,059,829 A | 5/2000 | Schlapfer et al. |
| 6,063,088 A | 5/2000 | Winslow |
| 6,063,121 A | 5/2000 | Xavier |
| 6,074,343 A | 6/2000 | Nathanson et al. |
| 6,080,193 A | 6/2000 | Hochshuler |
| 6,083,154 A | 7/2000 | Liu et al. |
| 6,083,225 A | 7/2000 | Winslow et al. |
| 6,086,613 A | 7/2000 | Camino |
| 6,095,987 A | 8/2000 | Schmulewitz |
| 6,096,080 A | 8/2000 | Nicholson et al. |
| 6,102,948 A | 8/2000 | Brosnahan, III |
| 6,102,950 A | 8/2000 | Vaccaro |
| 6,104,957 A | 8/2000 | Alo et al. |
| 6,104,960 A | 8/2000 | Duysens et al. |
| 6,113,637 A | 9/2000 | Gill |
| 6,113,638 A | 9/2000 | Williams |
| 6,120,503 A | 9/2000 | Michelson |
| 6,120,506 A | 9/2000 | Kohrs et al. |
| 6,126,660 A | 10/2000 | Dietz |
| 6,132,386 A | 10/2000 | Gozani et al. |
| 6,132,387 A | 10/2000 | Gozani et al. |
| 6,132,472 A | 10/2000 | Bonutti |
| 6,135,965 A | 10/2000 | Tumer et al. |
| 6,136,031 A | 10/2000 | Middleton |
| 6,139,493 A | 10/2000 | Koros et al. |
| 6,139,579 A | 10/2000 | Steffee |
| 6,143,033 A | 11/2000 | Paul et al. |
| 6,146,335 A | 11/2000 | Gozani |
| 6,146,421 A | 11/2000 | Gordon |
| 6,152,871 A | 11/2000 | Foley et al. |
| 6,156,067 A | 12/2000 | Bryan |
| 6,159,211 A | 12/2000 | Boriani et al. |
| 6,159,215 A | 12/2000 | Urbahns et al. |
| 6,161,047 A | 12/2000 | King et al. |
| 6,162,252 A | 12/2000 | Kuras |
| 6,174,311 B1 | 1/2001 | Branch et al. |
| 6,176,882 B1 | 1/2001 | Biedermann et al. |
| 6,179,874 B1 | 1/2001 | Cauthen |
| 6,181,961 B1 | 1/2001 | Prass |
| 6,193,756 B1 | 2/2001 | Studer et al. |
| 6,196,969 B1 | 3/2001 | Bester et al. |
| 6,200,347 B1 | 3/2001 | Anderson |
| 6,206,826 B1 | 3/2001 | Mathews et al. |
| 6,217,509 B1 | 4/2001 | Foley et al. |
| 6,224,549 B1 | 5/2001 | Drongelen |
| 6,224,607 B1 | 5/2001 | Michelson |
| 6,224,631 B1 | 5/2001 | Kohrs |
| 6,228,118 B1 | 5/2001 | Gordon |
| 6,231,609 B1 | 5/2001 | Mehdizadeh |
| 6,241,769 B1 | 6/2001 | Nicholson et al. |
| 6,241,771 B1 | 6/2001 | Gresser et al. |
| 6,251,140 B1 | 6/2001 | Marino et al. |
| 6,258,125 B1 | 7/2001 | Paul et al. |
| 6,259,945 B1 | 7/2001 | Epstein et al. |
| 6,264,651 B1 | 7/2001 | Underwood et al. |
| 6,266,558 B1 | 7/2001 | Gozani et al. |
| 6,273,905 B1 | 8/2001 | Streeter |
| 6,277,149 B1 | 8/2001 | Boyle et al. |
| 6,292,701 B1 | 9/2001 | Prass et al. |
| 6,296,664 B1 | 10/2001 | Middleton |
| 6,296,665 B1 | 10/2001 | Strnad |
| 6,306,100 B1 | 10/2001 | Prass |
| 6,308,712 B1 | 10/2001 | Shaw |
| 6,312,392 B1 | 11/2001 | Herzon |
| 6,319,257 B1 | 11/2001 | Carignan et al. |
| 6,325,764 B1 | 12/2001 | Griffith et al. |
| 6,334,068 B1 | 12/2001 | Hacker |
| 6,348,058 B1 | 2/2002 | Melkent et al. |
| 6,360,750 B1 | 3/2002 | Gerber et al. |
| 6,371,968 B1 | 4/2002 | Kogasaka et al. |
| 6,371,989 B1 | 4/2002 | Chauvin et al. |
| 6,383,221 B1 | 5/2002 | Scarborough et al. |
| 6,409,766 B1 | 6/2002 | Brett |
| 6,425,772 B1 | 7/2002 | Bernier et al. |
| 6,425,859 B1 | 7/2002 | Foley et al. |
| 6,425,901 B1 | 7/2002 | Zhu et al. |
| 6,432,140 B1 | 8/2002 | Lin |
| 6,440,142 B1 | 8/2002 | Ralph et al. |
| 6,442,814 B1 | 9/2002 | Landry et al. |
| 6,447,547 B1 | 9/2002 | Michelson |
| 6,450,952 B1 | 9/2002 | Rioux et al. |
| 6,451,015 B1 | 9/2002 | Rittman, III et al. |
| 6,454,806 B1 | 9/2002 | Cohen et al. |
| 6,466,817 B1 | 10/2002 | Kaula et al. |
| 6,468,205 B1 | 10/2002 | Mollenauer et al. |
| 6,468,207 B1 | 10/2002 | Fowler, Jr. |
| 6,468,311 B2 | 10/2002 | Boyd et al. |
| 6,491,724 B1 | 12/2002 | Ferree |
| 6,500,128 B2 | 12/2002 | Marino |
| 6,520,907 B1 | 2/2003 | Foley et al. |
| 6,524,320 B2 | 2/2003 | DiPoto |
| 6,527,773 B1 | 3/2003 | Lin et al. |
| 6,535,759 B1 | 3/2003 | Epstein et al. |
| D472,634 S | 4/2003 | Anderson |
| D473,650 S | 4/2003 | Anderson |
| 6,547,823 B2 | 4/2003 | Scarborough et al. |
| 6,564,078 B1 | 5/2003 | Marino et al. |
| 6,579,244 B2 | 6/2003 | Goodwin |
| 6,595,998 B2 | 7/2003 | Johnson et al. |
| 6,620,157 B1 | 9/2003 | Dabney et al. |
| 6,626,905 B1 | 9/2003 | Schmiel et al. |
| 6,635,086 B2 | 10/2003 | Lin |
| 6,645,194 B2 | 11/2003 | Briscoe et al. |
| 6,648,895 B2 | 11/2003 | Burkus et al. |
| 6,672,019 B1 | 1/2004 | Wenz |
| 6,676,703 B2 | 1/2004 | Biscup |
| 6,679,833 B2 | 1/2004 | Smith et al. |
| 6,706,067 B2 | 3/2004 | Shimp et al. |
| 6,719,692 B2 | 4/2004 | Kleffner et al. |
| 6,743,255 B2 | 6/2004 | Ferree |
| 6,746,484 B1 | 6/2004 | Liu et al. |
| 6,755,841 B2 | 6/2004 | Fraser et al. |
| 6,760,616 B2 | 7/2004 | Hoey et al. |
| 6,761,739 B2 | 7/2004 | Shepard |
| 6,770,074 B2 | 8/2004 | Michelson |
| 6,796,985 B2 | 9/2004 | Bolger et al. |
| 6,810,281 B2 | 10/2004 | Brock et al. |
| 6,819,956 B2 | 11/2004 | DiLorenzo |
| 6,824,564 B2 | 11/2004 | Crozet |
| 6,847,849 B2 | 1/2005 | Mamo et al. |
| 6,849,047 B2 | 2/2005 | Goodwin |
| 6,855,105 B2 | 2/2005 | Jackson, III et al. |
| 6,871,099 B1 | 3/2005 | Whitehurst et al. |
| D503,801 S | 4/2005 | Jackson |
| 6,902,569 B2 | 6/2005 | Parmer et al. |
| 6,923,814 B1 | 8/2005 | Hildebrand et al. |
| 6,926,728 B2 | 8/2005 | Zucherman et al. |
| 6,929,606 B2 | 8/2005 | Ritland |
| 6,942,698 B1 | 9/2005 | Jackson |
| 6,945,933 B2 | 9/2005 | Branch |
| 6,951,538 B2 | 10/2005 | Ritland |
| 6,964,687 B1 | 11/2005 | Bernard et al. |
| 6,979,353 B2 | 12/2005 | Bresina |
| 6,984,245 B2 | 1/2006 | McGahan et al. |
| 6,986,788 B2 | 1/2006 | Paul et al. |
| 6,989,031 B2 | 1/2006 | Michelson |
| 7,018,416 B2 | 3/2006 | Hanson et al. |

(56) References Cited

U.S. PATENT DOCUMENTS

| | | | |
|---|---|---|---|
| 7,047,082 B1 | 5/2006 | Schrom et al. | |
| 7,050,848 B2 | 5/2006 | Hoey et al. | |
| 7,079,883 B2 | 7/2006 | Marino et al. | |
| 7,089,059 B1 | 8/2006 | Pless | |
| D530,423 S | 10/2006 | Miles et al. | |
| 7,177,677 B2 | 2/2007 | Kaula et al. | |
| 7,198,598 B2 | 4/2007 | Smith et al. | |
| 7,207,949 B2 | 4/2007 | Miles et al. | |
| 7,226,451 B2 | 6/2007 | Shluzas et al. | |
| 7,261,688 B2 | 8/2007 | Smith et al. | |
| 7,470,236 B1 | 12/2008 | Kelleher et al. | |
| 7,473,222 B2 | 1/2009 | Dewey et al. | |
| 7,481,766 B2 | 1/2009 | Lee et al. | |
| 7,522,953 B2 | 4/2009 | Kaula et al. | |
| 7,556,601 B2 | 7/2009 | Branch et al. | |
| 7,582,058 B1 | 9/2009 | Miles et al. | |
| 7,643,884 B2 | 1/2010 | Pond et al. | |
| 7,691,057 B2 | 4/2010 | Miles et al. | |
| 7,717,959 B2 | 5/2010 | William et al. | |
| 7,819,801 B2 | 10/2010 | Miles et al. | |
| 7,935,051 B2 | 5/2011 | Miles et al. | |
| 8,328,851 B2 * | 12/2012 | Curran et al. | 606/279 |
| 2001/0039949 A1 | 11/2001 | Loubser | |
| 2001/0056280 A1 | 12/2001 | Underwood et al. | |
| 2002/0007129 A1 | 1/2002 | Marino | |
| 2002/0010392 A1 | 1/2002 | Desai | |
| 2002/0058950 A1 | 5/2002 | Winterbottom et al. | |
| 2002/0072686 A1 | 6/2002 | Hoey et al. | |
| 2002/0077632 A1 | 6/2002 | Tsou | |
| 2002/0123780 A1 | 9/2002 | Grill et al. | |
| 2002/0161415 A1 | 10/2002 | Cohen et al. | |
| 2002/0193843 A1 | 12/2002 | Hill et al. | |
| 2003/0032966 A1 | 2/2003 | Foley et al. | |
| 2003/0105503 A1 | 6/2003 | Marino | |
| 2003/0105528 A1 | 6/2003 | Shimp et al. | |
| 2003/0139648 A1 | 7/2003 | Foley et al. | |
| 2003/0139812 A1 | 7/2003 | Garcia et al. | |
| 2003/0149341 A1 | 8/2003 | Clifton | |
| 2003/0225405 A1 | 12/2003 | Weiner | |
| 2003/0236544 A1 | 12/2003 | Lunsford et al. | |
| 2004/0153155 A1 | 8/2004 | Chung et al. | |
| 2004/0199084 A1 | 10/2004 | Kelleher et al. | |
| 2004/0225228 A1 | 11/2004 | Ferree | |
| 2005/0004593 A1 | 1/2005 | Simonson | |
| 2005/0004623 A1 | 1/2005 | Miles et al. | |
| 2005/0033380 A1 | 2/2005 | Tanner et al. | |
| 2005/0075578 A1 | 4/2005 | Gharib et al. | |
| 2005/0080320 A1 | 4/2005 | Lee et al. | |
| 2005/0113926 A1 | 5/2005 | Zucherman | |
| 2005/0125065 A1 | 6/2005 | Zucherman | |
| 2005/0143820 A1 | 6/2005 | Zucherman | |
| 2005/0149035 A1 | 7/2005 | Pimenta et al. | |
| 2005/0154462 A1 | 7/2005 | Zucherman | |
| 2005/0182454 A1 | 8/2005 | Gharib et al. | |
| 2005/0192575 A1 | 9/2005 | Pacheco | |
| 2005/0197702 A1 | 9/2005 | Coppes et al. | |
| 2005/0283242 A1 | 12/2005 | Zucherman | |
| 2005/0283243 A1 | 12/2005 | Zucherman | |
| 2006/0025703 A1 | 2/2006 | Miles et al. | |
| 2006/0052828 A1 | 3/2006 | Kim et al. | |
| 2006/0069315 A1 | 3/2006 | Miles et al. | |
| 2006/0224078 A1 | 10/2006 | Hoey et al. | |
| 2007/0016097 A1 | 1/2007 | Farquhar et al. | |
| 2007/0191945 A1 | 8/2007 | Yu et al. | |
| 2007/0198062 A1 | 8/2007 | Miles et al. | |
| 2007/0293782 A1 | 12/2007 | Marino | |
| 2008/0058606 A1 | 3/2008 | Miles et al. | |
| 2008/0064976 A1 | 3/2008 | Kelleher et al. | |
| 2008/0064977 A1 | 3/2008 | Kelleher et al. | |
| 2008/0065178 A1 | 3/2008 | Kelleher et al. | |
| 2008/0071191 A1 | 3/2008 | Kelleher et al. | |
| 2008/0097164 A1 | 4/2008 | Miles et al. | |
| 2008/0140208 A1 | 6/2008 | Zucherman | |
| 2008/0300465 A1 | 12/2008 | Feigenwinter et al. | |
| 2009/0124860 A1 | 5/2009 | Miles et al. | |
| 2009/0138050 A1 | 5/2009 | Ferree | |
| 2009/0192403 A1 | 7/2009 | Gharib et al. | |
| 2009/0204016 A1 | 8/2009 | Gharib et al. | |
| 2010/0069783 A1 | 3/2010 | Miles et al. | |
| 2010/0130827 A1 | 5/2010 | Pimenta et al. | |
| 2010/0152603 A1 | 6/2010 | Miles et al. | |
| 2010/0160738 A1 | 6/2010 | Miles et al. | |
| 2010/0174148 A1 | 7/2010 | Miles et al. | |

FOREIGN PATENT DOCUMENTS

| | | |
|---|---|---|
| EP | 0 369 603 | 5/1990 |
| EP | 0 517 030 | 5/1992 |
| EP | 0 667 127 | 8/1995 |
| EP | 0 706 876 | 4/1996 |
| EP | 0 716 840 | 6/1996 |
| EP | 0 737 448 | 10/1996 |
| EP | 0 796 593 | 9/1997 |
| EP | 0 880 938 | 2/1998 |
| EP | 0 809 974 | 4/1998 |
| EP | 0 809 975 | 4/1998 |
| EP | 0 811 356 | 4/1998 |
| EP | 0 972 538 | 1/2000 |
| FR | 2 795 624 | 1/2001 |
| WO | 90/00037 | 1/1990 |
| WO | 91/06261 | 5/1991 |
| WO | 92/14423 | 9/1992 |
| WO | 94/04100 | 3/1994 |
| WO | 94/10928 | 5/1994 |
| WO | 95/01810 | 1/1995 |
| WO | 96/08205 | 3/1996 |
| WO | 96/17564 | 3/1996 |
| WO | 96/41582 | 12/1996 |
| WO | 97/20513 | 6/1997 |
| WO | 97/33525 | 9/1997 |
| WO | 97/37620 | 10/1997 |
| WO | 98/09586 | 3/1998 |
| WO | 98/14142 | 4/1998 |
| WO | 98/17208 | 4/1998 |
| WO | 98/25539 | 6/1998 |
| WO | 99/08627 | 2/1999 |
| WO | 99/38461 | 8/1999 |
| WO | 00/38574 | 7/2000 |
| WO | 00/45712 | 8/2000 |
| WO | 00/45713 | 8/2000 |
| WO | 00/66217 | 11/2000 |
| WO | 00/67645 | 11/2000 |
| WO | 01/37728 | 5/2001 |
| WO | 01/41681 | 6/2001 |
| WO | 01/49333 | 7/2001 |
| WO | 02/054960 | 7/2002 |
| WO | 03/005887 | 1/2003 |
| WO | 03/026482 | 4/2003 |
| WO | 03/037170 | 5/2003 |
| WO | 2005/013805 | 2/2005 |
| WO | 2005/030318 | 4/2005 |
| WO | 2006/042241 | 4/2006 |
| WO | 2006/066217 | 6/2006 |

OTHER PUBLICATIONS

Dirksmeier et al., "Microendoscopic and Open Laminotomy and Discectomy in Lumbar Disc Disease" *Seminars in Spine Surgery*, 1999, 11(2): 138-146.
METRx Delivered Order Form, 1999, 13 pages.
Medtronic Sofamor Danek "METRx™ MicroDisectomy System," *Medtronic Sofamor Danek USA*, 2000, 21 pgs.
Medtronic Sofamor Danek "METRx System Surgical Technique," 2004, 22 pages.
"MetRx System MicroEndoscopic Discectomy: An Evolution in Minimally Invasive Spine Surgery," *Sofamor Danek*, 1999, 6 pages.
Smith and Foley "MetRx System MicroEndoscopic Discectomy: Surgical Technique" *Medtronic Sofamor Danek*, 2000, 24 pages.
"Sofamor Danek MED Microendoscopic Discectomy System Brochure" including Rapp "New endoscopic lumbar technique improves access preserves tissue" Reprinted with permission from: *Orthopedics Today*, 1998, 18(1): 2 pages.

(56) References Cited

OTHER PUBLICATIONS

Japanese Patent Office JP Patent Application No. 2006-528306 Office Action with English Translation, Jun. 10, 2009, 4 pages.
Axon 501(k) Notification: Epoch 2000 Neurological Workstation, Dec. 3, 1997, 464 pages.
Foley and Smith, "Microendoscopic Discectomy," *Techniques in Neurosurgery*, 1997, 3(4):301-307.
Medtronic Sofamor Danek "UNION™ / UNION-L™ Anterior & Lateral Impacted Fusion Devices: Clear choice of stabilization," *Medtronic Sofamor Danek*, 2000, 4 pages.
NuVasive Vector™ Cannulae, 2000, 1 page.
NuVasive Triad™ Tri-Columnar Spinal EndoArthrodesis™ via Minimally Invasive Guidance, 2000, 1 page (prior to Sep. 25, 2003).
NuVasive Triad™ Cortical Bone Allograft, 2000, 1 page (prior to Sep. 25, 2003).
NuVasive Vertebral Body Access System, 2000, 1 page.
Marina, "New Technology for Guided Navigation with Real Time Nerve Surveillance for Minimally Invasive Spine Discectomy & Arthrodesis," *Spineline*, 2000, p. 39.
NuVasive "INS-1 Screw Test," 2001, 10 pages.
NuVasive letter re 510k Neuro Vision JJB System, Oct. 16, 2001, 5 pages.
NuVasive letter re 510k Guided Arthroscopy System, Oct. 5, 1999, 6 pages.
NuVasive letter re 510k INS-1 Intraoperative Nerve Surveillance System, Nov. 13, 2000, 7 pages.
"NuVasiveTM Receives Clearance to Market Two Key Elem Minimally Invasive Spine Surgery System," Nov. 27, 2001, 20 pages.
Schick et al., "Microendoscopic lumbar discectomy versus open surgery: an intraoperative EMG study," *Eur Spine J*, 2002, 11: 20-26.
NuVasive letter re: 510(k) for Neurovision JJB System (Summary), Sep. 25, 2001, 28 pages.
NuVasive letter re: Special 510(k) Premarket Notification: Neurovision JJB System (Device Description), Jul. 3, 2003, 18 pages.
NuVasive letter re: Special 510(k) Premarket Notification: Neurovision JJB System (Device Description), Mar. 1, 2004, 16 pages.
NuVasive letter re: Special 510(k) Premarket Notification: Neurovision JJB System (Device Description), May 26, 2005, 17 pages.
NuVasive letter re: 510(k) Premarket Notification: Neurovision JJB System (Device Description), Jun. 24, 2005, 16 pages.
NuVasive letter re: Special 510(k) Premarket Notification: Neurovision JJB System (Device Description), Sep. 14, 2006, 17 pages.
NuVasive 510(k) Premarket Notification: Neurovision JJB System (Device Description), Aug. 20, 2007, 8 pages.
NuVasive letter re: 510(k) Premarket Notification: Guided Spinal Arthroscopy System (Device Description), Feb. 1, 1999, 40 pages.
NuVasive 510(k) Premarket Notification: Spinal System (Summary), Apr. 12, 2004, 10 pages.
NuVasive 510(k) Summary NIM Monitor, Sep. 4, 1998, 4 pages.
NuVasive correspondence re 510(k) Premarket Notification INS-1 Intraoperative Nerve Surveillance System: Section IV Device Description, pp. 12-51 (prior to Sep. 25, 2003).
Isley et al., "Recent Advances in Intraoperative Neuromonitoring of Spinal Cord Function: Pedicle Screw Stimulation Techniques," *American Journal of Electroneurodagnostic Technology*, Jun. 1997, 37(2): 93-126.
Mathews et al., "Laparoscopic Discectomy with Anterior Lumbar Interbody Fusion," *Spine*, 1995, 20(16): 1797-1802.
Rose et al., "Persistently Electrified Pedicle Stimulation Instruments in Spinal Instrumentation: Techniques and Protocol Development," *Spine*, 1997, 22(3): 334-343.
"Electromyography System," International Search report from International Application No. PCT/US00/32329, Apr. 27, 2001, 9 pages.
"Nerve Proximity and Status Detection System and Method," International Search Report from International Application No. PCT/US01/18606, Oct. 18, 2001, 6 pages.
"Relative Nerve Movement and Status Detection System and Method," International Search Report from International Application No. PCT/US01/18579, Jan. 15, 2002, 6 pages.

"System and Method for Determining Nerve Proximity Direction and Pathology During Surgery," International Search Report from International Application No. PCT/US02/22247, Mar. 27, 2003, 4 pages.
"System and Methods for Determining Nerve Direction to a Surgical Instrument," International Search Report from International Application No. PCT/US03/02056, Aug. 12, 2003, 5 pages.
"Systems and Methods for Performing Percutaneous Pedicle Integrity Assessments," International Search Report from International Application No. PCT/US02/35047, Aug. 11, 2003, 5 pages.
"Systems and Methods for Performing Surgery Procedures and Assessments," International Search Report from International Application No. PCT/US02/30617, Jun. 5, 2003, 4 pages.
Lenke et al., "Triggered Electromyographic Threshold for Accuracy of Pedicle Screw Placement," *Spine*, 1995, 20(4): 1585-1591.
"Brackmann II EMG System," *Medical Electronics*, 1999, 4 pages.
"Neurovision SE Nerve Locator/Monitor", RLN Systems Inc. Operators Manual, 1999, 22 pages.
"The Brackmann II EMG Monitoring System," Medical Electronics Co. Operator's Manual Version 1.1, 1995, 50 pages.
"The Nicolet Viking IV," Nicolet Biomedical Products, 1999, 6 pages.
Anderson et al., "Pedicle screws with high electrical resistance: a potential source of error with stimulus-evoked EMG," *Spine*, Departmentof Orthopaedic Surgery University of Virginia, Jul. 15, 2002, 27(14): 1577-1581.
Bose et al., "Neurophysiologic Monitoring of Spinal Nerve Root Function During Instrumented Posterior Lumber Spine Surgery," *Spine*, 2002, 27(13):1444-1450.
Calancie et al., "Stimulus-Evoked EMG Monitoring During Transpedicular Lumbosacral Spine Instrumentation" *Spine*, 1994, 19(24): 2780-2786.
Clements et al., "Evoked and Spontaneous Electromyography to Evaluate Lumbosacral Pedicle Screw Placement," *Spine*, 1996, 21(5): 600-604.
Danesh-Clough et al. ,"The Use of Evoked EMG in Detecting Misplaced Thoracolumbar Pedicle Screws," *Spine*, Orthopaedic Department Dunedin Hospital, Jun. 15, 2001, 26(12): 1313-1316.
Darden et al., "A Comparison of Impedance and Electromyogram Measurements in Detecting the Presence of Pedicle Wall Breakthrough," *Spine*, Charlotte Spine Center North Carolina, Jan. 15, 1998, 23(2): 256-262.
Ebraheim et al., "Anatomic Relations Between the Lumbar Pedicle and the Adjacent Neural Structures," *Spine*, Department of Orthopaedic Surgery Medical College of Ohio, Oct. 15, 1997, 22(20): 2338-2341.
Ford et al. "Electrical Characteristics of Peripheral Nerve Stimulators Implications for Nerve Localization," *Regional Anesthesia*, 1984, 9: 73-77.
Glassman et al., "A Prospective Analysis of Intraoperative Electromyographic Monitoring of Pedicle Screw Placement With Computed Tomographic Scan Confirmation," *Spine*, 1995, 20(12): 1375-1379.
Greenblatt et al., "Needle Nerve Stimulator-Locator: Nerve Blocks with a New Instrument for Locating Nerves," *Anesthesia& Analgesia*, 1962, 41(5): 599-602.
Haig, "Point of view," *Spine*, 2002, 27(24): 2819.
Haig et al., "The Relation Among Spinal Geometry on MRI, Paraspinal Electromyographic Abnormalities, and Age in Persons Referred for Electrodiagnostic Testing of Low Back Symptoms," *Spine*, Department of Physical Medicine and Rehabilitation University of Michigan, Sep. 1, 2002, 27(17): 1918-1925.
Holland et al., "Higher Electrical Stimulus Intensities are Required to Activate Chronically Compressed Nerve Roots: Implications for Intraoperative Electromyographic Pedicle Screw Testing," *Spine*, Department of Neurology, Johns Hopkins University School of Medicine, Jan. 15, 1998, 23(2): 224-227.
Holland, "Intraoperative Electromyography During Thoracolumbar Spinal Surgery," *Spine*, 1998, 23(17): 1915-1922.
Journee et al., "System for Intra-Operative Monitoring of the Cortical Integrity of the Pedicle During Pedicle Screw Placement in Low-Back Surgery: Design and Clinical Results," *Sensory and Neuromuscular Diagnostic Instrumentation and Data Analysis I*,

(56) References Cited

OTHER PUBLICATIONS

*18th Annual International Conference on Engineering in Medicine and Biology Society*, Amsterdam, 1996, pp. 144-145.

Maguire et al., "Evaluation of Intrapedicular Screw Position Using Intraoperative Evoked Electromyography," *Spine*, 1995, 20(9): 1068-1074.

Martin et al. "Initiation of Erection and Semen Release by Rectal Probe Electrostimulation (RPE)," *The Journal of Urology*, The Williams & Wilkins Co., 1983, 129: 637-642.

Minahan et al., "The Effect of Neuromuscular Blockade on Pedicle Screw Stimulation Thresholds" *Spine*, Department of Neurology, Johns Hopkins University School of Medicine, Oct. 1, 2000, 25(19): 2526-2530.

Pither et al., "The Use of Peripheral Nerve Stimulators for Regional Anesthesia: Review of Experimental Characteristics Technique and Clinical Applications," *Regional Anesthesia*, 1985, 10:49-58.

Raj et al., "Infraclavicular Brachial Plexus Block—A New Approach" *Anesthesia and Analgesia*, 1973, (52)6: 897-904.

Raj et al., "The Use of Peripheral Nerve Stimulators for Regional Anesthesia," *Clinical Issues in Regional Anesthesia*, 1985, 1(4):1-6.

Raj et al., "Use of the Nerve Stimulator for Peripheral Blocks," *Regional Anesthesia*, Apr.-Jun. 1980, pp. 14-21.

Raymond et al., "The Nerve Seeker: A System for Automated Nerve Localization," *Regional Anesthesia*, 1992, 17(3): 151-162.

Shafik, "Cavernous Nerve Simulation through an Extrapelvic Subpubic Approach: Role in Penile Erection," *Eur. Urol*, 1994, 26: 98-102.

Toleikis et al., "The Usefulness of Electrical Stimulation for Assessing Pedicle Screw Replacements," *Journal of Spinal Disorder*, 2000, 13(4): 283-289.

Medtronic Sofamor Danek "UNION™ / UNION-L™ Anterior & Lateral Impacted Fusion Devices: Surgical Technique" *Medtronic Sofamor Danek*, 2001, 20 pages.

Bergey et al., "Endoscopic Lateral Transpsoas Approach to the Lumbar Spine," *Spine*, 2004, 29(15): 1681-1688.

Dezawa et al., "Retroperitoneal Laparoscopic Lateral Approach to the Lumbar Spine: A New Approach, Technique, and Clinical Trial," *Journal of Spinal Disorders*, 2000, 13(2): 138-143.

Gardocki, "Tubular diskectomy minimizes collateral damage: A logical progression moves spine surgery forward," *AAOS Now*, 2009, 5 pages.

Hovorka et al., "Five years' experience of retroperitoneal lumbar and thoracolumbar surgery," *Eur Spine J.*, 2000, 9(1): S30-S34.

Kossmann et al., "The use of a retractor system (SynFrame) for open, minimal invasive reconstruction of the anterior column of the thoracic and lumbar spine," *Eur Spine J.*, 2001, 10: 396-402.

Mayer, "A New Microsurgical Technique for Minimally Invasive Anterior Lumbar Interbody Fusion," *Spine*, 1997, 22(6): 691-699.

Mayer, "The ALIF Concept," *Eur Spine J.*, 2000, 9(1): S35-S43.

Mayer and Wiechert, "Microsurgical Anterior Approaches to the Lumbar Spine for Interbody Fusion and Total Disc Replacement," *Neurosurgery*, 2002, 51(2): 159-165.

McAfee et al., "Minimally Invasive Anterior Retroperitoneal Approach to the Lumbar Spine: Emphasis on the Lateral BAK," *Spine*, 1998, 23(13): 1476-1484.

Rao, et al. "Dynamic retraction of the psoas muscle to expose the lumbar spine using the retroperitoneal approach," *J. Neurosurg Spine*, 2006, 5: 468-470.

Wolfla et al., "Retroperitoneal lateral lumbar interbody fusion with titanium threaded fusion cages," *J. Neurosurg (Spine 1)*, 2002, 96: 50-55.

Larson and Maiman, "Surgery of the Lumbar Spine," Thieme Medical Publishers, Inc., 1999, pp. 305-319.

Medtronic XOMED Surgical Products, Inc., NIM—Response Nerve Integrity Monitor Intraoperative EMG Monitor User's Guide, Revision B, 2000, 47 pages.

"NuVasive's spine surgery system cleared in the US," Pharm & Medical Industry Week, Dec. 10, 2001, 1 page.

Pimenta, "Initial Clinical Results of Direct Lateral, Minimally Invasive Access to the Lumbar Spine for Disc Nucleus Replacement Using a Novel Neurophysiological Monitoring System." *The 9th IMAST*, May 2002, 1 page.

Pimenta et al., "The Lateral Endoscopic Transpsoas Retroperitoneal Approach (Letra) for Implants in the Lumbar Spine," *World Spine II—Second Interdisciplinary Congress on Spine Care*, Aug. 2003, 2 pages.

Crock, H.V. MD., "Anterior Lumbar Interbody Fusion," Clinical Orthopaedics and Related Research, Number One Hundred Sixty Five, 1982, pp. 157-163, 13 pages.

Mayer and Brock, "Percutaneous endoscopic discectomy: surgical technique and preliminary results compared to microsurgical discectomy," *J. Neurosurg*, 1993, 78: 216-225.

Schaffer and Kambin, "Percutaneous Posterolateral Lumbar Discectomy and Decompression with a 6.9-Millimeter Cannula," *The Journal of Bone and Joint Surgery*, 1991, 73A(6): 822-831.

Friedman, "Percutaneous discectomy: An alternative to chemonucleolysis," *Neurosurgery*, 1983, 13(5): 542-547.

Brau, "Chapter 22: Anterior Retroperitoneal Muscle-Sparing approach to L2-S1 of the Lumbar Spine," *Surgical Approaches to the Spine*. Robert G. Watkins, MD. (ed) 2003. pp. 165-181.

Kossmann et al., "Minimally Invasive Vertebral Replacement with Cages in Thoracic and Lumbar Spine," *European Journal of Trauma*, 2001, 27: 292-300.

Mayer H. M. (ed.) *Minimally Invasive Spine Surgery: A Surgical Manual*. 2000. 51 pages.

Pimenta et al., "Implante de protese de nucleo pulpost: analise inicial," *Journal Brasileiro de Neurocirurgia*, 2001, 12(2): 93-96.

Traynelis, "Spinal Arthroplasty," *Neurological Focus*, 2002, 13(2): 12 pages.

Zdeblick, Thomas A. (ed.). Anterior Approaches to the Spine, 1999, 43 pages.

CoRoent™ Marketing Brochure (9004001 A.0), *NuVasive, Inc.*, 2004, 2 pages.

CoRoent™ Marketing Brochure (9004001 C.0), *NuVasive, Inc.*, 2005, 2 pages.

CoRoent™ XL & XLR Marketing Brochure (9004225 A.0), *NuVasive, Inc.*, 2005, 2 pages.

CoRoent® XL & XLR Marketing Brochure (9004225 B.0), *NuVasive, Inc.*, 2006, 2 pages.

CoRoent® XL & XLR Marketing Brochure (9004225 C.0), *NuVasive, Inc.*, 2007, 2 pages.

CoRoent® XL Marketing Brochure (9500039 A.0), *NuVasive, Inc.*, 2006, 8 pages.

Baulot et al., "Complementary anterior spondylodesis by thoracoscopy. Technical note regarding an observation," *Lyon Surg.*, 1994, 90(5):347-351.

Berry et al., "A morphometric study of human lumbar and selected thoracic vertebrae, study of selected vertebrae," *Spine*, 1996, 12(4):362-367.

Crock, H. V., "A Short Practice of Spinal Surgery," Second, revised edition, published by Springer-Verlag/Wein, New York (1993).

Edeland, H.G., "Some additional suggestions for an intervertebral disc prosthesis," *Journal of Biomedical Engineering*, 1985, 7:57-62.

Kemp, H. B. S., "Anterior fusion of the spine for infective lesions in adults," *Journal of Bone & Joint Surgery*, 1973, 55B(4):715-734.

Alleyne et al., "Current and future approaches to lumbar disc surgery: A literature review", *Medscape Orthopedics & Sports Medicine*, [www.medscape.com/Medscape/OrthoSportsMed/1997/v01.n11/.../mos3057], 1997, 14 pages.

Benini et al., "Undercutting decompression and posterior fusion with translaminar facet screw fixation in degenerative lumbar spinal stenosis: Technique and results," *Neuro-Orthopedics*, 1995, 17/18: 159-172.

Kambin and Zhou, "History and current status of percutaneous arthroscopic disc surgery," *Spine*, 1996, 21(24S):57S-61S.

Stein et al., "Percutaneous facet joint fusion: Preliminary experience," *Journal of Vascular and Interventional Radiology*, 1993, 4:69-74.

Vamvanu et al., "Surgical treatment of internal disc disruption: An outcome study of four fusion techniques," *Journal of Spinal Disorders*, 1998, 11(5):375-382.

International Search Report from PCT/US06/29196, dated Feb. 1, 2007, 10 pages.

* cited by examiner

Lateral Midline

Longitudinal Midline

TDR center d1

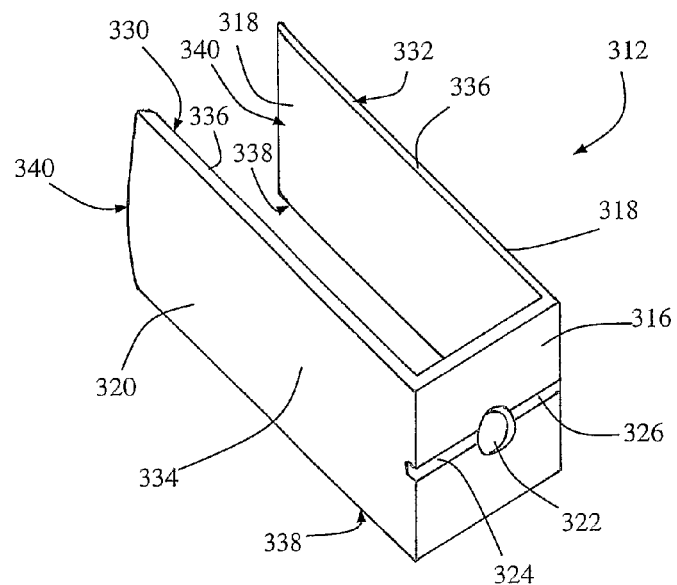
FIG. 73
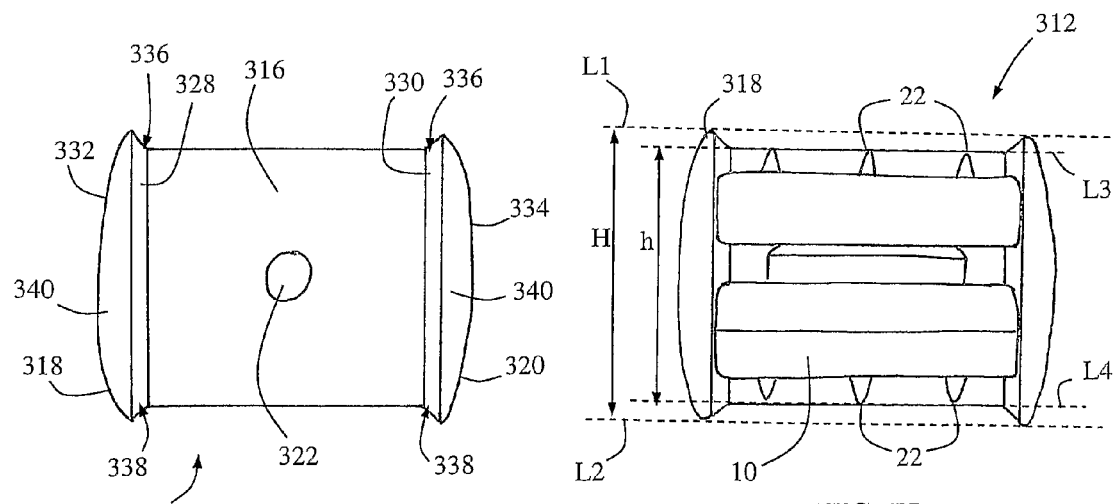
FIG. 74  FIG. 75

TOTAL DISC REPLACEMENT SYSTEM AND RELATED METHODS

CROSS-REFERENCES TO RELATED APPLICATIONS

The present application is a continuation of U.S. patent application Ser. No. 11/989,686, filed Jul. 27, 2010 (now U.S. Pat. No. 8,328,851) which was the National Stage of International Application No. PCT/US06/29196, filed Jul. 28, 2006, which claims the benefit of U.S. Provisional Application No. 60/703,645, filed Jul. 28, 2005, and U.S. Provisional Application No. 60/721,805, filed Sep. 28, 2005, the entire contents of which are each hereby incorporated by reference into this disclosure as if set forth fully herein.

BACKGROUND OF THE INVENTION

I. Field of the Invention

This disclosure relates to total disc replacement systems and related methods, and more particularly to total disc replacement systems and methods involving a lateral surgical approach to the spine.

II. Discussion of the Prior Art

In recent years, the area of total disc replacement has experienced proliferated growth and attention from the medical community. Known total disc replacement devices generally require some form of articulation or inherent flexibility in the device to permit a spine having the device to maintain its natural posture and range of motion as much as possible. Such devices typically include between 2 and 4 separate components constructed from any number of materials. Generally speaking, these components include a pair of anchor plates for engagement with opposed vertebral body endplates and one or more internal components for simulating the intervertebral disc.

The total disc replacement systems being currently commercialized are inserted using a generally anterior surgical approach. While generally effective, the anterior introduction of the existing total disc replacement systems suffer from various drawbacks. These drawbacks include, but are not necessarily limited to, challenges in placing the existing total disc replacement systems in the anterior-posterior plane, which may cause the total disc replacement system to be placed in a sub-optimal position such as too far anterior or too far posterior. Another drawback is that the anterior longitudinal ligament (ALL) is necessarily destroyed during the placement of the existing anterior total disc replacement systems. This is disadvantageous in a motion preservation situation in that it reduces the structural support that would otherwise be contributed by the ALL to help maintain the sought after motion and stability of the anterior total disc replacement system.

The present invention is directed at overcoming, or at least reducing the effects of, one or more of the problems set forth above.

SUMMARY OF THE INVENTION

The present invention solves the above-identified drawbacks with the existing anterior total disc replacement systems by providing a total disc replacement system (TDR system) including a pair of anchor plates and an intradiscal element, all of which are adapted and designed to be simultaneously introduced into a disc space from a lateral surgical approach to the spine. The lateral surgical approach may be accomplished according to the systems and methods shown and described in commonly owned and co-pending International Patent Application No. PCT/US2004/031768, entitled "Surgical Access System and Related Methods" (filed Sep. 27, 2004, claiming priority from U.S. Provisional Patent Application Ser. Nos. 60/506,136 filed Sep. 25, 2003) (the '768 PCT), the entire content of which is hereby expressly incorporated into this disclosure as if set forth fully herein. Generally speaking, the '768 PCT describes a neurophysiology-based surgical access system whereby an operative corridor may be established to a spinal target site in a generally lateral manner such that an implant may be introduced into the lateral aspect (side) of the surgical target site (e.g. disc space). According to the '768 PCT, the lateral approach is preferably retroperitoneal and trans-psoas, the latter of which is aided via the use of intra-operative neural monitoring (continuous and/or intermittent) to ensure nerves within or adjacent to the psoas muscle are not impinged upon and/or damaged during the step of establishing the operative corridor through the psoas muscle. Advantageously, the introduction of the total disc replacement system of the present invention via a lateral approach according to the '768 PCT overcomes the drawbacks of the anterior approach total disc replacement systems of the prior art. More specifically, the lateral total disc replacement system of the present invention is easy to accurately place in the anterior-posterior plane, which enhances the performance thereof based on optimal positioning (e.g. with an instantaneous axis of rotation in the posterior region of the disc space). The lateral total disc replacement system of the present invention also does not require the removal of the anterior longitudinal ligament (ALL) based on the lateral introduction into the disc space, which maintains the proper structural support of the ALL and thus ensures the sought after motion and stability of the lateral total disc replacement system of the present invention.

The first anchor plate has a first surface for engaging a first vertebra and a second surface opposite the first surface including a cutout region having a partially spherical articular surface for articulating with a first (partially spherical) surface of the intradiscal element. The second anchor plate has a first surface for engaging a second vertebra and a second generally planar surface opposite the first surface including a post member for receipt within a bore formed in a second (generally planar) surface of the intradiscal element. The post element may be positioned in any number of suitable locations on the second anchor plate. In one embodiment, the post element may be positioned off-center from an X-axis (as will be described below) such that the post element and the intradiscal element are disposed in the posterior region (e.g. in the posterior one-third) of the disc space to ensure the instantaneous axis of rotation of the total disc replacement system is disposed in the posterior region (e.g. in the posterior one-third) of the disc space. The first anchor plate, second anchor plate and/or intradiscal element may be constructed from any number of suitable materials, including but not limited to metal, ceramic, polymer, and/or any combination thereof.

The intradiscal element generally comprises a pivot member dimensioned to provide a predetermined height between the first and second anchor plates and to permit flexion (bending forwards), extension (bending backwards), lateral bending (side-to-side), and torsion (rotation). The pivot includes a first articular surface for articulation with the partially spherical articular surface of the cutout region of the first anchor plate and a second generally planar surface for engaging (fixed or translating) with the second anchor plate. The pivot may further include a central bore extending generally perpendicularly from the second surface at least partially into the pivot, the bore dimensioned to receive the post member of the second anchor plate.

The first articular surface of the intradiscal element is dimensioned to articulate with the partially spherical articular surface of the cutout region on the first anchor plate such that the first anchor plate may rotate relative to the intradiscal element about an axis (e.g. X-axis, Z-axis, or any such axis defined by a line within the XZ plane that intersects the Y-axis). The second generally planar surface of the intradiscal element is dimensioned to interact with the second generally planar surface of the second anchor plate such that the second anchor plate may rotate relative to the intradiscal element about a second axis (e.g., Y-axis). In this fashion, rotation about the first axis will always occur at the same location along the first anchor plate and rotation about the second axis will always occur at the same location along the second anchor plate.

The first and second anchor plates may each include a plurality of anchor elements for anchoring the lateral TDR device of the present invention to adjacent vertebrae. The anchor elements may include a plurality of protrusions having a cross-section comprising any number of suitable shapes, including but not limited to generally triangular. The anchor elements are preferably oriented such that the first and second anchor plates may be introduced in a generally lateral approach relative to the first and second vertebrae. In one embodiment, the anchor elements may be aligned along a longitudinal midline in one direction and along a lateral midline in another direction (ninety degrees from, and bisecting, the longitudinal midline). Anchor elements aligned in such a matter may be used as guide members during implant insertion, ensuring proper positioning of the total disc replacement system of the present invention. For example, a surgeon may align the row of anchor elements disposed along the longitudinal midline of the anchor plates with the middle of the first and second vertebral bodies (in the anterior-posterior plane) to ensure the proper placement of the total disc replacement system in the anterior-posterior plane. The surgeon may similarly align the row of anchor elements disposed along the lateral midline of the first and second anchor plates with the lateral midline of the first and second vertebral bodies and/or the associated spinous processes to ensure the proper placement of the total disc replacement system of the present invention in the lateral plane.

The total disc replacement system of the present invention may be introduced into a spinal target site through the use of any of a variety of suitable instruments having the capability to releasably engage the lateral TDR system. In association with this, the first anchor plate, second anchor plate and/or intradiscal element may be provided with at least one lumen, groove, and/or other mechanism for engagement with an insertion tool. In one embodiment, the insertion tool permits quick, direct, and accurate placement of the lateral TDR system into the intervertebral space. According to one embodiment, the insertion instrument includes a pair of prongs forming a cradle and an elongated inserter. The elongated inserter may have a locking element dimensioned to interact with the cradle so as to prevent the lateral TDR system from dislodging from the cradle during insertion. The cradle engages the lateral TDR system to facilitate insertion into the intervertebral space. Optionally, the cradle may further include side panels that are greater in height than that of the lateral TDR system, such that the vertebrae may be distracted by the cradle as the lateral TDR is being inserted into the intervertebral space.

The inserter may also optionally include notations (e.g. graphical indicia and/or text) on any suitable portion thereof (e.g. handle, elongated inserter, etc. . . . ) to inform the surgeon and/or support staff of the anterior-posterior (A-P) orientation of the lateral TDR system within the inserter. This is particularly important when the intradiscal element is off-axis between the anchor plates in the A-P plane to ensure the intradiscal element is positioned in the desired region within the disc space. or example, when it is desired to position the intradiscal element in the posterior region of the disc space, it is important to ensure that the surgeon and support staff know which way to orient the inserter (which has the intradiscal element disposed off-axis in the A-P plane between the anchor plates) such that the intradiscal element ends up in the posterior region of the disc space, as opposed to the anterior one-third of the disc space if introduced in the opposite A-P orientation. This may be accomplished, by way of example only, by etching or otherwise printing "Posterior" or "P" on the portion of the handle that corresponds to the posterior position of the intradiscal element when disposed between the anchor plates within the inserter. To assist in this, the anchor plates may be configured such that they can only be engaged with the inserter in the proper A-P orientation, such as by manufacturing the anterior and posterior edges of the plates each having a unique engagement feature that corresponds to the respective anterior and posterior prongs or elements of the inserter. A push rod may be provided to facilitate removal of the lateral TDR system from the cradle upon insertion into a target disc space. As part of the insertion process, a variety of appropriate trial sizers may be used.

An alternative embodiment of the lateral TDR system of the present invention is provided and includes a pair of anchor plates, a pair of intradiscal inserts, and an intradiscal element. The first anchor plate has a first surface for engaging a first vertebra and a second surface opposite the first surface including a cutout region for engaging a first intradiscal insert. The second anchor plate has a first surface for engaging a second vertebra and a second surface opposite the first surface including a cutout region for engaging a second intradiscal insert. The first intradiscal insert has a first surface for engaging with the first anchor plate, a second articular surface having a generally arcuate cross-section, and a measurable thickness therebetween. The second intradiscal insert has a first surface for engaging with the second anchor plate, a second generally planar surface for interaction with the intradiscal element, and a measurable thickness therebetween. The intradiscal element generally includes a pivot and a pin. The pivot includes a first articular surface for articulation with the second articular surface of the first intradiscal insert and a second generally planar surface for engaging with the second intradiscal insert. The pin may include a flat head region and an elongated shaft region, and is dimensioned to moveably secure the pivot to the second intradiscal insert and second anchor plate. The first anchor plate, second anchor plate, first and second intradiscal inserts, and/or intradiscal element may be constructed from any number of suitable materials, including but not limited to metal, ceramic, polymer, and/or any combination thereof.

The first surface of the first intradiscal insert is dimensioned in such a way to fit snugly within the cutout region of the first anchor plate such that the first intradiscal insert does not move (either by rotation or lateral translation) relative to the first anchor plate. Similarly, the first surface of the second intradiscal insert is dimensioned in such a way to fit snugly within the cutout region of the second anchor plate such that the second intradiscal insert does not move (either by rotation or lateral translation) relative to the second anchor plate. The first articular surface is dimensioned to articulate with the articular surface of the first intradiscal insert, and by extension the first anchor plate, such that the first anchor plate may rotate relative to the intradiscal element about an axis (e.g. X-axis, Z-axis, or any such axis defined by a line within the XZ plane that intersects the Y-axis). The second generally planar surface is dimensioned to interact with the second generally planar surface of the second intradiscal insert, and by extension the second anchor plate, such that the second anchor plate may rotate relative to the intradiscal element about a second axis (e.g., Y-axis). In this fashion, rotation about the first axis will always occur at the same location along the first anchor plate and rotation about the second axis will always occur at the same location along the second anchor plate.

The retaining pin includes a shaped head region and an elongated member. The head region may be generally circular in shape and is dimensioned to interact with the cutout region of the pivot, such that the head region prevents the pivot from exceeding a desired range of motion once the retaining pin has been secured to the second intradiscal insert. The elongated member extends in a generally perpendicular manner from the head region and is dimensioned to traverse a central aperture in the pivot and an aperture on the second intradiscal insert, and couple with an aperture on the second anchor plate. The diameter of the central aperture on the pivot may be substantially greater than the diameter of elongated member. These differences in diameters, along with the difference in diameters between the head region of the retaining pin and the cutout region of the pivot, function to allow for translation of the first anchor plate along any axis in the XZ plane, with the actual difference in diameter providing a limit on the degree of translation allowed. In use, then, the lateral TDR system of this first embodiment provides rotation along a plurality of axes (any axis in the XZ plane, and the Y-axis) and translation along a plurality of axes (any axis in the XZ plane). At least a portion of the distal region of elongated member may be threaded to engage with a threaded aperture on the second anchor plate to provide for increased stability to the lateral TDR system of the present invention.

The first and second anchor plates may each include a plurality of anchor elements for anchoring the lateral TDR device of the present invention to adjacent vertebrae. The anchor elements may include a plurality of protrusions having a cross-section comprising any number of suitable shapes, including but not limited to generally triangular. In one aspect, the anchor elements may be oriented such that the first and second anchor plates may be introduced in a generally lateral approach relative to the first and second vertebrae. In another aspect, the anchor elements may be oriented such that the first and second anchor plates may be introduced in a generally anterior approach relative to the first and second vertebrae. In yet another aspect, the anchor elements may be aligned along a longitudinal midline in one direction and along a lateral midline in another direction. Anchor elements aligned in such a matter may be used as guide members during implant insertion, ensuring proper positioning of the lateral TDR device, as described above. The first anchor plate, second anchor plate, first and second intradiscal inserts, and/or intradiscal element may be provided with at least one lumen, groove, and/or other mechanism for engagement with an insertion tool, as described above.

An alternative embodiment of the insertion instrument includes a cradle and an elongated inserter. The elongated inserter has a threaded engagement element dimensioned to threadedly engage into a receiving aperture formed in the cradle of the present invention. The cradle engages the lateral TDR system to facilitate insertion into the intervertebral space. The cradle further includes side panels that are greater in height than that of the lateral TDR system, such that the vertebrae may be distracted by the cradle as the lateral TDR is being inserted into the intervertebral space. As such, the insertion tool of the present invention exhibits self-distraction capabilities.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 73 is a perspective view of an insertion cradle forming part of the insertion tool of FIG. 72;

FIG. 74 is a front view of the insertion cradle of FIG. 73;

FIG. 75 is a front view of a lateral TDR system coupled to the insertion cradle of FIG. 73;

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The total disc replacement system and related methods disclosed herein boasts a variety of inventive features and components that warrant patent protection, both individually and in combination.

Figure 1:
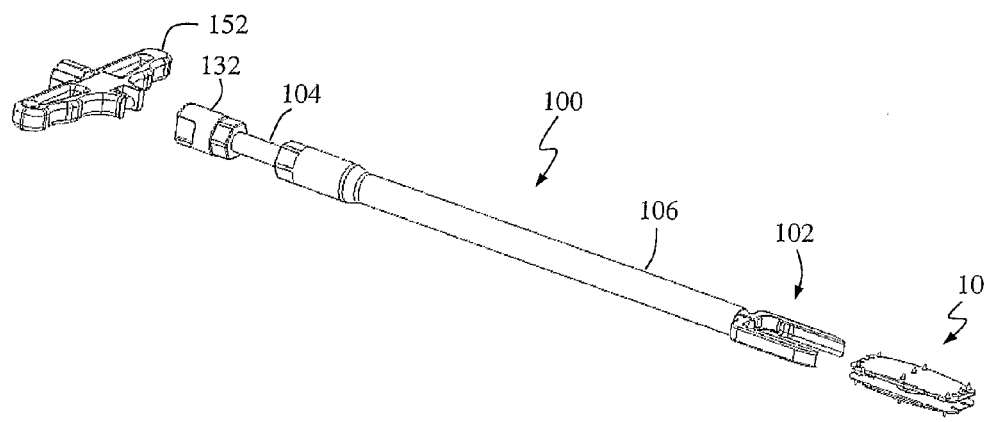
FIG. 1 is a perspective view of an example of a lateral total disc replacement (TDR) system and inserter according to a first embodiment of the present invention.

FIG. 1 illustrates an example of a lateral total disc replacement (TDR) system 10 according to a first embodiment of the present invention and an example of an insertion tool 100 (including a T-handle assembly 152) used to insert the lateral TDR system 10 into an intervertebral space of a spine. The lateral TDR system 10 disclosed herein (as well as alternative embodiments thereof) is dimensioned for lateral insertion into the intervertebral space using minimally invasive techniques, such shown and described in commonly owned and co-pending International Patent Application No. PCT/US2004/031768, entitled "Surgical Access System and Related Methods" (filed Sep. 27, 2004, claiming priority from U.S. Provisional Patent Application Ser. Nos. 60/506,136 filed Sep. 25, 2003) (the '768 PCT), the entire content of which is hereby expressly incorporated into this disclosure as if set forth fully herein. The '768 PCT describes a neurophysiology-based surgical access system whereby an operative corridor may be established to a spinal target site in a generally lateral manner such that an implant may be introduced into the lateral aspect (side) of the surgical target site (e.g. disc space). As described in the '768 PCT, the lateral approach is preferably retroperitoneal and trans-psoas, the latter of which is aided via the use of intra-operative neural monitoring (continuous and/or intermittent) to ensure nerves within or adjacent to the psoas muscle are not impinged upon and/or damaged during the step of establishing the operative corridor through the psoas muscle.

The insertion tool 100 is provided with a distal engagement region 102 adapted to securely engage the lateral TDR system 10 during insertion and to further allow for a simple, safe and effective disengagement once the lateral TDR system 10 is implanted. Referring to FIGS. 2-8, the lateral TDR system 10 includes a first anchor plate 12, a second anchor plate 14, and an intradiscal element 16. In the example described herein, the lateral TDR system 10 is adapted for minimally invasive lateral insertion into an intervertebral space. As such, each anchor plate 12, 14 is generally rectangular in shape, having a length dimension (defined by a distance along an "X" axis) greater than a width dimension (defined by a distance along a "Z" axis). The lateral TDR system 10 of the present invention may be provided with varying length, width, and height dimensions depending on the position within the spine of the target intervertebral disc space, as well as individual patient anatomies. By way of example only, the lateral TDR system 10 may be provided having dimensions falling within the ranges of 40-55 mm in length, 18-22 mm in width, and 8-14 mm in height. In a preferred embodiment, the lateral TDR implant size should be selected such that at least one and preferably more than one anti-migration feature provided thereon rests on the hard cortical ring, thereby reducing the possibility of subsidence through the vertebral endplates. Furthermore, the lateral TDR system 10 of the present invention may be provided with first and second anchor plates 12, 14 having a shape other than generally rectangular, including by way of example only generally circular, generally elliptical and/or generally curved. Such alternative shapes may be provided for other surgical techniques (e.g. open procedures) and/or approaches (e.g. anterior, posterior, antero-lateral and postero-lateral).

Figure 2:
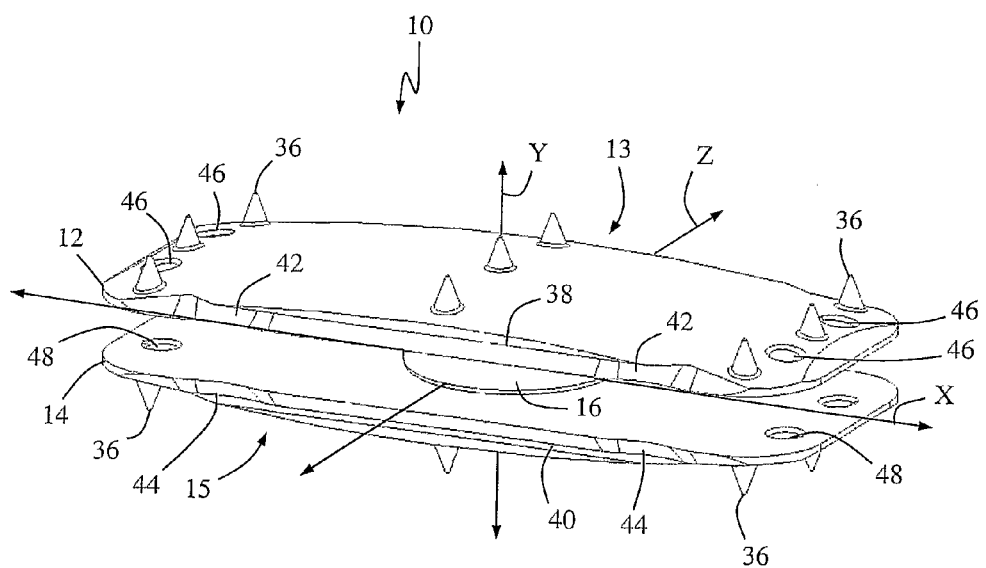
FIG. 2 is a perspective view of an assembled lateral TDR system according to a first embodiment of the present invention.
Figure 3:
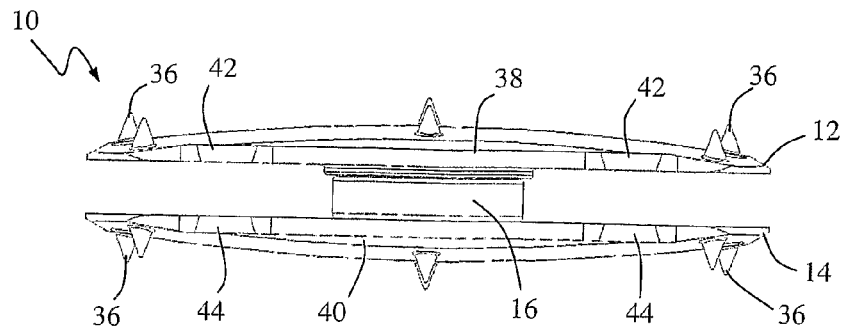
FIGS. 3-4 are side (anterior or posterior) and end (lateral) views, respectively, of the lateral TDR system of FIG. 2.
Figure 4:
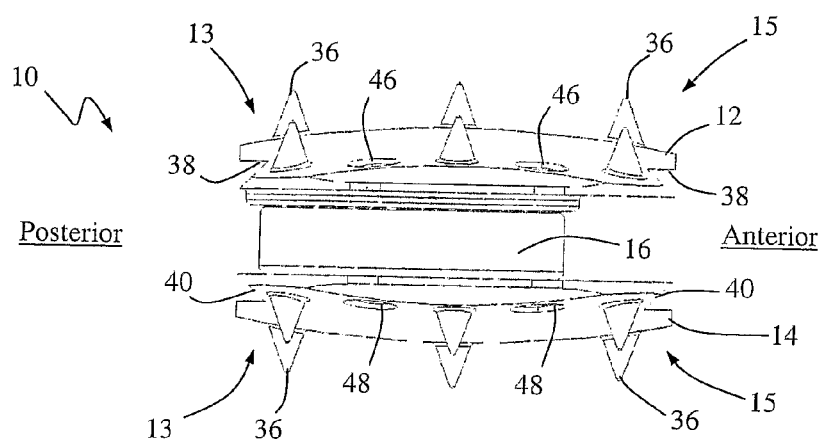
Figure 5:
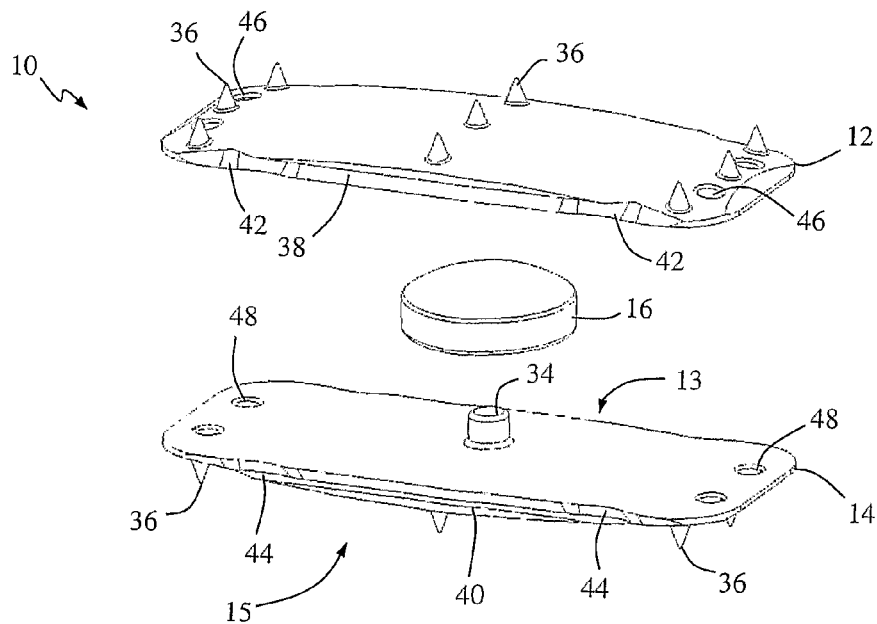
FIGS. 5-6 are exploded top and bottom perspective views, respectively, of the lateral TDR system of FIG. 2.
Figure 6:
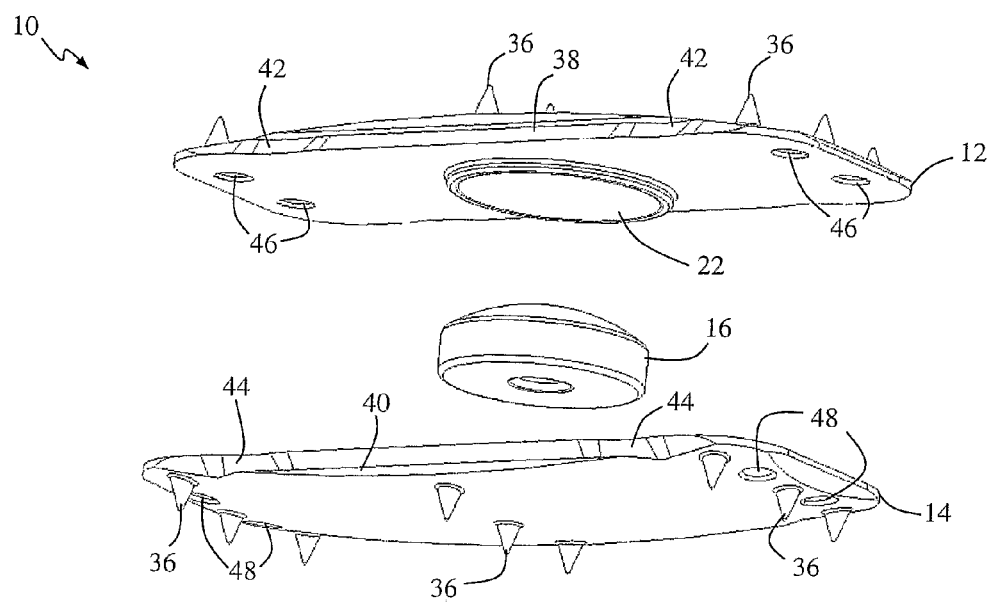
Figure 7:
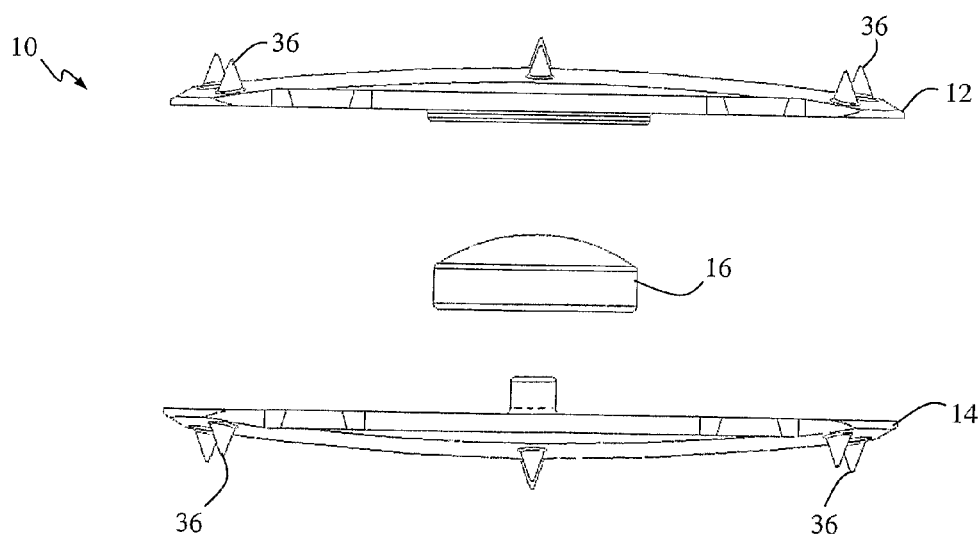
FIGS. 7-8 are exploded side (anterior or posterior) and end (lateral) views, respectively, of the lateral TDR system of FIG. 2.
Figure 8:
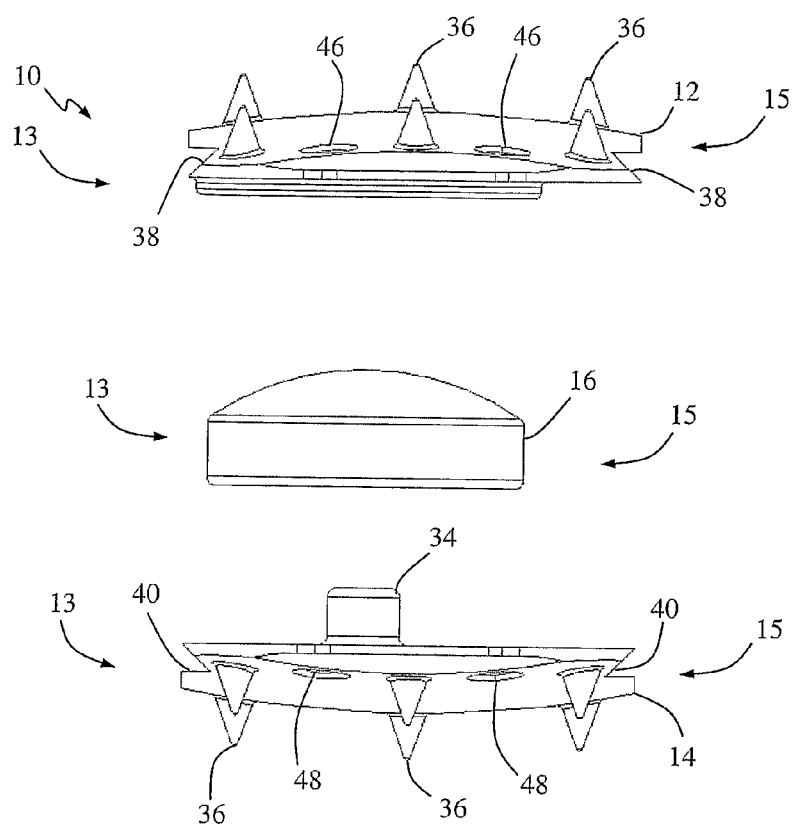
Figure 9:
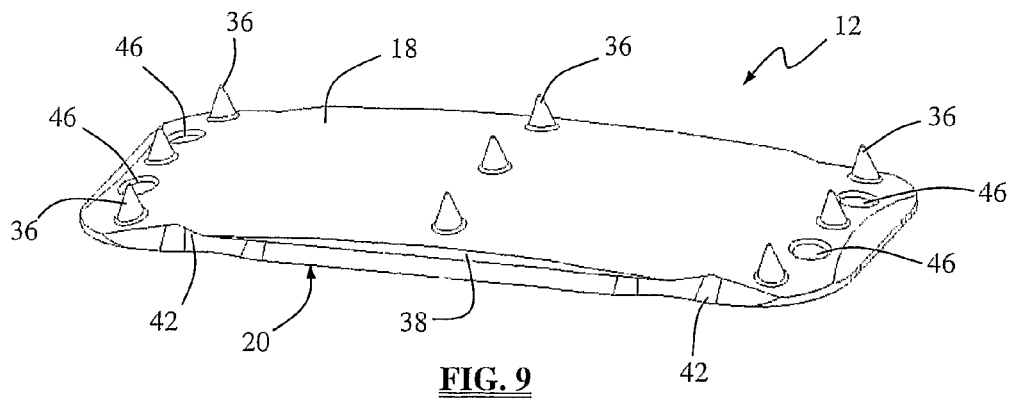
FIGS. 9-10 are top and bottom perspective views, respectively, of a first anchor plate forming part of the lateral TDR system of FIG. 2.
Figure 10:
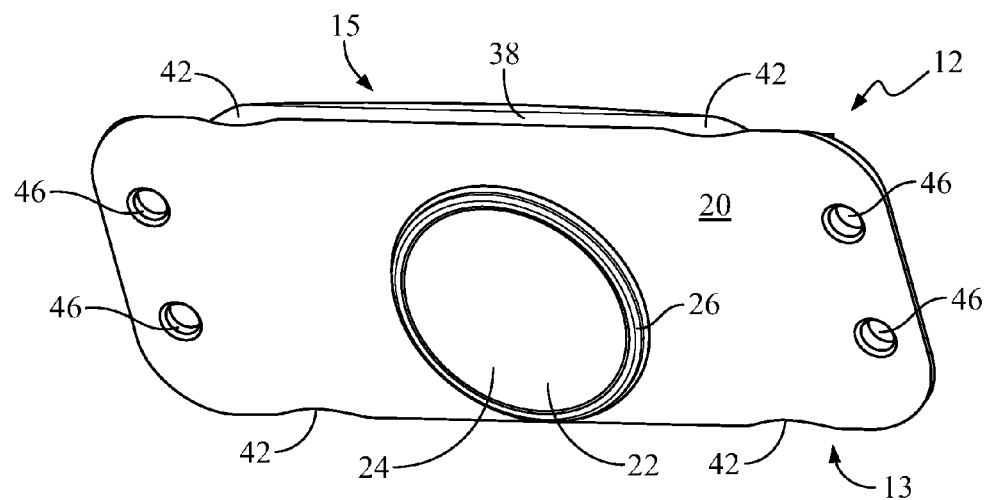
Figure 11:
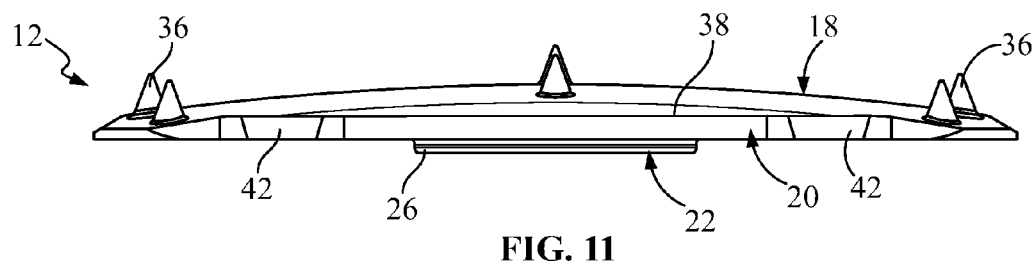
FIGS. 11-12 are side (anterior or posterior) and end (lateral) views, respectively, of the first anchor plate forming part of the lateral TDR system of FIG. 2.
Figure 12:
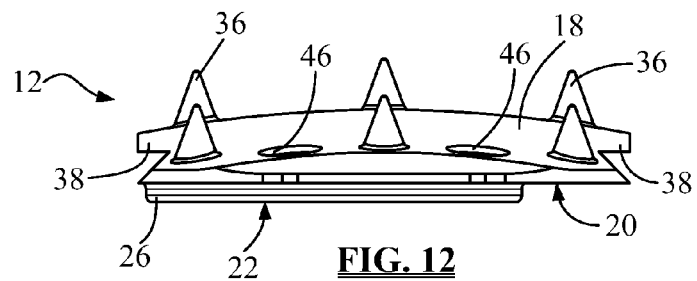
Figure 13:
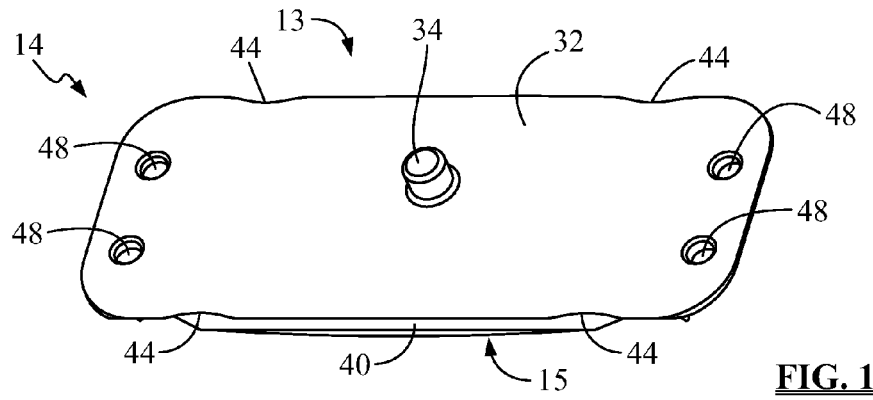
FIGS. 13-14 are top and bottom perspective views, respectively, of a second anchor plate forming part of the lateral TDR system of FIG. 2.
Figure 14:
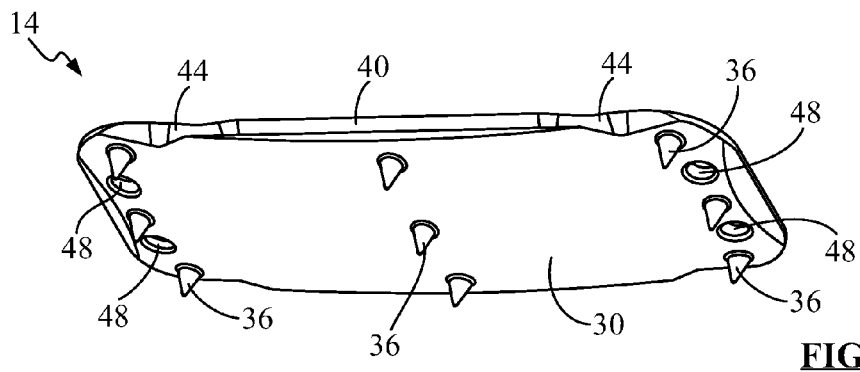
Figure 15:
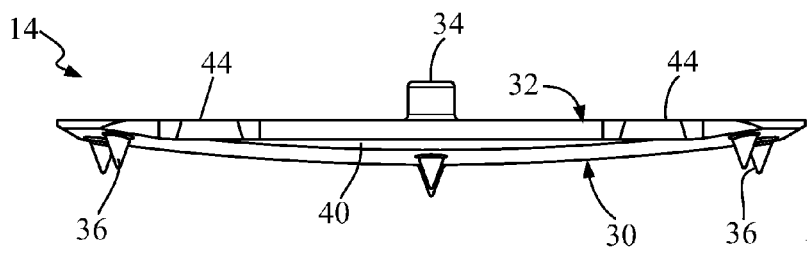
FIGS. 15-16 are side (anterior or posterior) and end (lateral) views, respectively, of the second anchor plate forming part of the lateral TDR system of FIG. 2.
Figure 16:
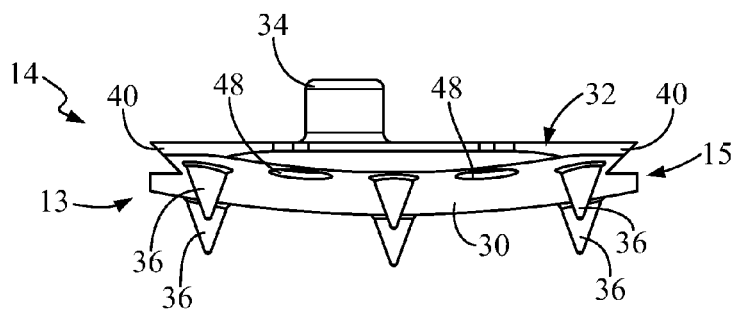
Figure 17:
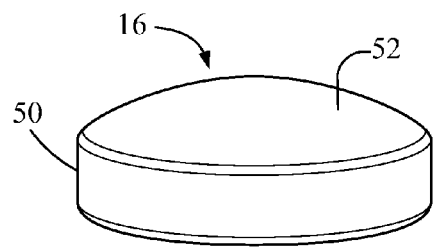
FIGS. 17-19 are top perspective, side (lateral), and bottom perspective views, respectively, of an intradiscal element forming part of the lateral TDR system of FIG. 2.
Figure 18:
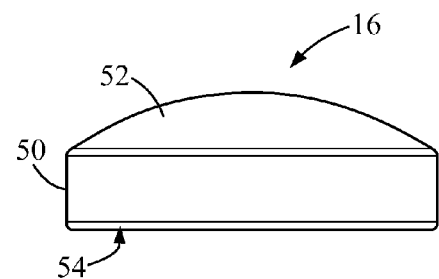
Figure 19:
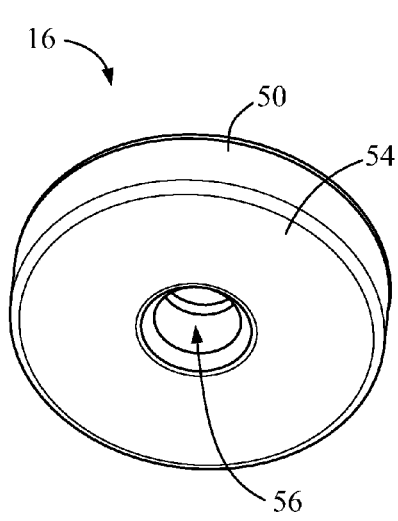

The intradiscal element 16 may be positioned in any number of suitable locations relative to the first anchor plate 12 and second anchor plate 14, such as (by way of example only) off-center from an X-axis (as shown in FIG. 2) such that the intradiscal element 16 is disposed in the posterior region (e.g. in the posterior one-third) of the disc space when disposed in the lumbar spine. This ensures that the instantaneous axis of rotation of the lateral TDR system 10 will be disposed in the posterior region (e.g. in the posterior one-third) of the disc space, which is believed to be the proper intervertebral position for optimum motion preservation performance. This is evident with reference to FIGS. 4 & 47. According to one aspect of the present invention, providing the intradiscal element 16 in this "automatically posterior" positions is advantageous in that it allows for a simplified insertion process in that when a surgeon inserts the lateral TDR system 10 into the middle of the intradiscal space, the intradiscal element 16 will automatically be placed in the posterior region of the disc space. This, as will be appreciated, increases the efficiency of the procedure and ensures proper placement of the lateral TDR system 10, which decreases the amount of time required for the operation. As a result of this posterior placement of the intradiscal element 16, the first and second anchor plates 12, 14 can each be defined as having a posterior side 13 and an anterior side 15.

FIGS. 9-12 detail the first anchor plate 12, which includes a first surface 18 for engaging a first vertebra and a generally planar second surface 20 opposite said first surface 18. A recess 22 may be provided at the approximate midline or middle (relative to the X-axis) of the second surface 20. Preferably, the recess 22 includes a semi-spherical articular surface 24 dimensioned to receive at least a portion of the intradiscal element 16. As a result, the recess 22 is positioned towards the posterior side 13 of the first anchor plate 12 in order to accommodate the posterior bias of the intradiscal element 16. The recess 22 interacts with the intradiscal element 16 to allow for translational and/or rotational movement of the first anchor plate 12 relative to the second anchor plate 14. Optionally, the second surface 20 may include a raised perimeter 26 around the recess 22 to increase the surface area of the partially spherical articular surface without impacting the overall profile of the lateral TDR system 10.

FIGS. 13-16 detail the second anchor plate 14, which includes a first surface 30 for engaging a second vertebra and a generally planar second surface 32 opposite said first surface 30. The second anchor plate 14 further includes a post element 34 provided at the approximate midline (i.e. along the Z-axis) of the second surface 32. In the example as shown, the post element 34 is provided in a posteriorly-biased offset orientation (e.g. toward posterior side 13) to accommodate the posterior bias of the intradiscal element 16. However, in some instances it may be advantageous to provide the post element 34 at the intersection of the X and Z axes, in the center of the second anchor plate 14. In any event, the post element 34 should have a placement on the second anchor plate 14 generally opposite the recess 22 located on the first anchor plate 12. The post element 34 may be generally cylindrical in shape and dimensioned to be received within a central bore 46 of the intradiscal element 16 (described in further detail below).

A plurality of anti-migration features 36 may be provided on the first and second anchor plates 12, 14 to inhibit the movement of the plates after introduction into an intervertebral space. In one embodiment, the anti-migration features 36 may comprise protrusions having a generally triangular cross-section, although any number of suitable configurations or anti-migration elements may be employed without departing from the scope of the present invention. Although the anti-migration features 36 may be provided in any number or arrangement, it is preferable to include at least three anti-migration features 36 arranged along a longitudinal midline (i.e. co-linear with the X-axis) and at least three anti-migration features 36 arranged along a lateral midline (i.e. co-linear with the Z-axis) of the lateral TDR system 10, as best shown by way of example in FIGS. 2-5. This arrangement will enable more accurate and efficient placement of the lateral TDR system 10 within the intervertebral space. More specifically, the longitudinally aligned anti-migration features may be used as a guide while inserting the lateral TDR system 10 from a lateral direction to ensure proper placement relative to the anterior and posterior portions of the spine. The laterally aligned anti-migration features may be used as a guide to confirm proper placement by ensuring these anti-migration features are in line with the middle of the vertebral bodies (from an anterior view) and/or spinous process. This ensures that the lateral TDR system 10 is in proper positioning relative to the lateral sides of the spine.

Any number of mechanisms or techniques may be employed to introduce the first and second anchor plates 12, 14 into an intervertebral space, including but not limited to providing a first pair of grooves 38 located on either side and traversing the length of the first anchor plate 12 and a second pair of groves 40 located on either side and traversing the length of the second anchor plate 14. Optionally, at least one recess 42 is provided within each groove 38 near an end of the first anchor plate 12. Preferably, a pair of recesses 42 are provided within each groove 38, with one recess 42 located near each end of the first anchor plate 12. Similarly, at least one recess 44 is provided within each groove 40 near an end of the second anchor plate 14. Preferably, a pair of recesses 44 are provided within each groove 40, with one recess 44 located near each end of the second anchor plate 14. Recesses 42, 44 are dimensioned to interact with the lateral TDR insertion tool 100 to provide a "snap-fit" engagement between the lateral TDR system 10 and the insertion tool 100, described in further detail below. A plurality of apertures 46 extending through the first anchor plate 12 from the first surface 18 to the second surface 20 may be provided for facilitating engagement between an insertion or removal tool (not shown) and the first anchor plate 12. Similarly, a plurality of apertures 48 extending through the second anchor plate 14 from the first surface 30 to the second surface 32 may be provided for facilitating engagement between an insertion instrument or removal tool (not shown) and the second anchor plate 14.

The first and second anchor plates 12, 14 may be constructed from any number of materials and/or compositions suitable for medical applications, including but not limited to metallic compositions (such as titanium) or alloys (such as Co—Cr—Mo), ceramics (such as zirconia and/or alumina), polymers (such as ultra-high molecular weight polyethylene), and/or any combination thereof. Where beneficial and appropriate, either or both of the first and second anchor plates 12, 14 may also be coated with any number of suitable compositions, such as zirconium oxide coating found in U.S. Pat. No. 5,037,438, the contents of which are hereby incorporated into this disclosure as if set forth in its entirety.

FIGS. 17-20 detail the intradiscal element 16, which may be provided as a single piece having a generally cylindrical base 50, a first articular surface 52 and a second generally planar surface 54 opposite said first articular surface 52. Although shown and described as generally cylindrical in shape, the intradiscal element 16 may comprise any shape that allows for a complete range of motion, including but not limited to circular, oval, square, and rectangular. The first articular surface 52 is dimensioned to articulate with semi-spherical articular surface 21 of the recess 22 of the first anchor plate 12 such that the first anchor plate 12 may freely rotate relative to the intradiscal element 16 about any axis defined by a line within the XZ plane that intersects the Y-axis (or an axis parallel thereto when the post element 34 is posteriorly biased). The second generally planar surface 54 is dimensioned to interact with the second generally planar surface 32 of the second anchor plate 14 such that the second anchor plate 14 may freely rotate relative to the intradiscal element 16 about the Y-axis. In this fashion, rotation about any axis in the XZ plane will always occur at the same location along the first anchor plate 12 and rotation about the Y-axis will always occur at the same location along the second anchor plate 14.

Figure 20:
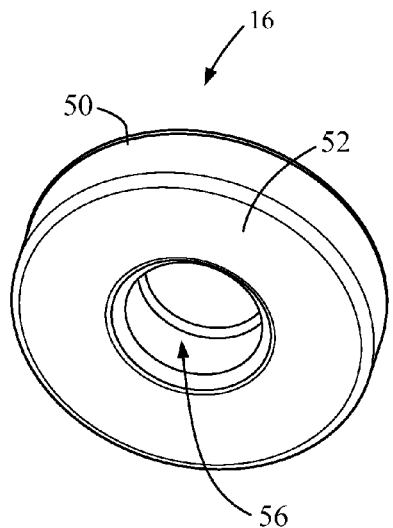
FIG. 20 is a bottom perspective view of an alternative embodiment of the intradiscal element forming part of the lateral TDR system of FIG. 2.
Figure 21:
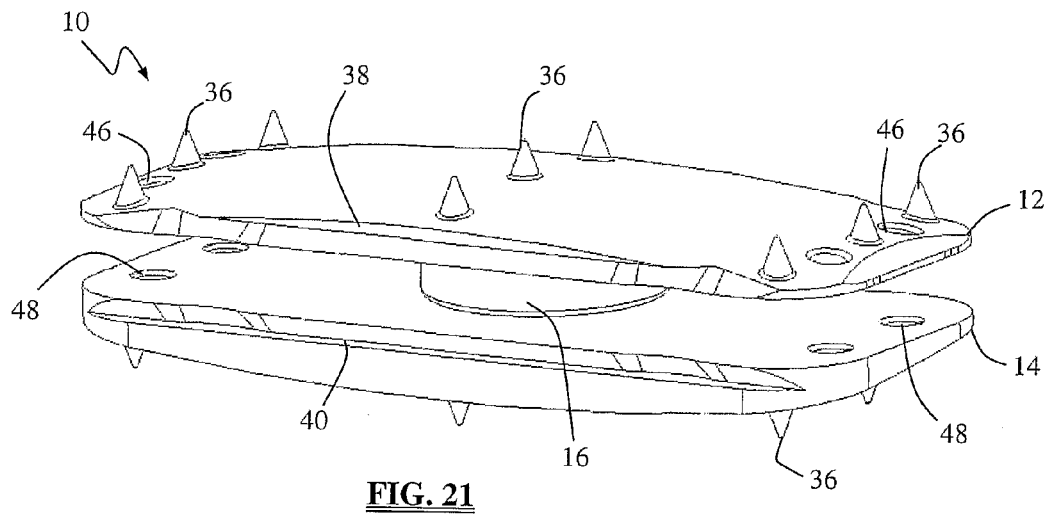
FIGS. 21-22 are perspective and end views, respectively, of an example of a lateral TDR system according to a second embodiment of the present invention, wherein a second anchor plate has an angled cross-section to force the adjacent vertebral bodies into a predetermined position upon implantation (e.g. lordosis in lumbar spine and kyphosis in the thoracic spine)

The second generally planar surface 54 includes a central bore 56 dimensioned to receive the post element 34 of the second anchor plate 14. Central bore 56 may be generally circular in shape, and have any diameter necessary to allow for an optimal range of translation of the intradiscal element 16, which may vary between different embodiments of the total disc replacement system 10 and depend on the desired destination of the implant (e.g. lumbar, thoracic, and cervical spine). For example, the intradiscal element 16 shown in FIG. 19 includes a central bore 56 having a diameter only marginally greater than the diameter of the post element 34 so as to allow coupling of the post element 34 with the bore 56. This arrangement prevents translation of the intradiscal element 16 in the XZ plane but allows for axial rotation about the Y-axis (or an axis parallel thereto). Alternatively, the intradiscal element 16 as shown in FIG. 20 includes a central bore 56 having a diameter that is greater than the outer diameter of the post element 34. This allows for translation of the intradiscal element 16 in any direction in the XZ plane as well as for axial rotation about the Y-axis (or an axis parallel thereto). Alternatively, the intradiscal element 16 may be pre-attached, molded, or otherwise integrated in a fixed relationship to the second anchor plate 14.

It will be understood that although the lateral TDR system 10 has been described as allowing for free rotation/translation of the first and second anchor plates 12, 14 the extent of such rotation/translation will be constrained only by the natural limitations of the human body (muscles, ligaments, spinal structure, etc). Thus, the lateral TDR system 10 of the present invention allows the spine to retain its full range of motion with respect to flexion, extension, and lateral bending. Similarly, rotation about the Y-axis as described above allows for full retention of the spine's axial rotation abilities. Thus, the lateral TDR system 10 of the present invention provides for complete motion retention capabilities of a normal human spine.

When used within the lumbar spine, for example, it may be desirable to configure the second anchor plate 14 such that the post element 34 is located within the posterior one-third of the disc space (and generally within the frontal plane of the patient) to approximate the axis of rotation of the natural spine during flexion and extension. It may similarly be desirable to configure the first anchor plate 12 such that the recess 22 is located at the approximate center of the disc space (and generally within the sagittal plane of the patient) to approximate the axis of rotation of the natural spine during lateral bending. Although described by way of example in this configuration, it will be appreciated that the relative position of the recess 22 and post element 34 may be altered in any number of different fashions depending upon the vertebral level (i.e. cervical, thoracic, and/or lumbar) as well as the directional approach employed to place the lateral TDR system 10 into a disc space (e.g., lateral, anterior, postero-lateral, antero-lateral). Moreover, it will be appreciated that the lateral TDR system 10 may be introduced into a disc space in the orientation shown (with the first anchor plate 12 "above" the second anchor plate 14 such that the anti-migration features 36 are to be disposed within a respective "upper" and "lower" vertebral level within the patient) or vice versa.

The intradiscal element 16 may be constructed from any number of materials and/or compositions suitable for medical applications, including but not limited to metallic compositions or alloys (such as Co—Cr—Mo), ceramics (such as zirconia and/or alumina), polymers (such as ultra-high molecular weight polyethylene), and/or any combination thereof. Where beneficial and appropriate, the intradiscal element 16 may also be coated with any number of suitable compositions, such as the zirconium oxide coating mentioned above.

Figure 22:
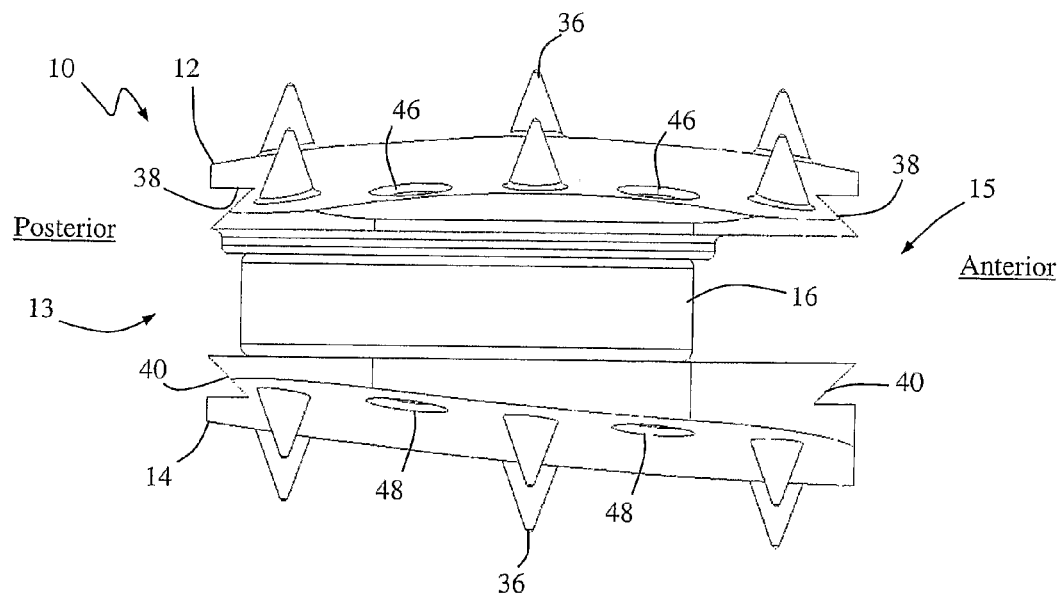
Figure 23:
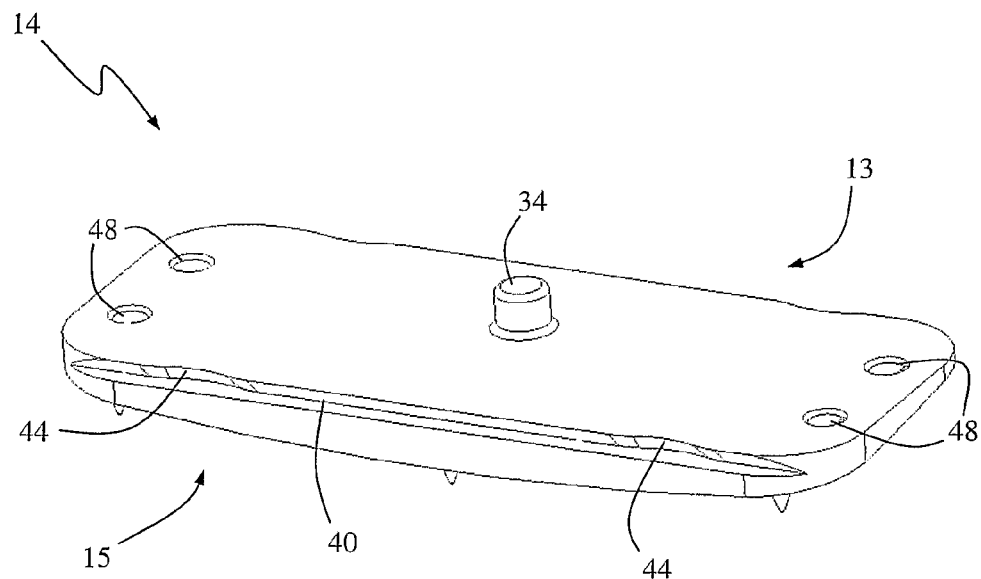
FIGS. 23-24 are top perspective and end (lateral) views, respectively, of the second anchor plate forming part of the lateral TDR system of FIG. 21.
Figure 24:
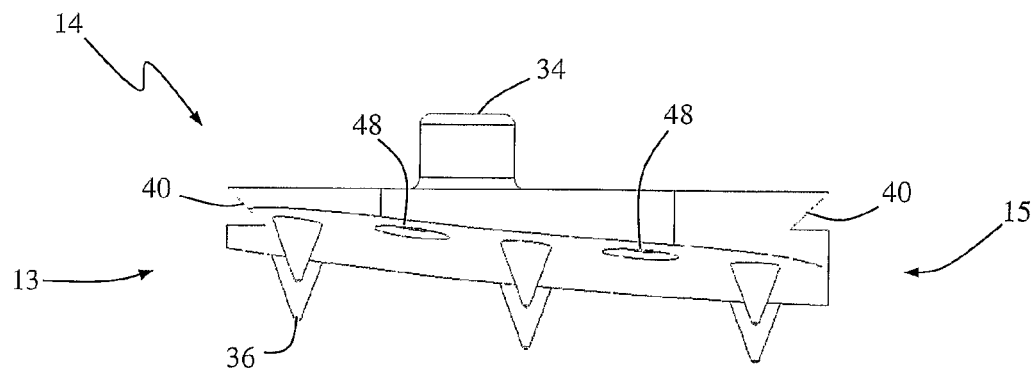
Figure 25:
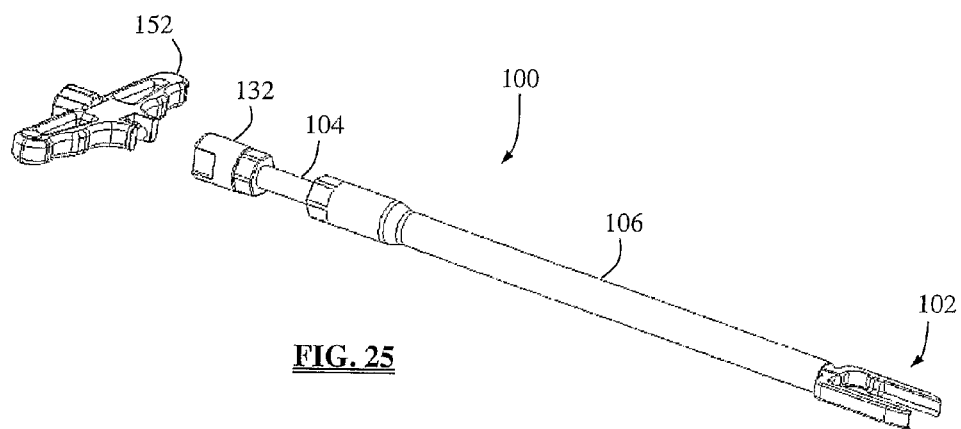
FIGS. 25-26 are perspective views of the entire inserter of FIG. 1 and the distal end of the inserter of FIG. 1, respectively.
Figure 26:
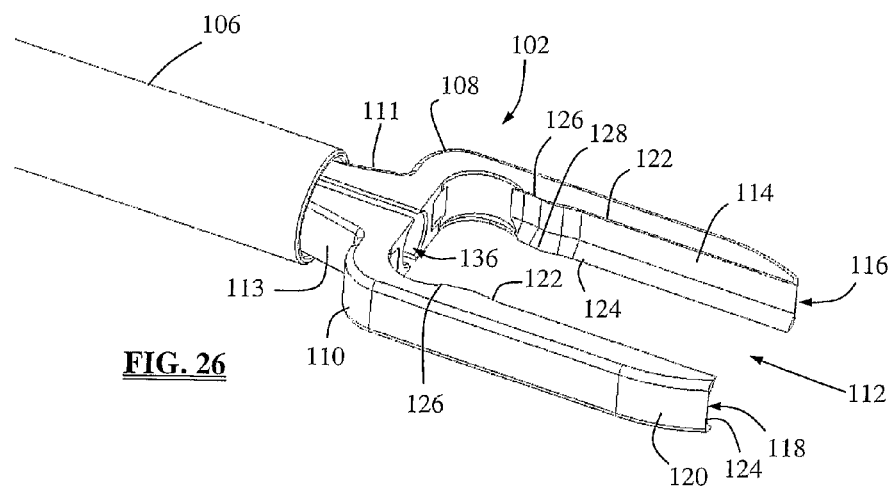

FIGS. 21-24 illustrate an alternate embodiment of the lateral TDR system 10 of the present invention, adapted (by way of example only) for placement within a lordotic region of the spine (e.g. lumbar region). This is accomplished, as best shown in FIGS. 22 and 24, by providing the second anchor plate 14 with an asymmetrical or angled cross-sectional thickness in the anterior-posterior (A-P) plane (i.e. along the Z-axis). More specifically, the second anchor plate 14 has an anterior side 15 that is thicker than the posterior side 13. This configuration allows the lateral TDR system 10 to effectively engage the vertebrae by accounting for the natural curvature of the lumbar spine. Although shown in the lordotic manner in this example, it will be appreciated by those skilled in the art that one or more of the anchor plates 12, 14 may be similarly dimensioned to force the adjacent vertebral bodies of the thoracic spine into kyphosis and that this is contemplated as part of the present invention.

In a preferred embodiment, the lateral TDR system 10 may be provided in one or more surgical kits offering implants of varying dimensions. In this manner, the size (e.g. length, width, and height) of the implant may be determined during the surgical procedure (for example, by using the trail sizers 190 described below) when it may best be assessed. Table 1 below, set forth by way of example only, illustrates the dimensions of endplates 12, 14, both regular and lordotic, available in one exemplary kit. Although set forth below having a lordotic angle of 5 degrees, it will be appreciated that the angle of lordosis may be provided in any number of suitable angles without departing from the scope of the present invention, including but not limited to 1 degree to 15 degrees.

the present invention is not limited to interaction with the lateral TDR systems disclosed herein, but rather may be dimensioned to engage any laterally-inserted TDR system. The insertion tool 100 of the present invention includes a distal engagement region 102, an elongated shaft 104, a tubular lock member 106, a proximal attachment member 132 and a removable T-handle assembly 152 provided in accordance with a first embodiment of the present invention. By way of example only, the insertion tool 100 is similar to the inserter shown and described in commonly owned U.S. Pat. No. 6,923,814 entitled "System and Method for Cervical Spinal Fusion," which is hereby incorporated by reference into this disclosure as if set forth fully herein. Alternatively, the insertion tool may include a cradle member threadedly engaged with an elongated inserter, as described below.

FIGS. 26-29 detail the distal engagement region 102, which is positioned at the distal end of elongated shaft 104 and consists of a pair of clamping arms 107, 109, each including a generally "L"-shaped prong 108, 110, respectively. The prongs 108, 110 are coupled with the clamping arms 107, 109 so that the prongs 108, 110 are restrained from movement relative to the clamping arms 107, 109. The clamping arms 107, 109 are generally parallel and spaced apart from one another when in a freestanding configuration. The prongs 108, 110 are oriented such that each respective "L" shape faces one another, thereby forming a cradle 112 for engagement with the lateral TDR system 10.

TABLE 1

Lateral TDR Implants
WIDTH (Z-Axis) 18 mm; 20 mm; 22 mm

| LENGTH (X-axis) | HEIGHT (Y-axis) | | | | | | |
|---|---|---|---|---|---|---|---|
| | 8 mm | 9 mm | 10 mm | 11 mm | 12 mm | 13 mm | 14 mm |
| First Anchor Plate 12 | | | | | | | |
| 40 mm | X | X | X | X | X | X | X |
| 45 mm | X | X | X | X | X | X | X |
| 50 mm | X | X | X | X | X | X | X |
| 55 mm | X | X | X | X | X | X | X |
| Second Anchor Plate 14 | | | | | | | |
| 40 mm | X | X | X | X | X | X | X |
| 45 mm | X | X | X | X | X | X | X |
| 50 mm | X | X | X | X | X | X | X |
| 55 mm | X | X | X | X | X | X | X |
| Lordotic Second Anchor Plates 14 | | | | | | | |
| 5° Lordosis  40 mm | X | X | X | X | X | X | X |
| 5° Lordosis  45 mm | X | X | X | X | X | X | X |
| 5° Lordosis  50 mm | X | X | X | X | X | X | X |
| 5° Lordosis  55 mm | X | X | X | X | X | X | X |

FIGS. 25-31 illustrate an example of an insertion tool 100 for inserting a lateral TDR system 10 into a prepared intervertebral space according to one embodiment of the present invention. The insertion tool 100 is configured to releasably maintain the lateral TDR system 10 in the proper orientation during lateral insertion into an intervertebral disc space and thereafter release the lateral TDR system 10 upon successful placement. The lateral TDR system 10, having been deposited in the intervertebral space, facilitates normal spinal functionality over time by maintaining a restored disc height (due to the structural and load-bearing capabilities of the lateral TDR system 10) as well as retaining a normal range of motion. Although shown by way of example only coupled to a TDR system 10 as described above, the insertion tool 100 of Immediately proximal from the cradle 112, each clamping arm 107, 109 includes a tapered surface 111, 113, respectively, in which the larger dimension is oriented closest to the cradle 112 and the smaller dimension is oriented closest to the elongated shaft 104. Proximal to taper features 111, 113 the clamping arms 107, 109 become generally semi-cylindrical such that when viewed together the clamping arms 107, 109 have a generally cylindrical shape and a constant diameter approximately matching the smallest outer dimension of the taper features 111, 113. This constant diameter is maintained by the elongated shaft 104 proximal to the clamping arms 107, 109.

Preferably, the cradle 112 is generally rectangular in shape, but may take the form of any geometric shape necessary to interact with the lateral TDR system 10, including but not limited to generally oval, square, and triangular. The distal engagement region 102 may be composed of any material suitable for facilitating the insertion of a TDR system 10 into an intervertebral space, including but not limited to metal (e.g. titanium), ceramic, and/or polymer compositions. In a preferred embodiment shown and described herein, the cradle 112 engages the lateral TDR system 10 with a "snap-fit" engagement described below. Alternatively, the cradle 112 may engage the lateral TDR system 10 by any suitable means of engagement, including but not limited to a threaded engagement, hooks, and/or compressive force.

Prongs 108, 110 each have an inside surface 114, 118 and an outside surface 116, 120, respectively. Preferably, inside surfaces 114, 118 may be generally planar, but may have any configuration suitable for interaction with TDR system 10, including but not limited to generally planar, generally concave, and generally convex. Outside surfaces 116, 120 may have any configuration suitable for facilitating insertion of a TDR system 10 into a prepared intervertebral disc space, including but not limited to generally planar, generally concave, and generally convex (as shown in the figures by way of example only). Prongs 108, 110 each have a first engagement ridge 122 and a second engagement ridge 124 extending at least partially along the length of inside surfaces 114, 118. First engagement ridges 122 are dimensioned to be received within first grooves 38 on either side (posterior and anterior) of the first anchor plate 12 (shown and described above). Second engagement ridges 124 are dimensioned to be received within second grooves 40 on either side of second anchor plate 14. Optionally, first engagement ridges 122 may each further include one or more protrusions 126 situated near the proximal end of the ridge 122. Protrusions 126 are dimensioned to be received within recesses 42 on either side of first anchor plate 12. Similarly, second engagement ridges 124 may each further include one or more protrusions 128 situated near the proximal end of the ridge 124 and dimensioned to be received within recesses 44 on either side of second anchor plate 14. The interaction of protrusions 126, 128 with recesses 38, 40, respectively, create a "snap-fit" engagement between the lateral TDR system 10 and the inserter 100 such that the lateral TDR system 10 is effectively secured between prongs 108, 110 and enabling the lateral TDR system 10 to be either inserted into or removed from a disc space. Engagement of the lateral TDR system 10 to the inserter 100 according to the methods described herein make possible the simultaneous insertion of TDR system 10. In other words, the entire system 10 may be inserted into the targeted disc space in one insertion step as opposed to multiple insertion steps required to, essentially, build a construct within the disc space, as is required by some total disc replacement implants known in the art.

Figure 30:
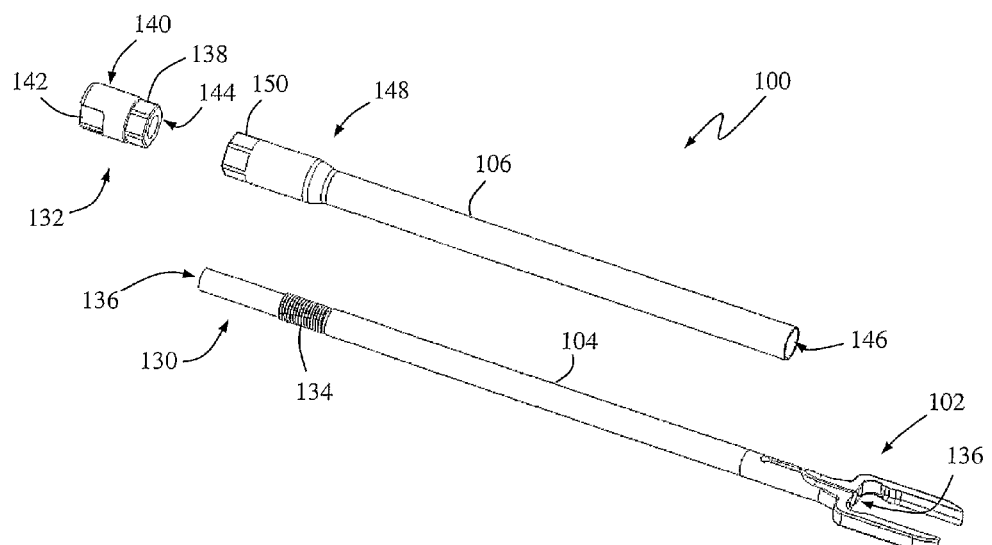
FIGS. 30-31 are exploded and assembled perspective views, respectively, of the inserter of FIG. 1 (without a T-handle for clarity)
Figure 31:
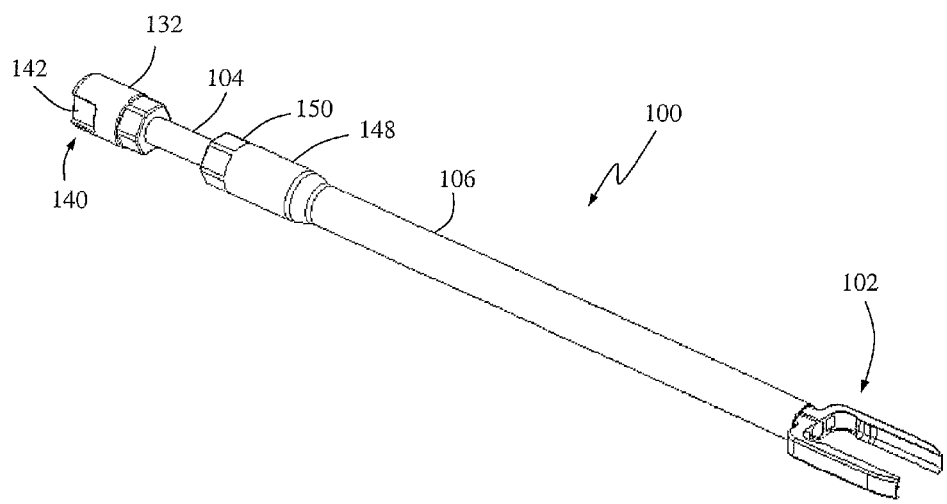

FIGS. 30-31 detail the elongated shaft 104, the tubular lock member 106, and the proximal attachment member 132 (with the T-handle assembly 152 removed). The elongated shaft 104 extends proximally from the distal engagement region 102 to a proximal end 130 to which the proximal attachment member 132 may be attached. The elongated shaft 104 is generally cylindrical and of a length sufficient to allow the device to span from the surgical target site to a location sufficiently outside the patient's body so to enable insertion of the lateral TDR system 10. Elongated shaft 104 may further included a threaded region 134 located near the proximal end 130. Threaded region 134 may be dimensioned to threadedly engage the proximal engagement region 148 of the tubular lock member 106, as described further below. The elongated shaft 104 may be provided with an interior lumen 136 extending therethrough. The proximal attachment member 132 is generally cylindrical in shape and is dimensioned to be attached to the proximal end 130 of the elongated shaft 104. The proximal attachment member 132 may be provided with a generally hexagonal-shaped tool engagement region 138 at its distal end and a T-handle engagement region 140 at its proximal end. In the example shown in FIG. 30 (among others), the T-handle engagement region 140 is provided as a pair of recesses 142 dimensioned to receive attachment flanges 164 of the T-handle assembly 152, thus facilitating the attachment of the T-handle assembly 152 to the elongated rod 104. However the T-handle engagement region may have any shape or configuration complementary to the shape and configuration of the attachment flanges 164. The proximal attachment member 132 is further provided with a lumen 144 extending therethrough dimensioned to receive (at least at a distal end) the proximal end 130 of the elongated shaft 104. Lumens 136, 144 are dimensioned to be contiguous such that an instrument such as a push rod 180 may traverse the length of the elongated shaft and engage the lateral TDR system 10. The proximal attachment member 132 may be permanently mated to the elongated shaft 104 or may be removable. Lumen 144 may further include a threaded region (not shown) at its distal end to interact with the T-handle assembly 152 as described below.

Figure 27:
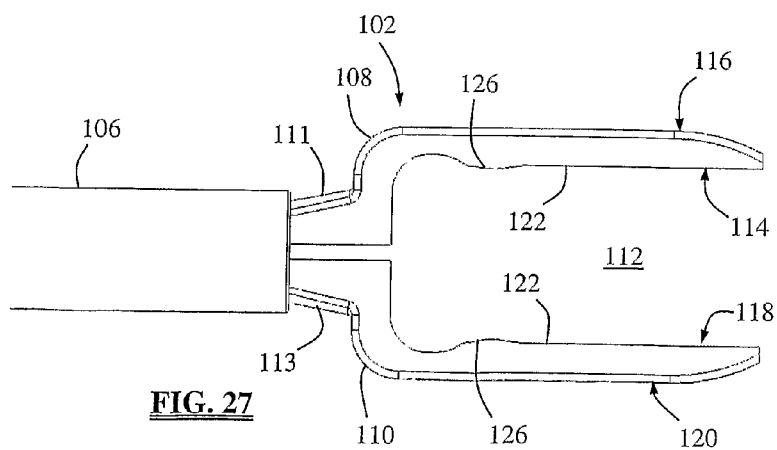
FIG. 27 is a top view of the distal end of the inserter of FIG. 1.
Figure 28:
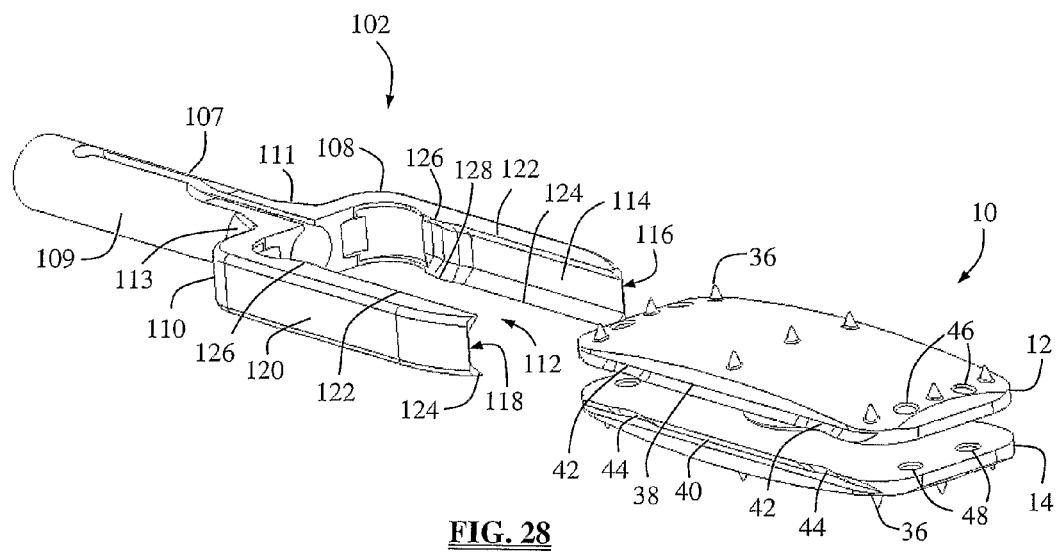
FIG. 28 is a perspective view of the distal engagement region of the insertion tool of FIG. 26 positioned to receive a lateral TDR system of FIG. 2.
Figure 29:
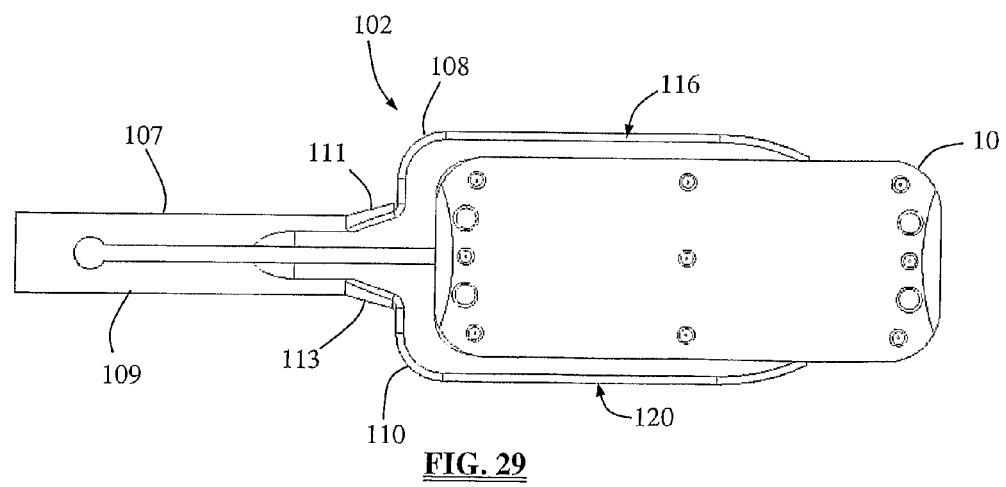
FIG. 29 is a top view of the distal engagement region of FIG. 39 shown engaged with a lateral TDR system of FIG. 2.

The tubular lock member 106 is an elongated member having a lumen 146 extending therethrough. Lumen 146 is dimensioned to receive the elongated shaft 104. Preferably, the lumen 146 includes a diameter slightly larger than that of the elongated shaft 104. The tubular lock member further includes a proximal engagement region 148 having a tool engagement region 150. The interior of the lumen 146 may be provided with a threaded region (not shown) near the proximal end 148 dimensioned to threadedly engage the threaded region 134 of the elongated shaft 104. This threaded mating enables controlled migration of the tubular lock member 106 along the elongated shaft 104. As best shown in FIG. 27, the diameter of the tubular lock member 106 is greater than that of the elongated shaft 104, but less than the widest part of tapered surfaces 111, 113. As will be explained in greater detail below, this enables the tubular lock member to force the prongs 108, 110 together, giving further stability to the cradle 112 as it engages the lateral TDR system 10. Preferably, the insertion tool 100 is provided to a user (e.g. surgeon) fully assembled—that is with the elongated shaft 104 inserted through and threadedly engaging the tubular lock member 106 and the proximal attachment member 132 attached to the elongated shaft 104, though it is contemplated that one or more parts of the insertion tool 100 may be provided separately from the others.

Figure 32:
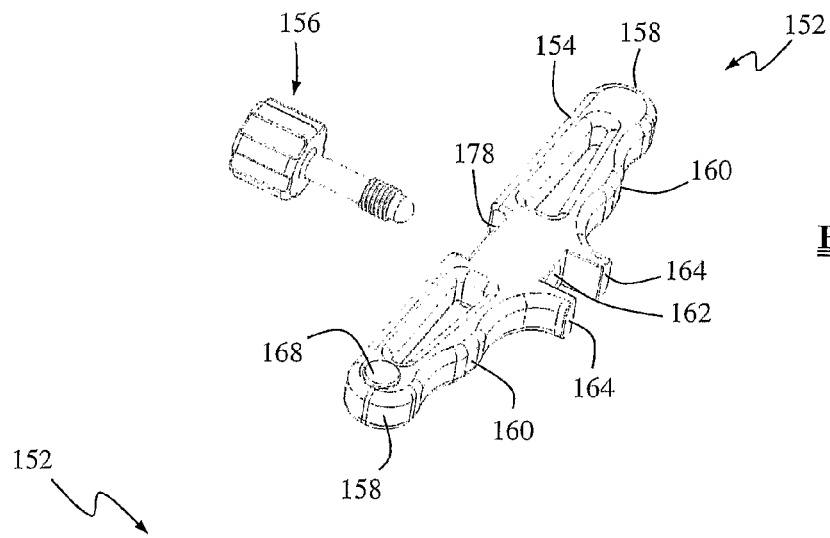
FIGS. 32-34 are exploded and assembled perspective views of a T-handle assembly forming part of the inserter of FIG. 1.
Figure 33:
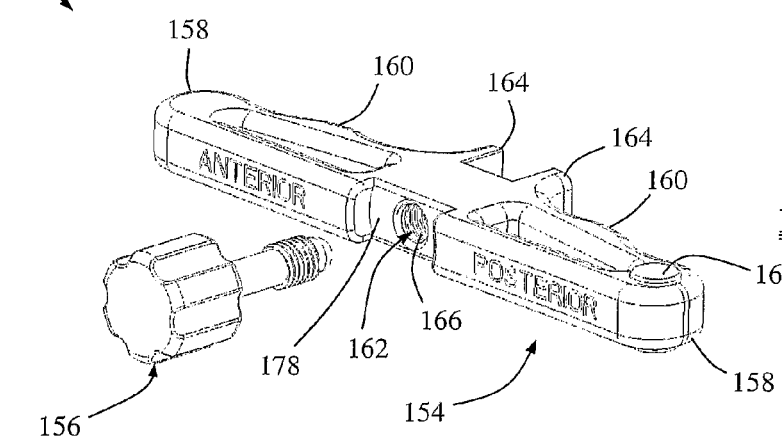
Figure 34:
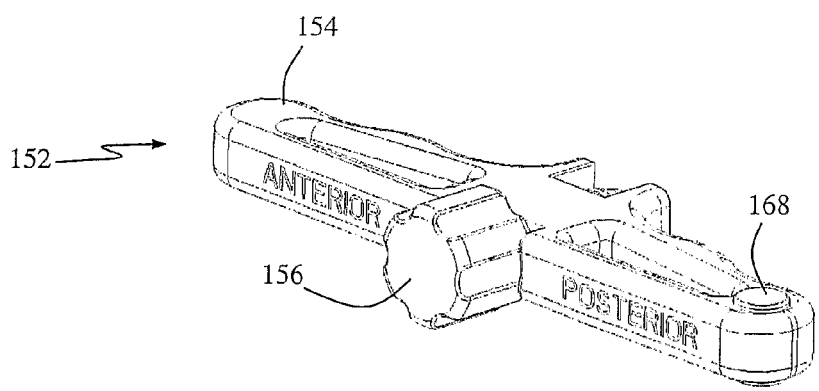

FIGS. 32-34 detail the T-handle assembly 152, which includes a handle 154 and a pin 156. The handle 154 includes a pair of lateral extensions 158 each having a contoured surface 160 dimensioned to comfortably interact with a user's hand. The handle 154 further includes an aperture 162 extending through the width of the handle 154 at an approximate midline and a pair of attachment flanges 164 dimensioned to engage with recesses 142 of the T-handle engagement region 140 of the proximal attachment member 132. Optionally, the interior of aperture 162 may include a threaded region 166. The handle 154 may be further provided with a button 168 at the end of one of the lateral extensions 158 to provide an indication of the orientation of the lateral TDR system 10, when the lateral TDR system 10 includes an offset post 34 as described above. For example, the button 168 may be preferably used to denote the posterior side 13 of the lateral TDR system 10 so that a user will be certain of the correct orientation of the lateral TDR system 10 prior to and during insertion into a patient. The button 168 thus minimizes the occurrence of improper insertion thereby leading to a more efficient surgical procedure. Additional safety measures are also contemplated to ensure the proper orientation of the lateral TDR system 10 on insertion. By way of example only, the handle 154 may be inscribed with one or more marking to visually indicate the proper orientation. As illustrated in FIGS. 33-34, the words "POSTERIOR" and "ANTERIOR" are prominently displayed on handle. Preferably this safety feature may be used in addition to button 168. By way of further example, insertion tool 100 and/or TDR system 10 may be modified in such a way that engagement of TDR system 10 to distal engagement region 102 may only occur in the proper orientation. This may be accomplished for example, by providing different size recesses 42, 44, on the posterior 13 and anterior 15 sides of anchor plates 12, 14. In another embodiment this may be accomplished by altering the shape of ridges 38, 40 on only one side (e.g. posterior side 13) of anchor plates 12, 14.

A pin 156 is provided to securely mate the T-handle to the proximal attachment member 132 of the elongated shaft 104. The pin 156 includes a head region 170 and a shaft 172. The head region 170 is generally cylindrical in shape and includes a contoured surface 174 to improve the grip for a user. The shaft 172 is dimensioned to traverse the aperture 162 and includes a set of threads 176 dimensioned to threadedly engage threaded region 166 of aperture 162 and also the lumen 144 of the proximal attachment member 132. The handle 154 may further include a recess 178 dimensioned to receive at least a portion of the head region 170 so as to reduce the overall profile of the T-handle assembly 152.

Figure 35:
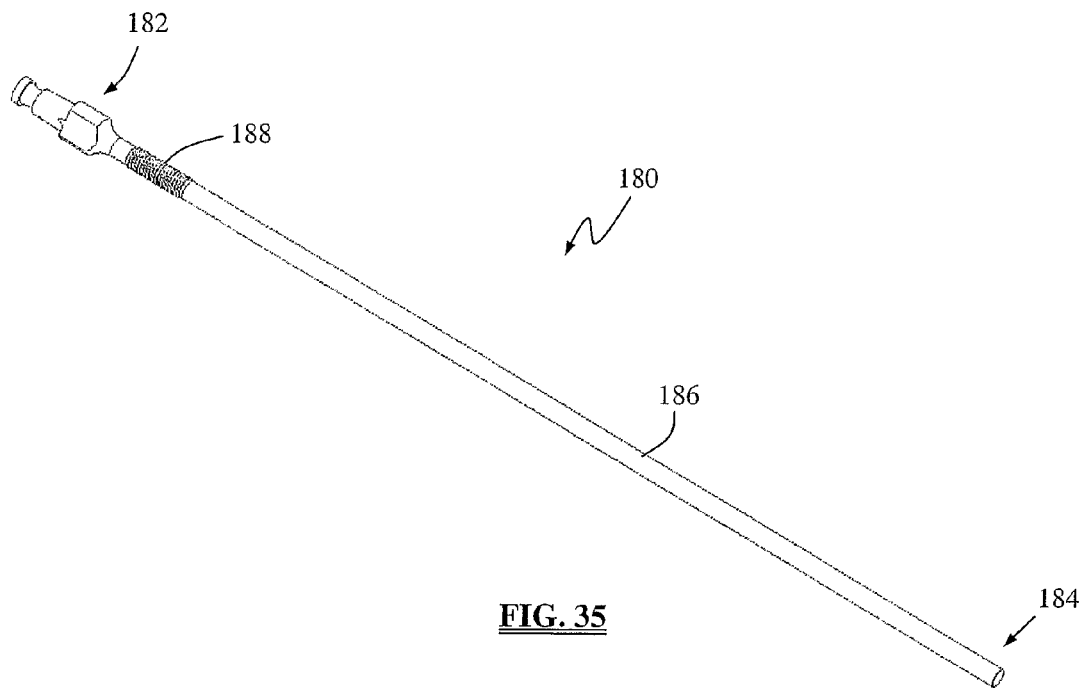
FIG. 35 is a perspective view of an exemplary pusher for use with the lateral TDR system and inserter according to one embodiment of the present invention.
Figure 36:
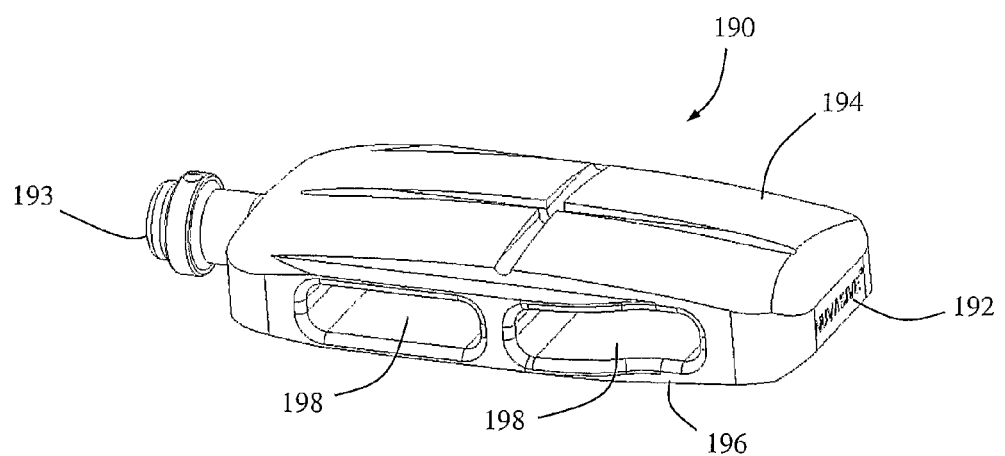
FIGS. 36-40 are front (distal) perspective, rear (proximal) perspective, top, side (lateral), and rear (proximal) views, respectively, of an exemplary sizer for use with the lateral TDR system of FIG. 1.
Figure 37:
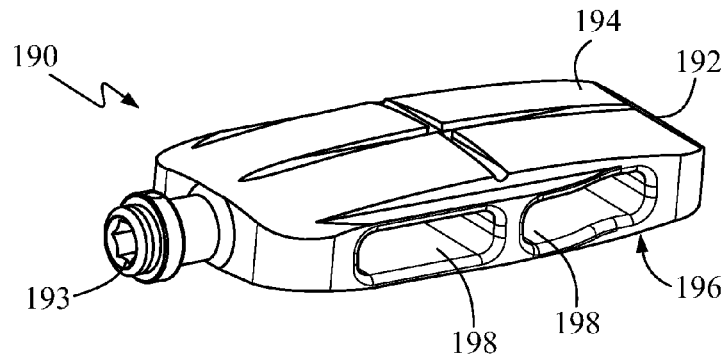
Figure 38:
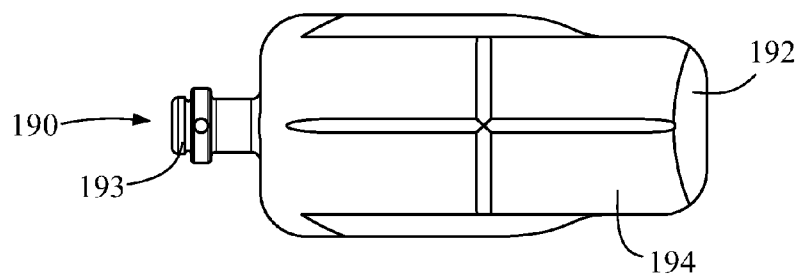
Figure 39:
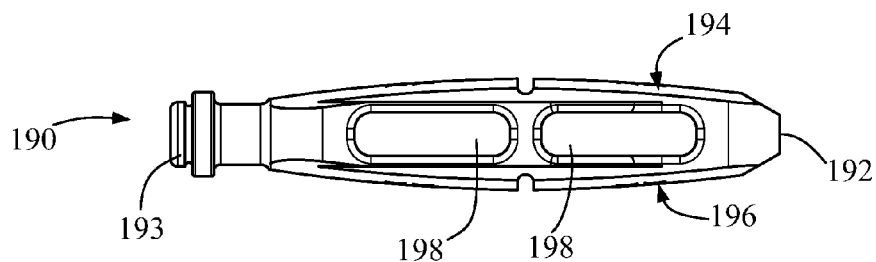
Figure 40:
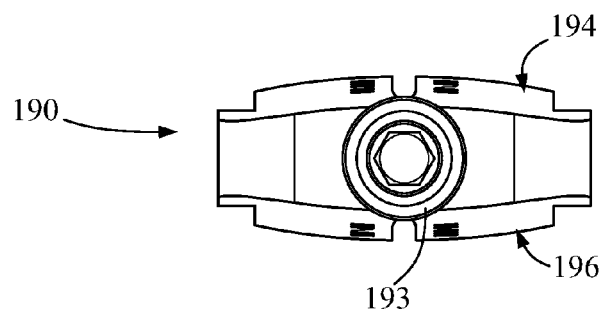

FIG. 35 illustrates an example of a push rod 180 for use with the insertion tool 100 described above. The push rod 180 is an elongated member having a proximal end 182, a distal end 184 and an elongated shaft 186 extending therebetween. The proximal end is dimensioned to attach to a detachable handle member (not shown) to allow a user to manipulate the push rod 180. The distal end 182 may be generally flat and is dimensioned to engage with the lateral TDR system 10 of the present invention. The elongated shaft 186 is generally cylindrical in shape and dimensioned to be slideably received within lumen 136 of the elongated shaft 104. A threaded region 188 may be provided at a proximal end of the elongated shaft 186 in order to threadedly engage the lumen 144 of the proximal attachment member 132 to allow for controlled release of the lateral TDR system 10 into an intervertebral space.

In order to use the system to perform a total disc replacement procedure, the clinician must first determine the appropriate size of the lateral TDR system required. FIGS. 36-40 illustrate an example of a trial sizer 190 according to one embodiment of the present invention. Sizer 190 may be provided in a variety of sizes (preferably corresponding to the available TDR system 10 sizes, such as for example, those sizes listed above in Table 1) to enable a clinician to determine the appropriate size of a TDR system 10 to insert into a particular patient's intervertebral space. The sizer is thus generally rectangular in shape, and has a distal end 192, a proximal tool engagement feature 193, first and second opposing sides 194, 196 and at least one aperture 198 extending therethrough. The distal end 192 may be slightly tapered in shape to allow for self-distraction of the disc space during insertion of the initial sizer 190. The proximal tool engagement feature 193 may be provided in any suitable fashion to allow interaction with any desirable insertion tool. The first and second opposing surfaces 194, 196 are each provided having a generally convex proximal-to-distal profile and a generally convex lateral profile to enable the sizer 190 to anticipate the shape of the intervertebral space. Apertures 198 may be provided in any shape and size and function to reduce the overall mass of the sizer 190.

A clinician can utilize the lateral TDR system 10 in either an open or minimally invasive lateral total disc replacement procedure. In either type of procedure, a working channel would be created in a patient that reaches the targeted spinal level. After the creation of that channel, the intervertebral space must be prepared, meaning the disc space must be accessed via an annulotomy followed by a full or partial discectomy. End plate preparation may or may not be performed according surgeon preference, among other factors. In a preferred embodiment, the final step of disc space preparation entails releasing the contra-lateral annulus (i.e. the annulus directly across the disc space from the original entry point into the disc). Releasing the contra-lateral annulus is advantageous in that it increases the likelihood of proper motion preservation after the lateral TDR system 10 is implanted due to the elimination of a potentially limiting tension band in the form of the contra-lateral annulus. After the clinician has prepared the disc space and determined the correct size of TDR system 10 to use (by using the sizer 190), the lateral TDR system 10 is ready to be attached to the inserter 100 and inserted into the disc space. As shown by example in FIGS. 28-29, the clinician will engage the cradle 112 to the lateral TDR system 10 by sliding ridges 122, 124 into grooves 38, 40, respectively, until protrusions 126, 128 engage recesses 42, 44 and the lateral TDR system 10 is secured onto the insertion tool 100. After disc space preparation, the insertion tool 100 is used to place the lateral TDR system 10 into the prepared intervertebral space. Once the lateral TDR system 10 is inserted into the prepared space into the desired position (shown in FIGS. 45-47, which may be confirmed via fluoroscopy or any other suitable imaging technique), the lateral TDR system 10 is released from the inserter 100.

FIGS. 41-44 illustrate an example of an insertion procedure of the lateral TDR system 10 using the insertion tool 100. Upon mating of the cradle 112 and the lateral TDR system 10, the tubular lock member 106 may then be used to lock the lateral TDR system 10 within the cradle 112. This is accomplished by advancing the tubular lock member 106 along the elongated shaft 104 such that the distal end of the tubular lock member 106 approaches the tapered surfaces 111, 113 (see e.g. FIGS. 26-27), forcing the prongs 108, 110 together and creating a compressive force on the lateral TDR system 10. This functions to "lock" the lateral TDR system 10 within the cradle 112. To advance the tubular lock member 106, a tool such as a wrench 197 may be applied to the tool engagement region 150 and turned such that the threaded region of lumen 146 and threaded region 134 of the elongated shaft 104 interact to controllably advance the tubular lock member 106.

Once the lateral TDR system 10 has been inserted into the cradle 112 and locked with the tubular lock member 106, the lateral TDR system 10 (via insertion tool 100) is advanced along a surgical corridor to a target disc space. To properly position the lateral TDR system 10 during the insertion, anti-migration features 36 may be utilized as guides. As previously mentioned, anti-migration features 36 may preferably be arranged along the longitudinal midline (i.e. co-linear with the X-axis) and the lateral midline (i.e. co-linear with the Z-axis) of anchor plates 12, 14. Prior to inserting the system 10 a surgeon may first determine the longitudinal midline of the intervertebral space (i.e. a midpoint along the Z-axis) and place an indicator (such as, by way of example, a radiographic marker in the form of a screw 17) at this midpoint location on the lateral aspect of one or more of the adjacent vertebral bodies. This may be particularly important (for example) if a posteriorly-biased configuration is used. Fluoroscopic imaging may be used to check the alignment of anti-migration features 36 with screw 17. The lateral TDR system 10 may then be inserted such that the anti-migration features 36 aligned on the longitudinal midline of plates 12, 14 line up with the indicator on the longitudinal midline of the intervertebral space, thus ensuring proper positioning in the anterior-posterior direction. To ensure proper lateral placement of the system 10, the anti-migration features 36 aligned along the lateral midline of anchor plates 12, 14 (i.e. co-linear with the Z-axis) may be placed inline with the spinous processes and/or the lateral midline (from anterior view) of one or more of the adjacent vertebral bodies. Either or both of these alignment techniques helps ensure the proper lateral alignment of the lateral TDR system 10 according to one aspect of the present invention.

Figure 45:
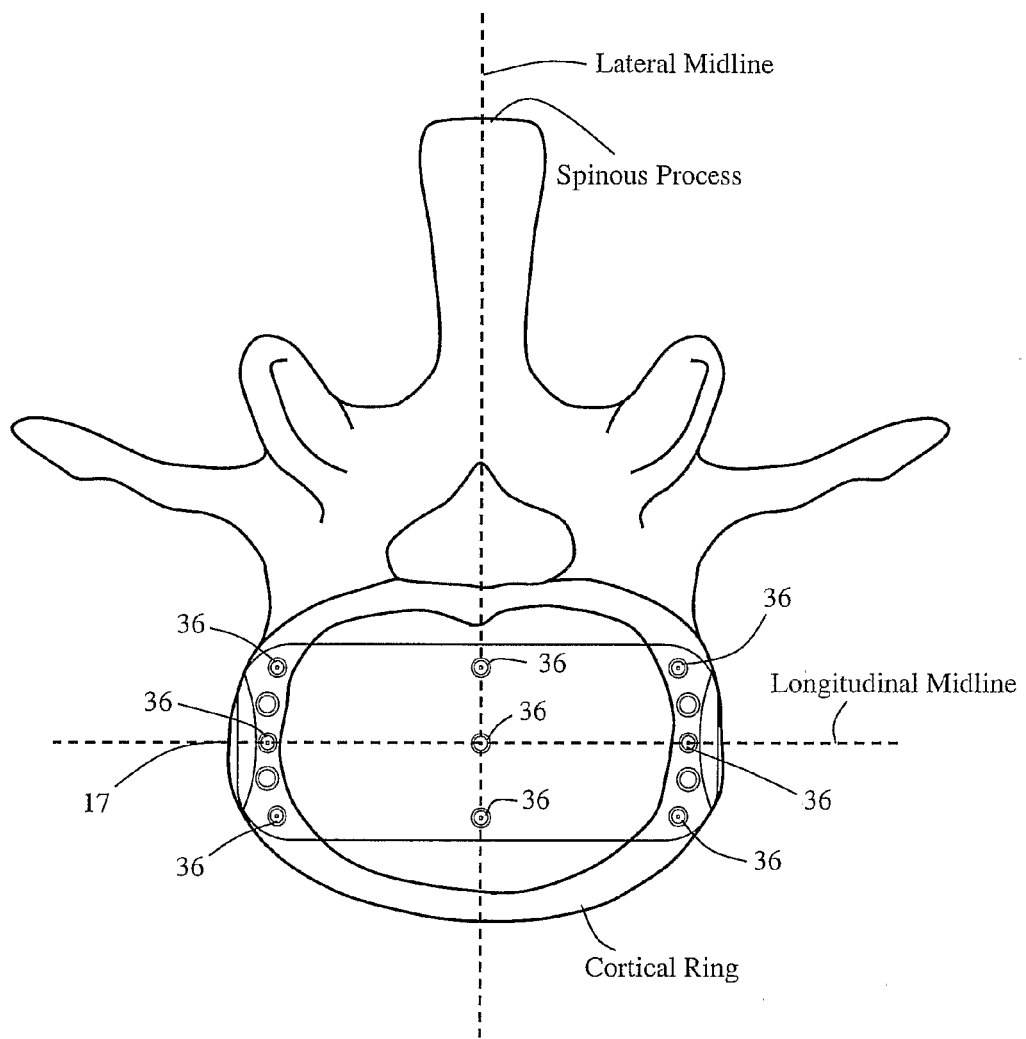
FIGS. 45-47 are top, anterior, and lateral views, respectively, of the lateral TDR system of FIG. 2 positioned within the intervertebral disc space according to one embodiment of the present invention.
Figure 46:
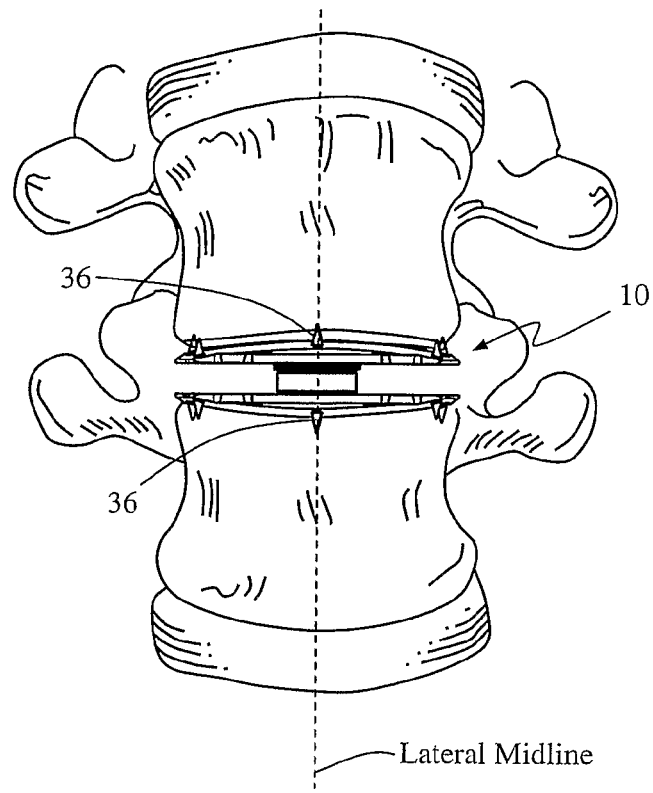
Figure 47:
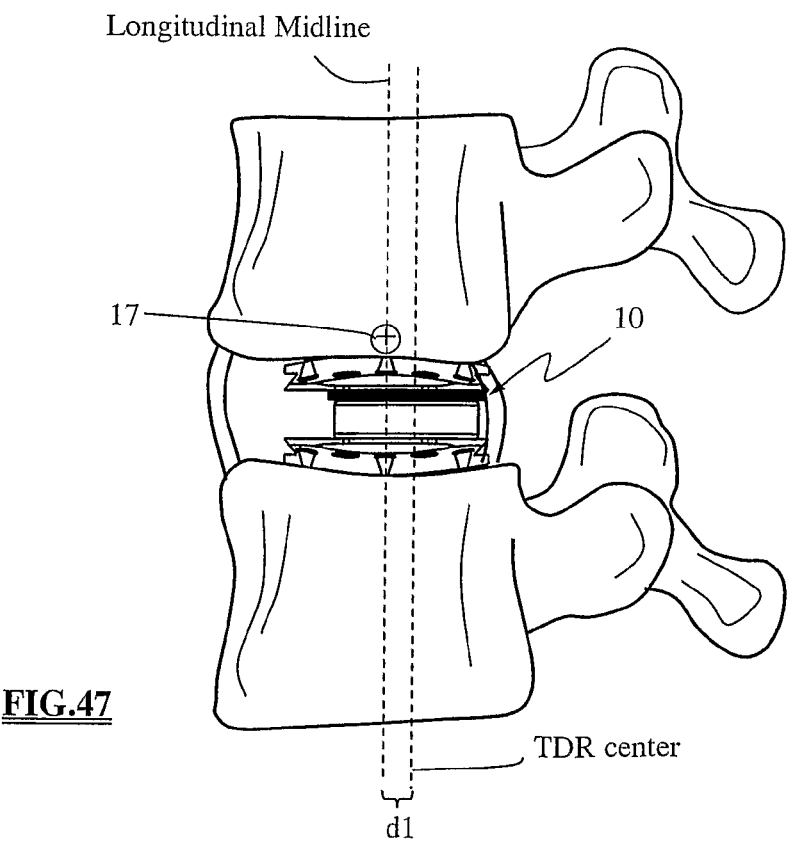

FIG. 45 illustrates, by way of example only, the proper positioning of the lateral TDR system 10 within the disc space from a top-down view. Anti-migration features 36 aligned along the longitudinal and lateral midlines of anchor plates 12, 14 are positioned inline with the midline indicator and spinous process, respectively. FIG. 46 is an anterior view of TDR system 10 properly positioned in the disc space. The central row of anti-migration features 36 arranged along the lateral midline of anchor plates 12, 14 line up with the lateral midline of the vertebra. FIG. 47 is an anterior view of the lateral TDR system 10 properly positioned in the disc space. The central row of anti-migration features 36 are aligned with the longitudinal midline of the vertebra. As viewed in FIG. 47, accurate alignment of the central row of anti-migration features 36 ensures proper positioning of the posteriorly-disposed intradiscal element 16. When the anchor plates 12, 14 are positioned in this manner, the center of intradiscal element 16 is automatically disposed in the posterior region of the disc space and separated from the longitudinal midline of the vertebra by a distance d1. In the lumbar setting, the distance d1 is preferably such that the center of intradiscal element 16 is positioned within the posterior region of the disc space (most preferably within the posterior one-third of the disc space). Proper positioning of the system 10 within the disc space includes not only the alignment of the lateral TDR system 10, but also preferably includes having the lateral ends of the anchor plates 12, 14 disposed over the hard cortical ring of the adjacent vertebral bodies. In one embodiment, the rows of anti-migration features 36 disposed on the lateral ends of the anchor plates 12, 14 are preferably positioned on the hard cortical ring of the adjacent vertebral bodies, which advantageously aids in preventing the unwanted migration of the anchor plates 12, 14 from the optimal location after implantation.

Figure 42:
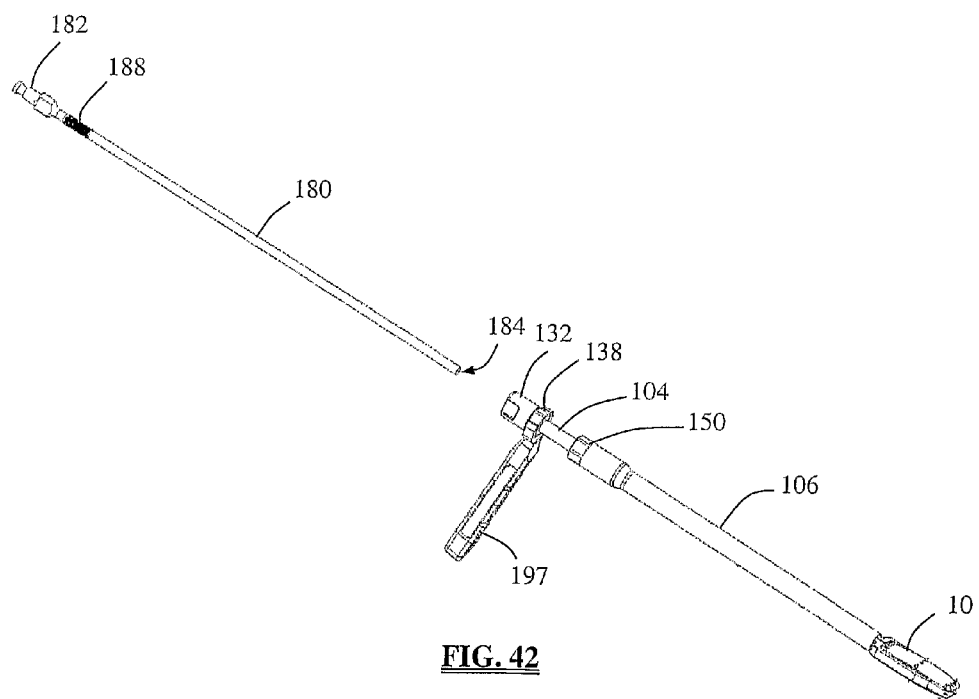
Figure 43:
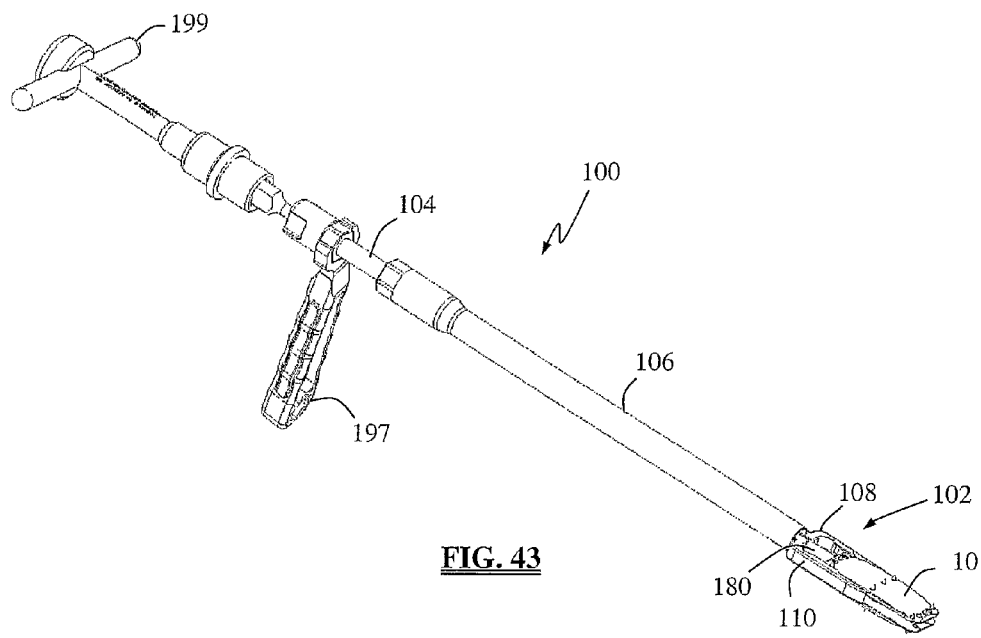
Figure 44:
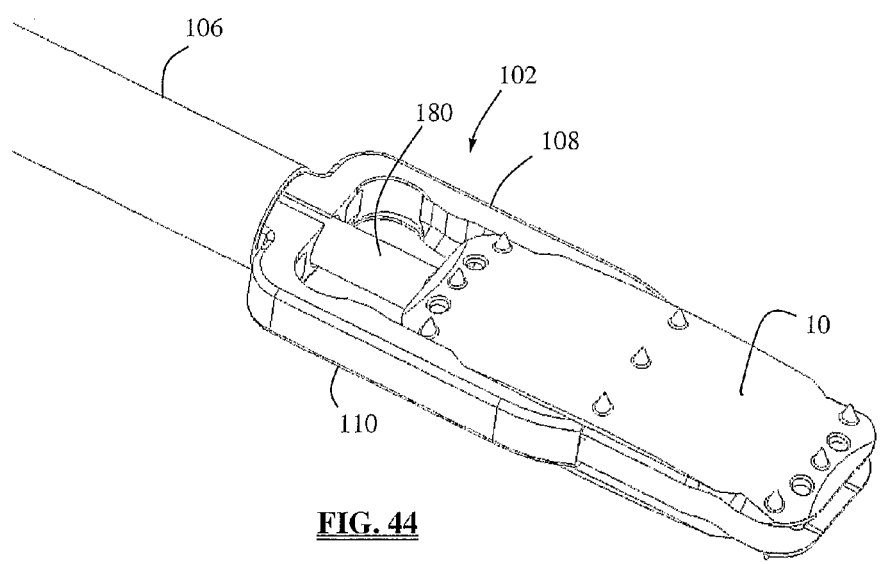

Referring to FIG. 42, the wrench 197 is removed from the tool engagement region 150 of the tubular lock member 106 and mated with the tool engagement region 138 of the proximal attachment member 132 of the elongated shaft 104. This will enable the clinician to hold the elongated shaft 104 in place to prevent rotation during insertion and use of additional hardware such as push rod 180. Push rod 180 may then be inserted into lumen 144 of the proximal attachment member 132 and advanced along lumen 136 of the elongated shaft 104 until the distal end 184 encounters the lateral TDR system 10 (shown by way of example in FIG. 43). At this point, a handle member 199 may be attached to the proximal end 182 to allow a user to apply sufficient force to the push rod 180 to force the lateral TDR system 10 out of the cradle 112 (shown by way of example in FIG. 44). Before forcing the lateral TDR system from the cradle 112, however, it may be advantageous to unlock the tubular lock member 106 by applying wrench 197 to the tool engagement region 150 and turning in an opposite direction from the locking motion. In most cases it will only be necessary to use the push rod 180 to force the recesses 42, 44 of the lateral TDR system 10 out of engagement with protrusions 126, 128 of the insertion tool 100, since at that point the distal region 102 may slideably detached from the lateral TDR system 10 and thereafter removed from the operating corridor.

The lateral TDR system 10 of the present invention disclosed herein may be provided with various modifications without departing from the scope of the invention. For example, the intradiscal element 16 may be prevented from translating relative to the first and/or second anchor plates 12, 14 in any suitable fashion, such as by equipping the either or both of the anchor plates 12, 14 and/or the intradiscal element 16 with a structure (e.g. a wall member extending from the anchor plate) or by altering the difference in diameters between the post 34 and central bore 56.

At times it may be advantageous to be able to insert a TDR system into an intervertebral space without having to employ a separate distraction tool to keep the adjacent vertebrae far enough apart to allow insertion of the lateral TDR system. To that end, an insertion tool may be provided wherein the prongs are provided with a greater height than the lateral TDR system so as to allow the act of insertion of the lateral TDR system into the disc space simultaneously cause the distraction of the space.

Figure 56:
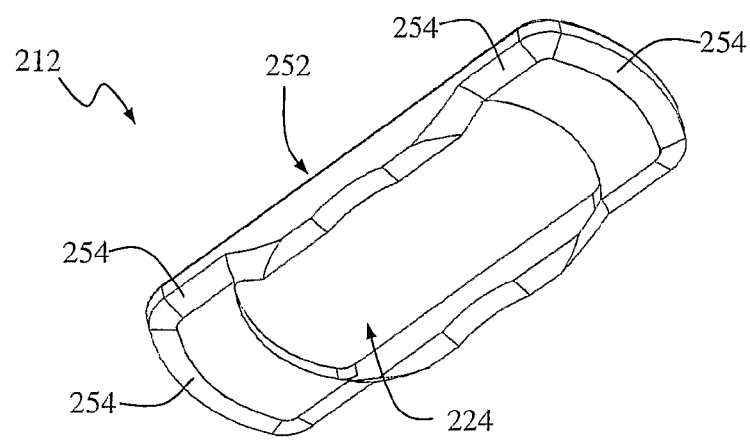
FIG. 56 is a perspective view of the underside of a first anchor plate forming part of the lateral TDR system of FIG. 48.
Figure 57:
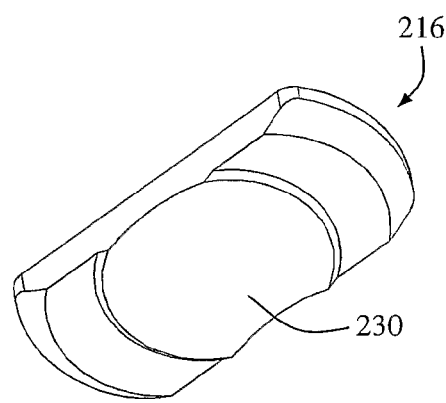
FIG. 57 is a perspective view of the underside of a first intradiscal insert forming part of the lateral TDR system of FIG. 48.
Figure 58:
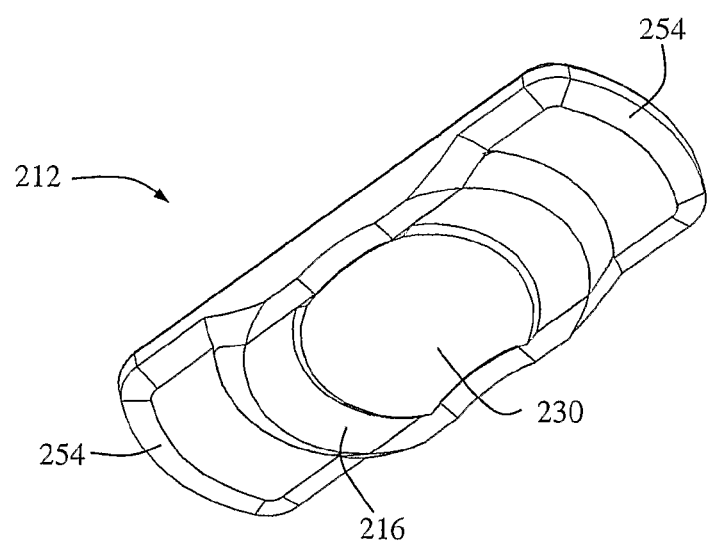
FIG. 58 is a perspective view of the intradiscal insert of FIG. 57 coupled with the anchor plate of FIG. 56.
Figure 59:
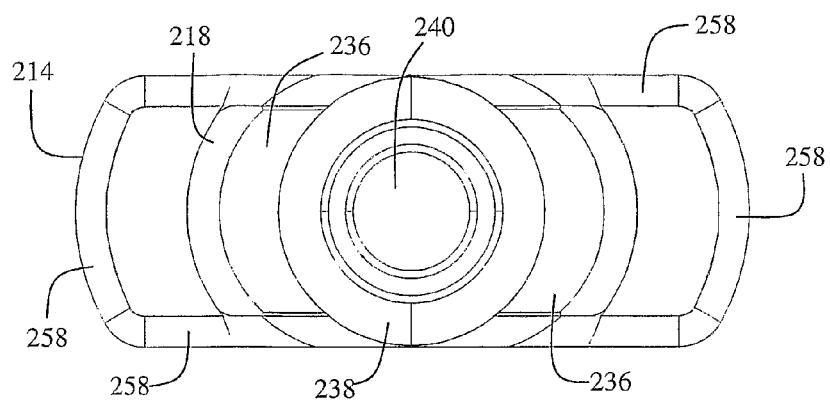
FIGS. 59-61 are top, top perspective, and bottom perspective views, respectively, of the lateral TDR system of FIG. 48 with the first anchor plate and first intradiscal insert removed.
Figure 60:
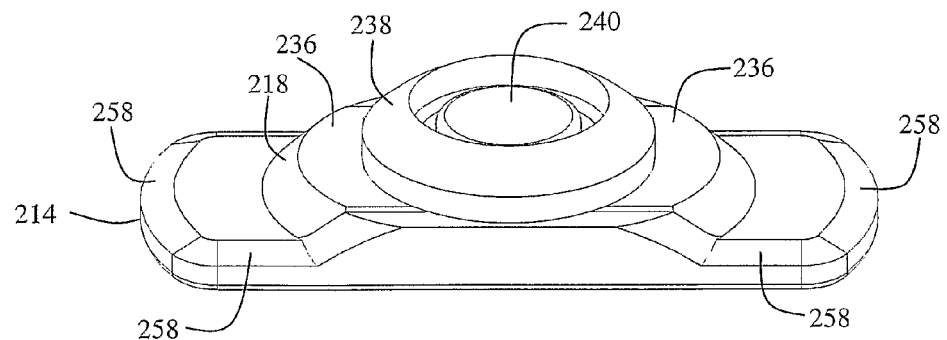
Figure 61:
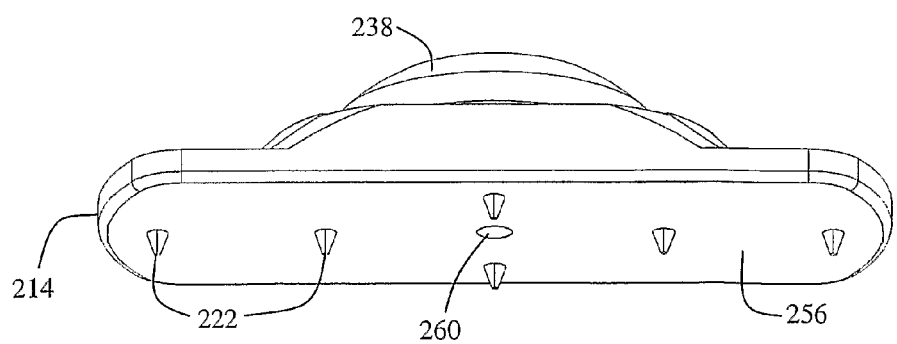
Figure 62:
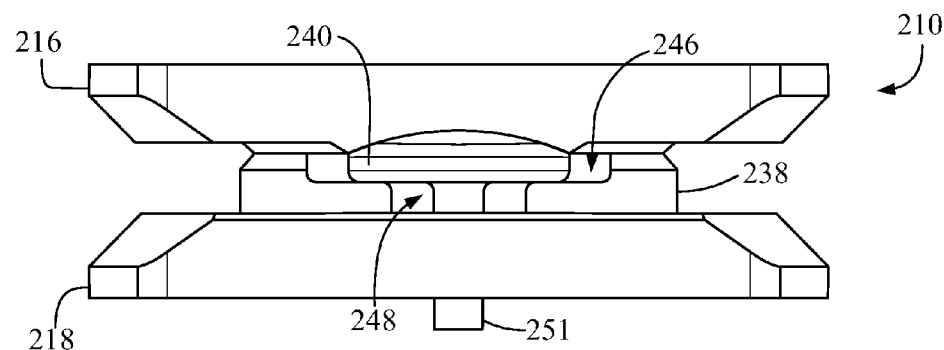
FIGS. 62-63 are side (anterior or posterior) views of an intradiscal element in conjunction with a first and second intradiscal insert according to one embodiment of the present invention, wherein the intradiscal element has been made transparent to show the relative positioning of the anchor pin.
Figure 63:
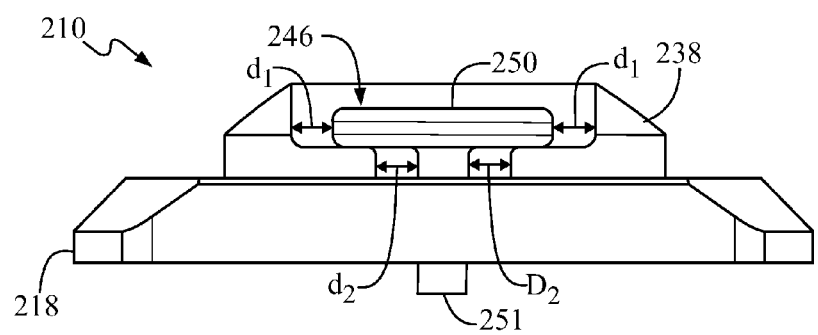
Figure 64:
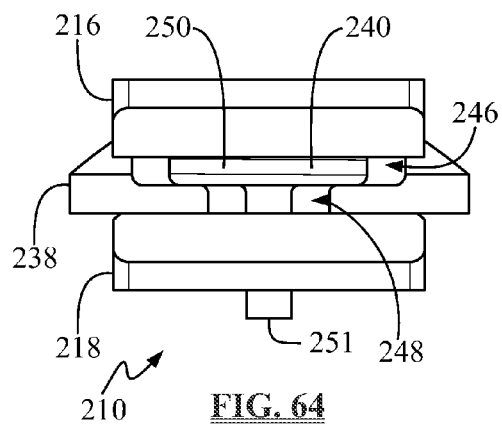
FIGS. 64-65 are end (lateral) views of an intradiscal element in conjunction with a first and second intradiscal insert according to a first embodiment of the present invention, wherein the intradiscal element has been made transparent to show the relative positioning of the anchor pin.
Figure 65:
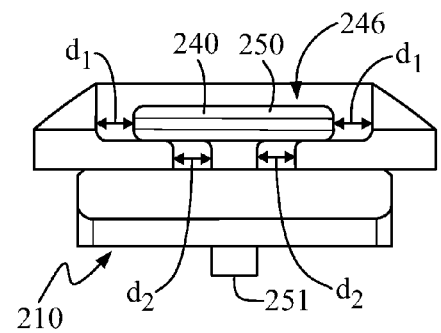

FIGS. 48-71 illustrate a TDR system 210 according to an alternative embodiment of the present invention. Referring to FIGS. 48-51, the lateral TDR system 210 includes a first anchor plate 212, a second anchor plate 214, a first and second intradiscal insert 216, 218, and an intradiscal element 220. Each anchor plate 212, 214 is equipped with a plurality of anti-migration features 222 and a cutout region 224, 226, respectively. The first intradiscal insert 216 has a first generally planar surface 228 dimensioned to fit into the cutout region 224 of the first anchor plate 212 (FIGS. 56-58) and a second articular surface 230 having a generally arcuate cross-section dimensioned to articulate with the intradiscal element 220. The second intradiscal insert 218 has a first surface 234 dimensioned to fit into the cutout region 226 of the second anchor plate 214 and a second generally planar surface 236 dimensioned to interact with the intradiscal element 220.

Figure 52:
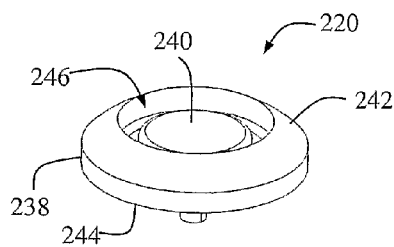
FIGS. 52-53 are assembled and exploded perspective views, respectively, of an intradiscal assembly forming part of the lateral TDR system of FIG. 48.
Figure 53:
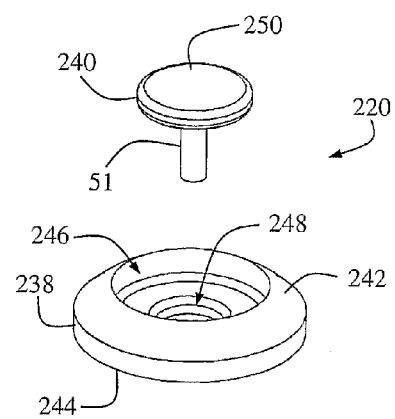
Figure 54:
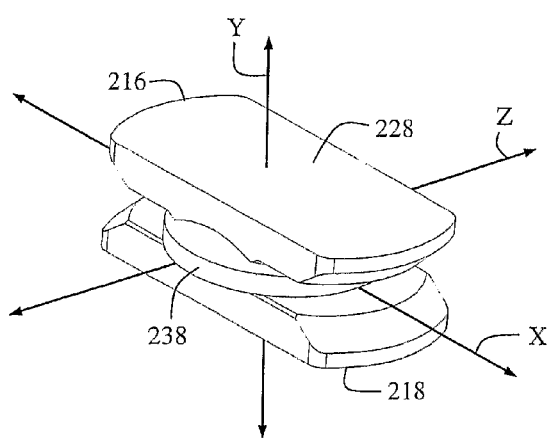
FIGS. 54-55 are assembled and exploded perspective views, respectively, of the lateral TDR system of FIG. 48.

FIGS. 52-53 illustrate an exemplary embodiment of an intradiscal element 220 according to a first embodiment of the present invention. The intradiscal element 220 may include a pivot 238 and retaining pin 240. The pivot 238 may comprise any shape that allows for a complete range of motion, including but not limited to circular, oval, square, and rectangular. In a preferred embodiment, the pivot 238 is generally circular in shape, and includes a first articular surface 242, a second generally planar surface 244, and a cutout region 246. The first articular surface 242 is dimensioned to articulate with the second articular surface 230 of the first intradiscal insert 216 such that, by extension, the first anchor plate 212 may rotate relative to the intradiscal element 220 about any axis defined by a line within the XZ plane that intersects the Y-axis (FIG. 54). The second generally planar surface 244 is dimensioned to interact with the second generally planar surface 236 of the second intradiscal insert 218 such that, by extension, the second anchor plate 214 may rotate relative to the intradiscal element 220 about the Y-axis. In this fashion, rotation about any axis in the XZ plane will always occur at the same location along the first anchor plate 212 and rotation about the Y-axis will always occur at the same location along the second anchor plate 214. Cutout region 246 includes a central aperture 248 dimensioned to allow pin 240 to pass though pivot 238 and interact with second intradiscal insert 218. Central aperture 248 may be generally circular in shape, and have any diameter necessary to allow for an optimal range of motion, which may vary between different embodiments of the total disc replacement system 210 and depend on the desired destination of the implant (e.g. lumbar, thoracic, and cervical spine).

Figure 55:
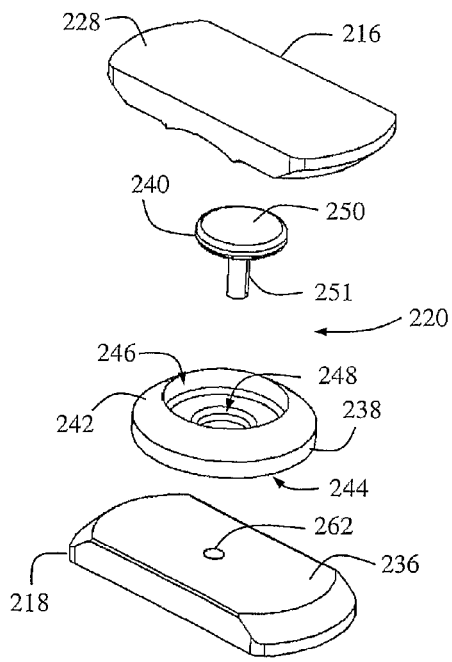

The pin 240 includes a shaped head region 250 and an elongated member 251. Head region 250 may comprise any shape allowing a complete range of motion, including but not limited to circular, oval, square, and rectangular. In a preferred embodiment, the head region 250 is generally circular to allow for smooth rotation in any direction. Head region 250 is dimensioned to interact with the cutout region 246 of the pivot 238, such that the head region 250 prevents the pivot 238 from exceeding a desired range of motion once the pin 240 has been secured to the second intradiscal insert 218 and/or second anchor plate 214. Thus, the head region 250 may be of any diameter necessary to accomplish this, provided that diameter is less than the diameter of the cutout region 246 and greater than the diameter of aperture 248. Elongated member 251 extends in a generally perpendicular manner from head region 250 and is dimensioned to couple with aperture 262 on second intradiscal insert 218 (FIG. 55).

Figure 68:
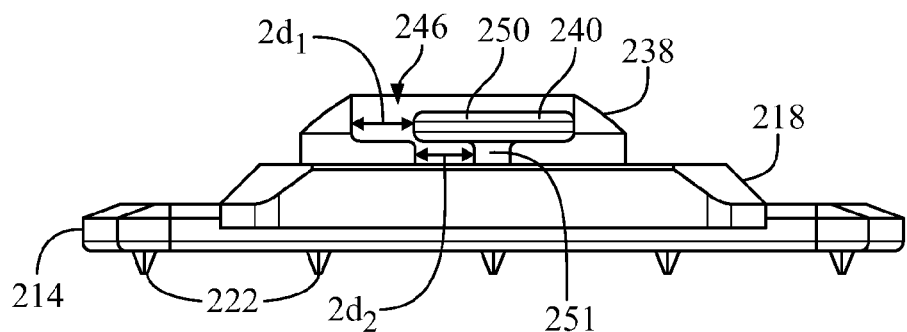
FIG. 68 is a side (anterior or posterior) view of the lateral TDR system of FIG. 67 with a first anchor plate and first intradiscal insert removed, wherein the intradiscal element has been made transparent to show the relative positioning of the anchor pin.
Figure 71:
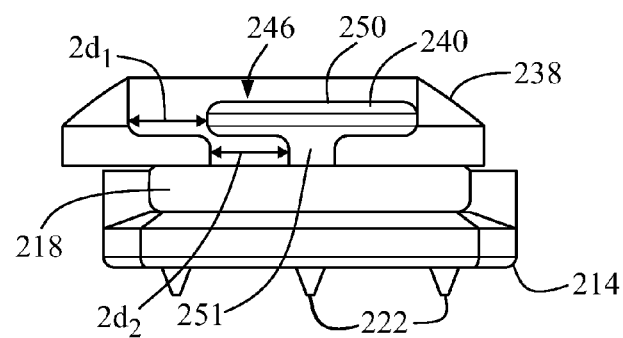
FIG. 71 is an end (lateral) view of the lateral TDR system of FIG. 70 with a first anchor plate and first intradiscal insert removed, wherein the intradiscal element has been made transparent to show the relative positioning of the anchor pin.

The diameter of central aperture 248 may be substantially greater than the diameter of elongated member 251, and slightly greater than the difference in diameter between the head region 250 and cutout region 246. These differences in diameters function to allow for translation of the first anchor plate along any axis in the XZ plane, with the actual distance providing a limit on the degree of translation allowed. Specifically, the first anchor plate 212 can only translate as far as the distance defined by the difference in radii between the head region 250 and cutout region 246 (denoted by lines $d_1$ in FIGS. 63 & 65). The difference in radii between the elongated member 251 and the central aperture 248 (denoted by lines $d_2$ is FIGS. 63 & 65) is greater than the difference in radii between head region 250 and cutout region 46 (i.e. $d_2 > d_1$) in order to ensure that at least a portion of the pivot 238 remains beneath the retaining pin 240. More importantly, pin 240 may be manufactured such that the difference in radii between the head region 250 and the elongated member 251 is greater than $2d_2$, such that upon translation, a portion of head region 250 always overlaps at least a portion of pivot 238 (FIGS. 68 & 71). Thus, the lateral TDR system 210 of this first embodiment provides rotation along a plurality of axes (any axis in the XZ plane, and the Y-axis) and translation along a plurality of axes (any axis in the XZ plane). At least a portion of the distal region of elongated member 251 may be threaded to engage with second anchor plate 214 to provide for increased stability to the lateral TDR system 210 of the present invention.

When used within the lumbar spine, for example, it may be desirable to configure the second anchor plate 214 such that the cutout region 226 is located within the posterior one-third of the disc space (and generally within the frontal plane of the patient) to approximate the axis of rotation of the natural spine during flexion and extension. It may similarly be desirable to configure the first anchor plate 212 such that the cutout region 224 is located at the approximate center of the disc space (and generally within the sagittal plane of the patient) to approximate the axis of rotation of the natural spine during lateral bending. Although described by way of example in this configuration, it will be appreciated that the relative position of the cutout regions 224, 226 may be altered in any number of different fashions depending upon the vertebral level (i.e. cervical, thoracic, and/or lumbar) as well as the directional approach employed to place the lateral TDR system 210 into a disc space (e.g., lateral, anterior, postero-lateral, antero-lateral). Moreover, it will be appreciated that the lateral TDR system 210 may be introduced into a disc space in the orientation shown (with the first anchor plate 212 "above" the second anchor plate 214 such that the anti-migration features 222 are to be disposed within a respective "upper" and "lower" vertebral level within the patient) or vice versa.

Referring to FIGS. 48-51 & 56-58, the first anchor plate 212 includes a generally planar surface 252 for engaging a vertebra and a plurality of generally angled surfaces 254, which may extend in a ramp-like fashion away from the lateral edges of the first anchor plate 212 at least partially towards the cutout region 224. The generally angled surfaces 254 serve to limit the relative rotation of the lateral TDR system 210 about an axis in the XZ plane. That is, the first anchor plate 212 will be able to rotate about the desired axis until a generally angled surface 254 comes into contact with another structure, such as the second intradiscal insert 218 or the second anchor plate 214. A cutout region 224 may be provided at the approximate mid-line or middle of the first anchor plate 212 and is dimensioned to receive a first intradiscal insert 216. The cutout region 224 functions to prevent any lateral or rotational movement of the first intradiscal insert 16 in relation to first anchor plate 212, as well as to reduce the overall profile of the lateral TDR system 210 of the present invention. Additionally, the first intradiscal insert 216 may serve as a protective intermediary between the intradiscal element 220 and first anchor plate 212.

A plurality of anti-migration features 222 may be provided on the first anchor plates 212 to inhibit the movement of said anchor plate after introduction into a receiving area within a vertebra. In one embodiment, the anti-migration features 222 may comprise protrusions having a generally triangular cross-section, although any number of suitable configurations or anti-migration elements may be employed without departing from the scope of the present invention. Any number of mechanisms or techniques may be employed to introduce first anchor plate 212 into a vertebra, including but not limited to providing one or more lumens and/or grooves (not shown) in the first anchor plate 212 for coupling to or engaging with an insertion tool (not shown).

Figure 48:
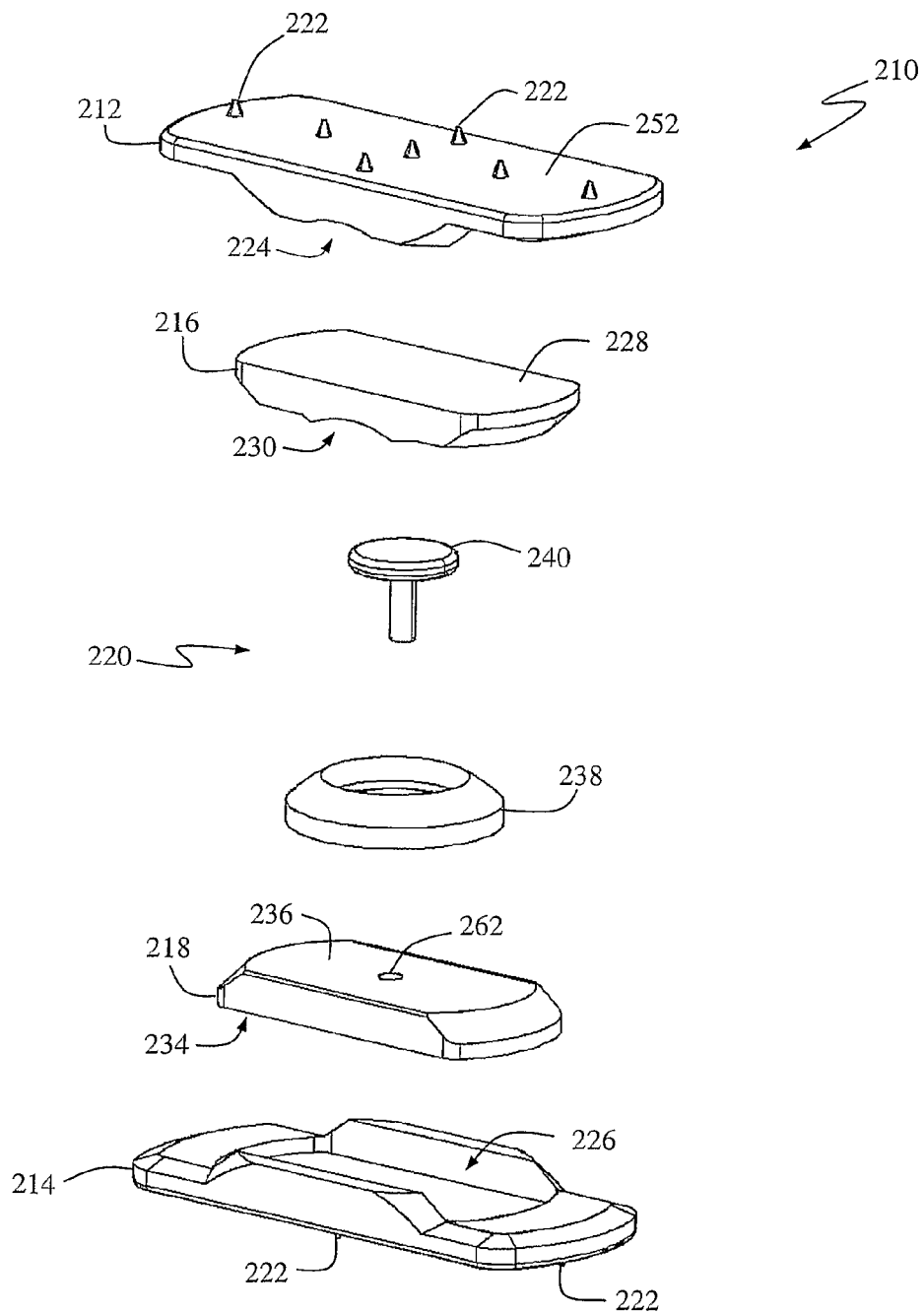
FIGS. 48-49 are exploded and assembled perspective views, respectively, of a lateral TDR system according to an alternative embodiment of the present invention.
Figure 49:
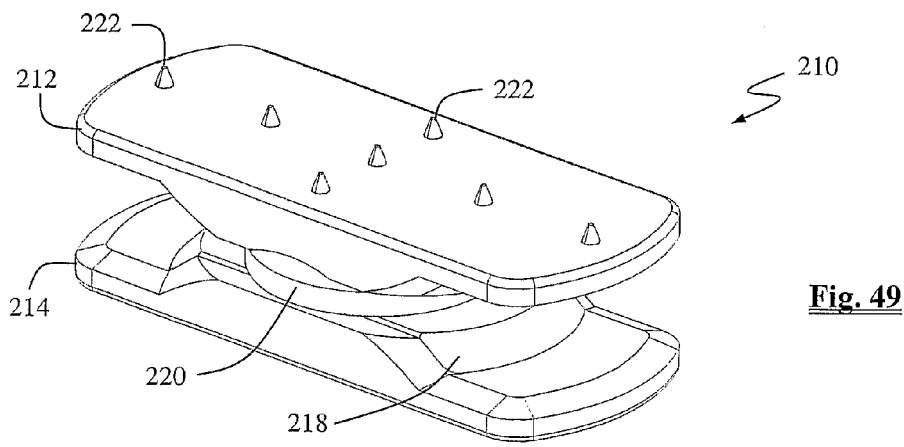
Figure 50:
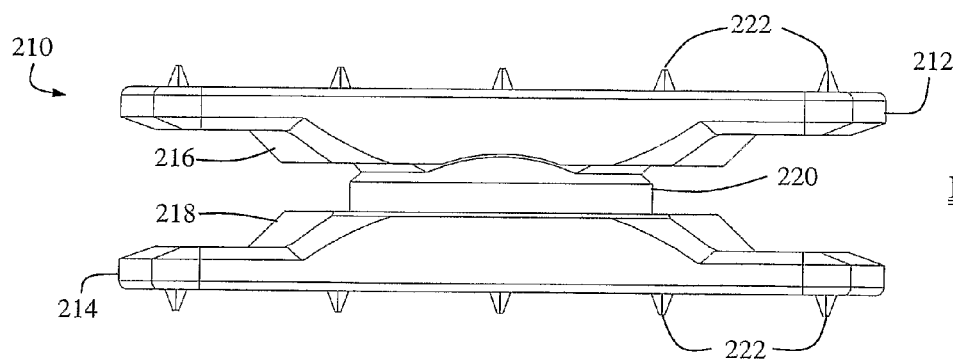
FIGS. 50-51 are side (anterior or posterior) and end (lateral) views, respectively, of the lateral TDR system of FIG. 48.
Figure 51:
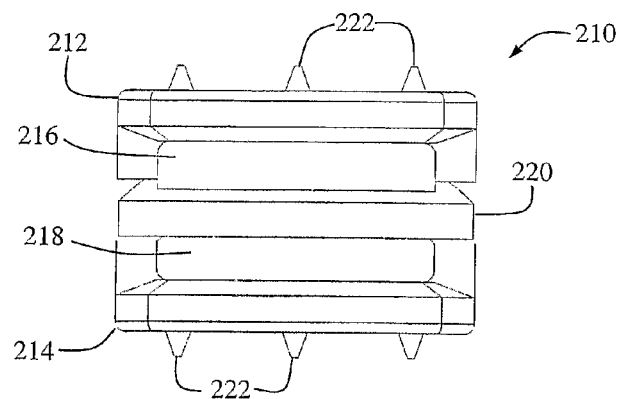

Second anchor plate 214 includes a generally planar surface 256 (FIGS. 59-61) for engaging a vertebra, a plurality of generally angled surfaces 258, and a cutout region 226 (FIG. 48). Cutout region 226 may be provided at the approximate mid-line or middle of the second anchor plate 214 and is dimensioned to receive a second intradiscal insert 218. The cutout region 226 functions to prevent any lateral or rotational movement of the second intradiscal insert 218 in relation to second anchor plate 214, as well as reduce the overall profile of the lateral TDR system 210 of the present invention. The second intradiscal insert 218 may serve as a protective intermediary between intradiscal element 220 and second anchor plate 214. The generally angled surfaces 258 extend in a generally lateral fashion away from the lateral edges of the second anchor plate 214 at least partially towards the cutout region 226. Second anchor plate 214 may also include a central aperture 260 located approximately in the center of generally planar surface 256. Central aperture 260 may be generally circular in shape, and is dimensioned to receive the elongated member 251 of retaining pin 240. Central aperture 260 should therefore be aligned with aperture 262 of the second intradiscal insert 218 to allow each aperture 260, 262 to receive the elongated member 251 of retaining pin 240.

Central aperture 260 may be threaded to engage with a threaded embodiment of elongated member 251 discussed above.

The second anchor plate 214 may be equipped with the same anti-migration features 222 discussed above with reference to first anchor plate 212 such that a repeat discussion is not necessary. Similarly, any number of mechanisms or techniques may be employed to introduce the second anchor plate 214 into a vertebra, including but not limited to providing one or more lumens and/or grooves (not shown) in the second anchor plate 214 or coupling to or engaging with an insertion tool (not shown).

The first and second anchor plates 212, 214 may be constructed from any number of materials and/or compositions suitable for medical applications, including but not limited to metallic compositions (such as titanium) or alloys (such as Co—Cr—Mo), ceramics (such as zirconia and/or alumina), polymers (such as ultra-high molecular weight polyethylene), and/or any combination thereof. Where beneficial and appropriate, either or both of the first and second anchor plates 212, 214 may also be coated with any number of suitable compositions, such as zirconium oxide coating found in U.S. Pat. No. 5,037,438, the contents of which are hereby incorporated into this disclosure as if set forth in its entirety.

The preferred embodiment of the intradiscal element 220 has been discussed in detail above, and such discussion will not be repeated here. The intradiscal element 220 of the present invention may be constructed from any number of materials and/or compositions suitable for medical applications, including but not limited to metallic compositions or alloys (such as Co—Cr—Mo), ceramics (such as zirconia and/or alumina), polymers (such as ultra-high molecular weight polyethylene), and/or any combination thereof. Where beneficial and appropriate, the intradiscal element 220 may also be coated with any number of suitable compositions, such as zirconium oxide coating found in U.S. Pat. No. 5,037,438, the contents of which are hereby incorporated into this disclosure as if set forth in its entirety. In a preferred embodiment, pivot 238 is constructed from ceramic, while retaining pin 240 is constructed from a metallic composition, such as titanium.

FIGS. 54-55 illustrate a preferred configuration of the first and second intradiscal inserts 216, 218. The first intradiscal insert 216 has a first generally planar surface 228, a second articular surface 230, and a measurable thickness therebetween. The first surface 228 is dimensioned to fit into the cutout region 224 of the first anchor plate 212. Accordingly, the length of the first intradiscal insert 216 traverses a substantial portion of the length of the first anchor plate 212. The second articular surface 230 is dimensioned to interact with the first articular surface 242 of the pivot 238, allowing for the rotational movement of TDR system 210 discussed above. The first intradiscal insert 216 may also form a protective barrier between the intradiscal element 220 and the first anchor plate 212. This barrier serves to reduce friction between the first anchor plate 212 and intradiscal element 220, ultimately enhancing the durability of the lateral TDR system 210.

The second intradiscal insert 218 has a first surface 234, a second generally planar surface 236, and a measurable thickness therebetween. The first surface 234 is dimensioned to fit into the cutout region 226 of the second anchor plate 214. Accordingly, the length of the second intradiscal insert 218 traverses a substantial portion of the length of the second anchor plate 214. The second generally planar surface 236 is dimensioned to interact with the second generally planar surface 244 of the pivot 238. As such, the second generally planar surface 236 functions to allow rotation of the first anchor plate about the Y-axis, as described above. The second intradiscal insert 218 may also include an aperture 262 located approximately in the center of first surface 234, and spanning the measurable thickness between first surface 234 and second generally planar surface 236, said aperture 262 dimensioned to receive the elongated member 251 of retaining pin 240. The aperture 262 may also be dimensioned to align with central aperture 260 of second anchor plate 214, such that elongated member 251 of retaining pin 240 may traverse the second intradiscal insert 218 and engage with the second anchor plate 212. The second intradiscal insert 218 may also form a protective barrier between the intradiscal element 220 and the second anchor plate 214. This barrier serves to reduce friction between the second anchor plate 214 and intradiscal element 220, ultimately enhancing the durability of the total disc replacement system 210.

The first and second intradiscal inserts 216, 218 may be constructed from any number of materials and/or compositions suitable for medical applications, including but not limited to metallic compositions or alloys (such as Co—Cr—Mo), ceramics (such as zirconia and/or alumina), polymers (such as ultra-high molecular weight polyethylene), and/or any combination thereof. Where beneficial and appropriate, the first and second intradiscal inserts 216, 218 may also be coated with any number of suitable compositions, such as zirconium oxide coating found in U.S. Pat. No. 5,037,438, mentioned above. The first and second intradiscal inserts 216, 218 may be secured to the recessed regions 224, 226 of the first and second anchor plates 212, 214 by any suitable method or material, including but not limited to biocompatible adhesive substances, brazing, and the like.

FIGS. 62-65 illustrate the relative positioning of the pivot 238 and pin 240 when the lateral TDR system 210 of the present invention is in a default position. The head region 250 of retaining pin 240 effectively secures the pivot 238 to the second intradiscal insert 218 (and by extension to second anchor plate 214), due to the differences in radii explained above. This effect can be seen more clearly in FIGS. 68 & 71, where $2d_1$ is smaller than $2d_2$. It is contemplated that the actual difference in radii may be larger, thus creating a greater overlap than that pictured. It is also important to note that in any event, $2d_2$ should not be greater than the difference in radii between the head region 250 and the elongated member 251, such that at least a portion of the head region 250 always overlaps at least a portion of pivot 238.

Figure 66:
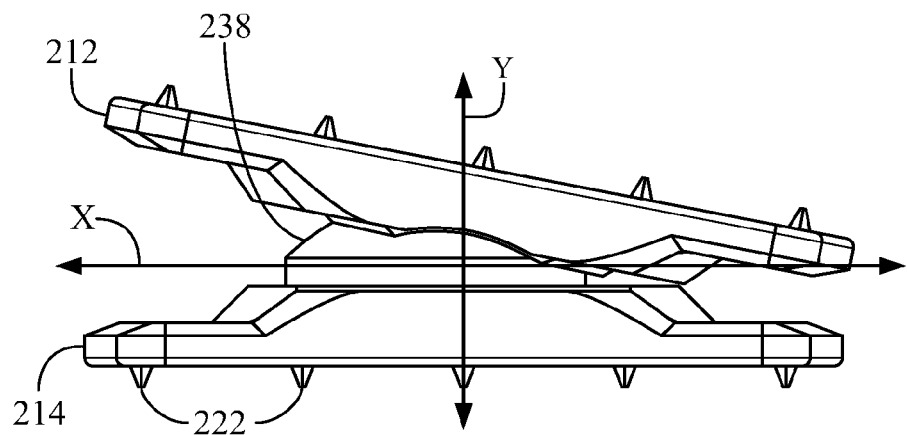
FIG. 66 is a side (anterior or posterior) view of the lateral TDR system of FIG. 48, illustrating rotation about the Z-axis.
Figure 67:
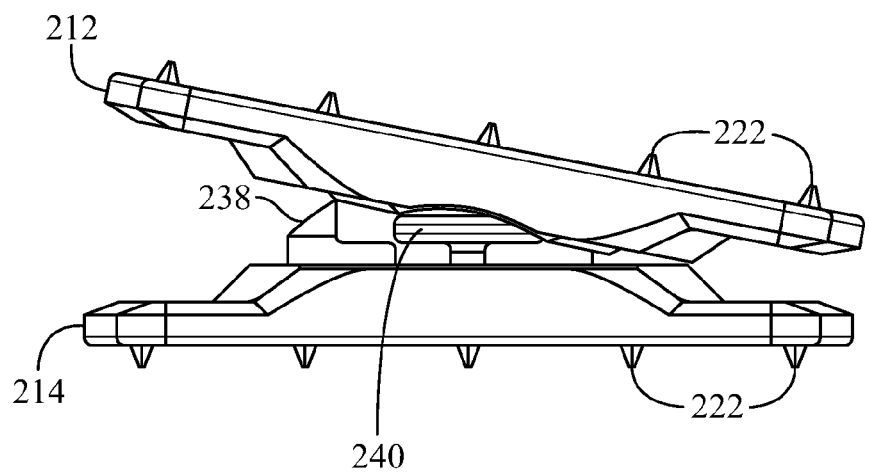
FIG. 67 is a side (anterior or posterior) view of the lateral TDR system of FIG. 66, wherein the intradiscal element has been made transparent to show the relative positioning of the anchor pin.
Figure 69:
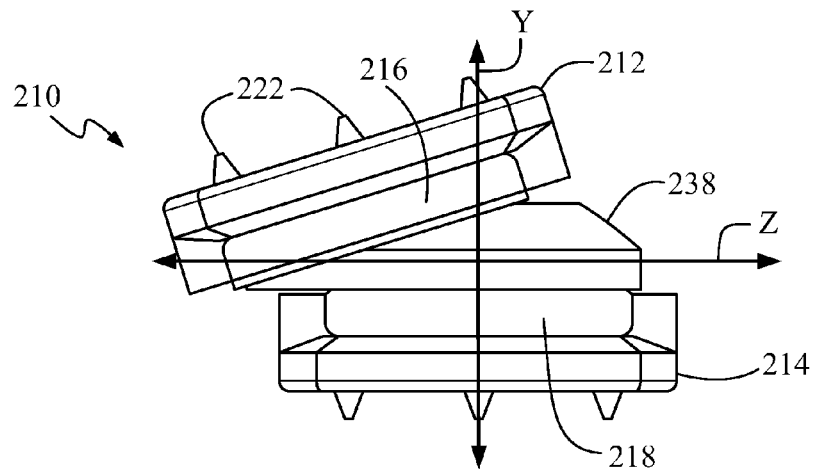
FIG. 69 is an end (lateral) view of the lateral TDR system of FIG. 48, illustrating rotation about the X-axis.
Figure 70:
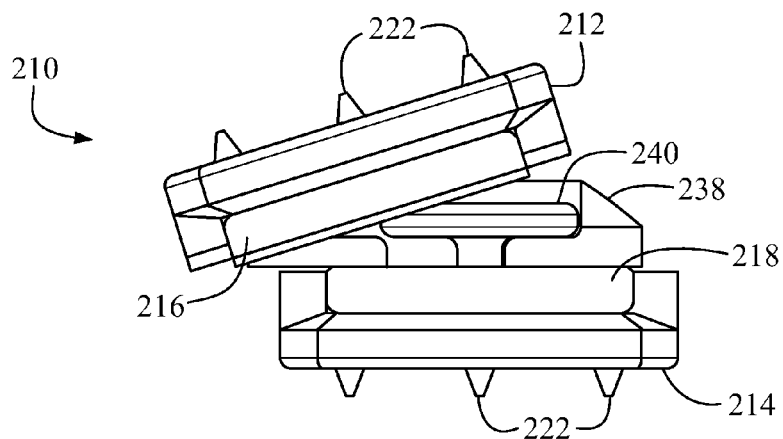
FIG. 70 is an end (lateral) view of the lateral TDR system of FIG. 69, wherein the intradiscal element has been made transparent to show the relative positioning of the anchor pin.

FIGS. 66-68 illustrate the range of motion of the lateral TDR system 210 of the present invention, showing rotation about the Z-axis. FIGS. 69-71 further illustrate the range of motion of the lateral TDR system 210 of the present invention, showing rotation about the X-axis. As explained previously, due to the generally circular shape of the pivot 238 and the interaction between the first articular surface 242 on the pivot 238 and the second articular surface 230 on the first intradiscal insert 216, such rotation may occur about any axis that may be defined by a line in the XZ plane that intersects the Y-axis. The extent of such rotation is limited only by the natural limitations in the human body (muscles, ligaments, spinal structure, etc). Thus, the lateral TDR system 210 of the present invention allows the spine to retain its full range of motion with respect to flexion, extension, and lateral bending. Similarly, rotation about the Y-axis as described above allows for full retention of the spine's axial rotation abilities. Thus, the lateral TDR system 210 of the present invention provides for complete motion retention capabilities of a normal human spine.

The lateral TDR system 210 of the present invention may be provided with varying length, width, and height dimensions depending on the position within the spine of the target intervertebral disc space, as well as individual patient anatomies. By way of example only, the lateral TDR system 210 may be provided having dimensions falling within the ranges of 40-55 mm in length, 18-22 mm in width, and 8-14 mm in height. In a preferred embodiment the lateral TDR system 210 may be provided according to data in Table 1, discussed above in relation to TDR system 10. Furthermore, the lateral TDR system 210 of the present invention may be provided with first and second anchor plates 212, 214 having a shape other than generally rectangular, including by way of example only generally circular and/or generally elliptical. Such alternative shapes may be provided for other surgical techniques (e.g. open procedures) and/or approaches (e.g. anterior, posterior, antero-lateral and postero-lateral).

Figure 72:
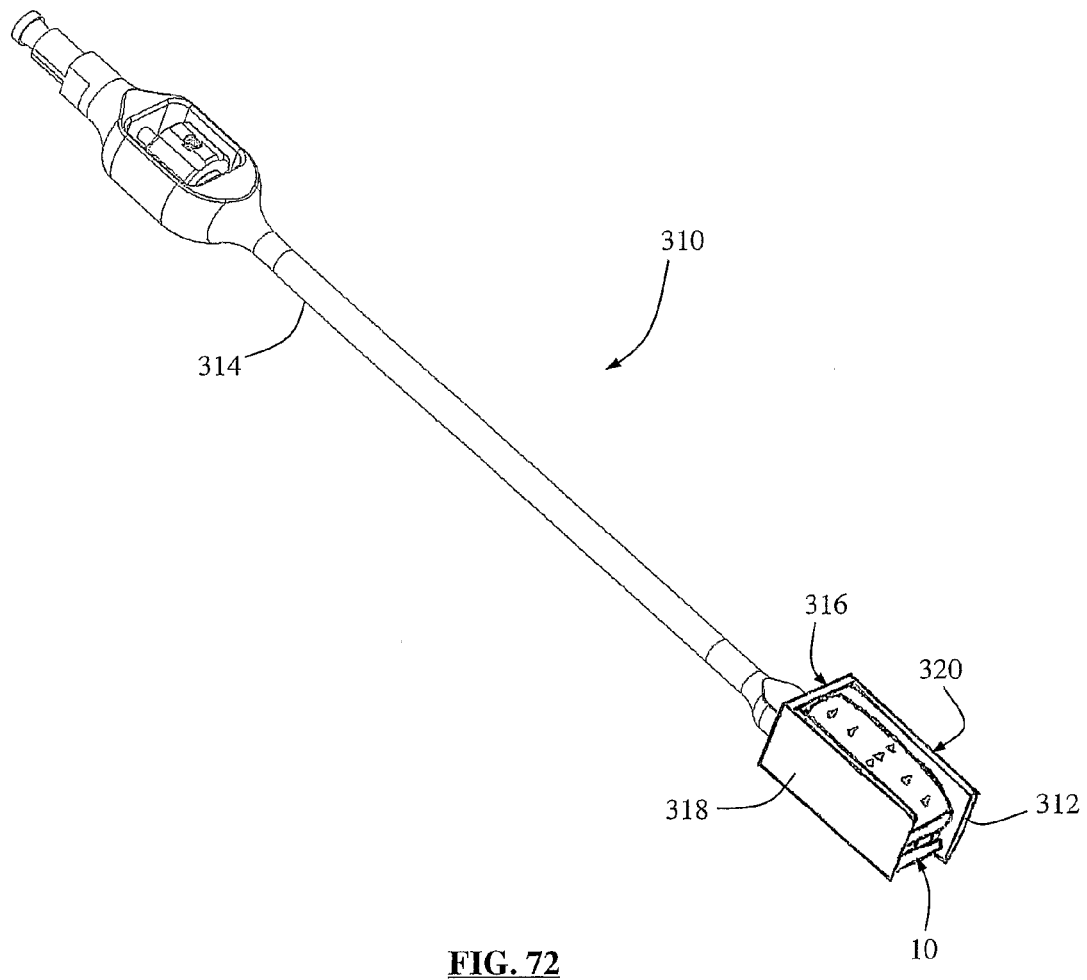
FIG. 72 is a perspective view of an example of an insertion tool according to an alternative embodiment of the present invention coupled to an example of a lateral TDR system according to one embodiment of the present invention.
Figure 76:
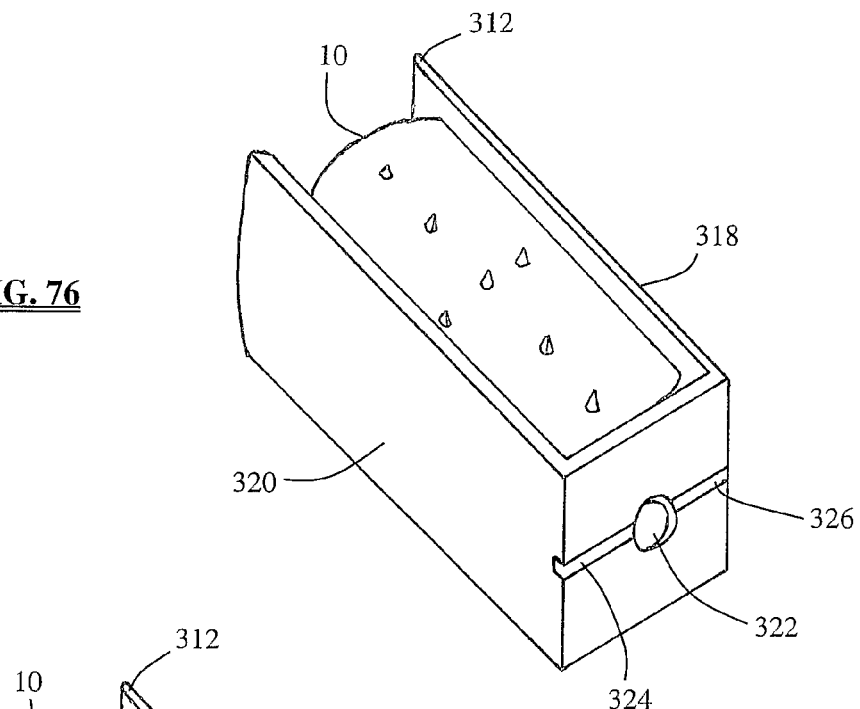
FIG. 76 is a perspective view of a lateral TDR system coupled to the insertion cradle of FIG. 73.
Figure 77:
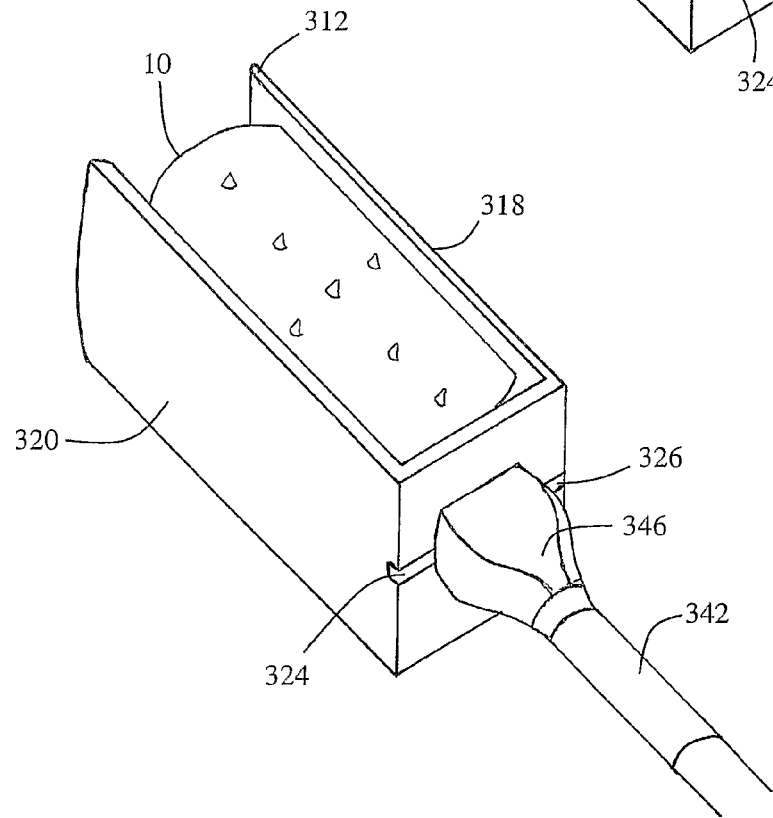
FIG. 77 is a perspective view of the distal region of the insertion tool coupled to the combined insertion cradle and lateral TDR system as shown in FIG. 72.

At times it may be advantageous to be able to insert a lateral TDR system (such as lateral TDR system 200) into an intervertebral space without having to employ a separate distraction tool to keep the adjacent vertebrae far enough apart to allow insertion of the lateral TDR system. FIG. 72 illustrates an example of a self-distracting insertion tool 310 for inserting a lateral TDR system 210 into a prepared intervertebral space according to one embodiment of the present invention. Although shown by way of example only coupled to a TDR system 210 as described above, the insertion tool 310 of the present invention is not limited to interaction with the lateral TDR systems disclosed herein, but rather may be dimensioned to engage any laterally-inserted TDR system, including for example TDR system 10 described above. The insertion tool 310 of the present invention includes an exemplary cradle 312 and an exemplary elongated inserter 314 provided in accordance with a first embodiment of the present invention. Preferably, the cradle 312 is generally rectangular in shape, but may take the form of any geometric shape necessary to interact with the lateral TDR system 210, including but not limited to generally oval, square, and triangular. Preferably, the cradle 312 includes a proximal panel 316 and a pair of opposing side panels 318, 320. The cradle 312 may be composed of any material suitable for facilitating the insertion of a TDR system into an intervertebral space, including but not limited to metal (e.g. titanium), ceramic, and/or polymer compositions. The cradle 312 may engage the lateral TDR system 210 by any suitable means of engagement, including but not limited to a snap-fit engagement, a threaded engagement, hooks, and/or compressive force.

As will be described in detail below, the insertion tool 314 is configured to releasably maintain the exemplary cradle 312 in the proper orientation during lateral insertion into a disc space and thereafter release to deposit the lateral TDR system 210. The lateral TDR system 210, having been deposited in the disc space, facilitates normal spinal functionality over time by maintaining a restored disc height (due to the structural and load-bearing capabilities of the lateral TDR system 210) as well as retaining a normal range of motion.

FIG. 73-76 illustrate, by way of example only, one embodiment of the cradle 312 of the present invention. Cradle 312 is shown as generally rectangular in shape and having a proximal panel 316 and a pair of opposing side panels 318, 320. The cradle 312 may be provided with any number of suitable features for engaging the insertion tool 314 without departing from the scope of the present invention. One engagement mechanism involves providing a threaded receiving aperture 322 in the proximal panel 316 of the cradle 312 of the present invention. The threaded receiving aperture 322 is dimensioned to threadedly receive a threaded connector 360 on the insertion tool 314 (as will be described in greater detail below). The threaded receiving aperture 322 extends inwardly from the proximal panel 316 in a generally perpendicular fashion relative to the proximal panel 316. Although shown as having a generally circular cross-section, it will be appreciated that the receiving aperture 322 may be provided having any number of suitable shapes or cross-sections, including but not limited to rectangular or triangular. In addition to the receiving aperture 322, the cradle 312 is preferably equipped with a pair of grooved purchase regions 324, 326 extending generally horizontally from either side of the receiving aperture 322. The grooved purchase regions 324, 326 are dimensioned to receive corresponding distal engagement members 348, 350 on the insertion tool 314 (as will be described in greater detail below), which collectively provide an enhanced engagement between the cradle 312 and insertion tool 314.

Lateral sides 318, 320 each have an inside surface 328, 330 and an outside surface 332, 334, respectively. Preferably, inside surfaces 328, 330 may be generally planar, but may have any configuration suitable for interaction with TDR system 210, including but not limited to generally planar, generally concave, and generally convex. Outside surfaces 332, 334 may have any configuration suitable for facilitating insertion of a TDR system 210 into a prepared intervertebral disc space, including but not limited to generally planar, generally concave, and generally convex (as shown in the figures by way of example only). Lateral sides 318, 320 each further have a pair of opposing vertical edges 336, 338, and a distal edge 340. Vertical edges 336, 338 and distal edge 340 may have any configuration suitable for facilitating insertion of a TDR system 210 into a prepared intervertebral disc space, including but not limited to generally concave, generally convex, and generally planar (as shown in the figures by way of example only).

The essential functions of the cradle 312 are first to engage the lateral TDR system 210 and second to distract the vertebrae as the lateral TDR system 210 is inserted into the intervertebral space. In order to distract the vertebrae to facilitate insertion of the lateral TDR system 210, the lateral panels 318, 320 must have a height "H" (shown in FIG. 75 as the distance between dashed lines $L_1$ and $L_2$) that is greater than the vertical height "h" of the lateral TDR system 210 as measured by the distance between the tips of opposing anti-migration features 222 (shown in FIG. 75 as the distance between dashed lines $L_3$ and $L_4$).

Figure 78:
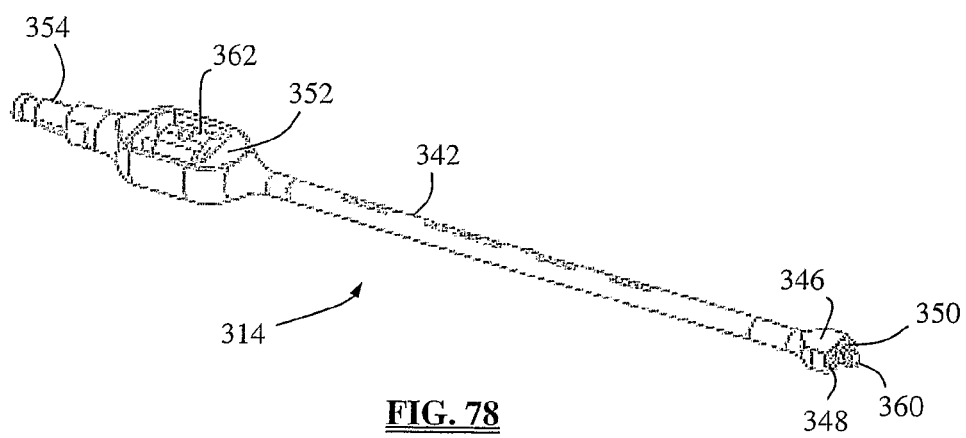
FIG. 78 is a perspective view of an elongated inserter forming part of the insertion tool of FIG. 72.
Figure 79:
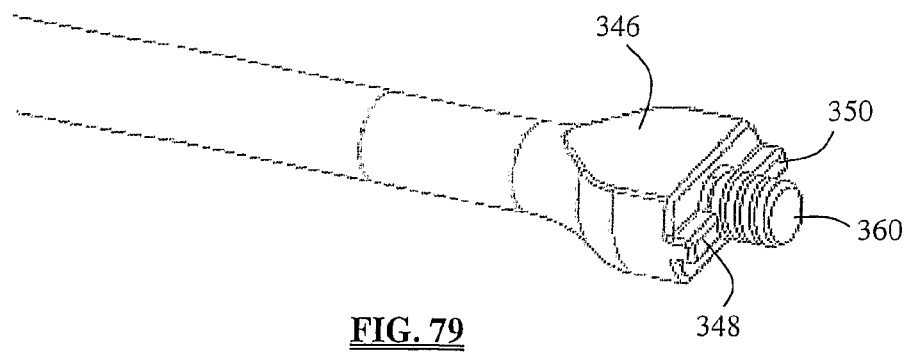
FIG. 79 is an enlarged perspective view of the distal end of the elongated inserter of FIG. 78.
Figure 80:
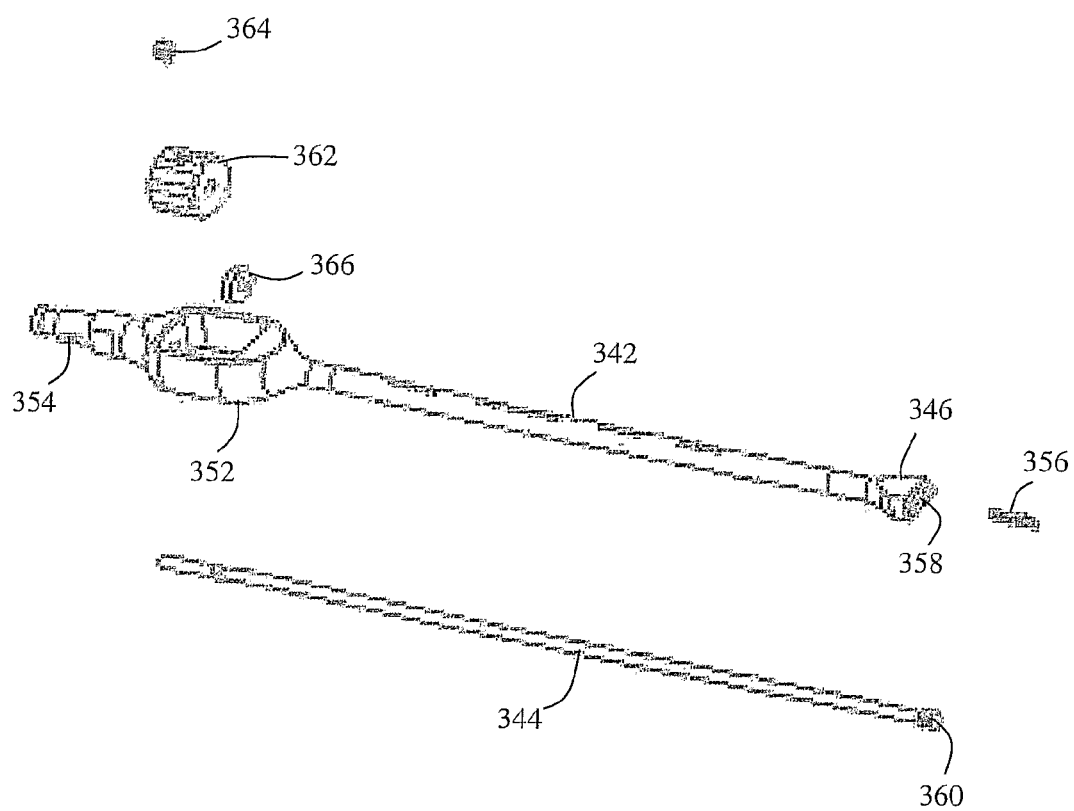
FIG. 80 is an exploded view of the elongated inserter of FIG. 78, illustrating the component parts of the elongated inserter according to one embodiment of the present invention.
Figure 81:
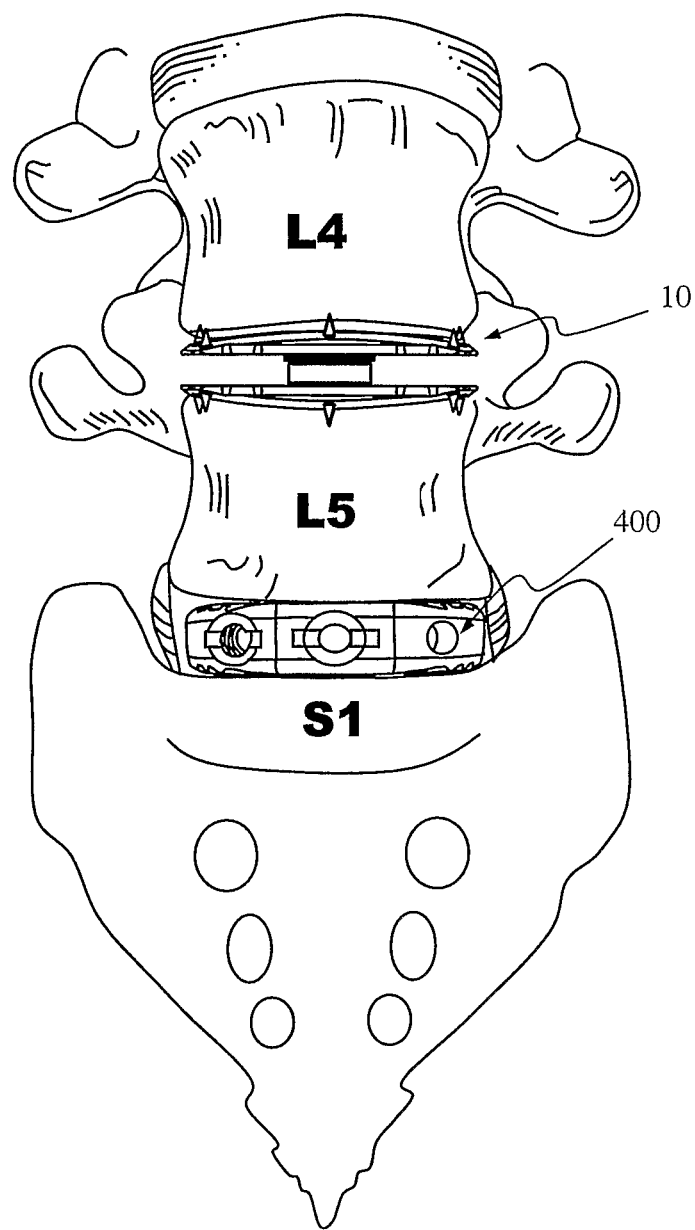
FIGS. 81-82 are anterior and lateral views, respectively, of the lateral TDR system of FIG. 2 in combined use with an anterior lumbar interbody fusion (ALIF) device according to one embodiment of the present invention.
Figure 82:
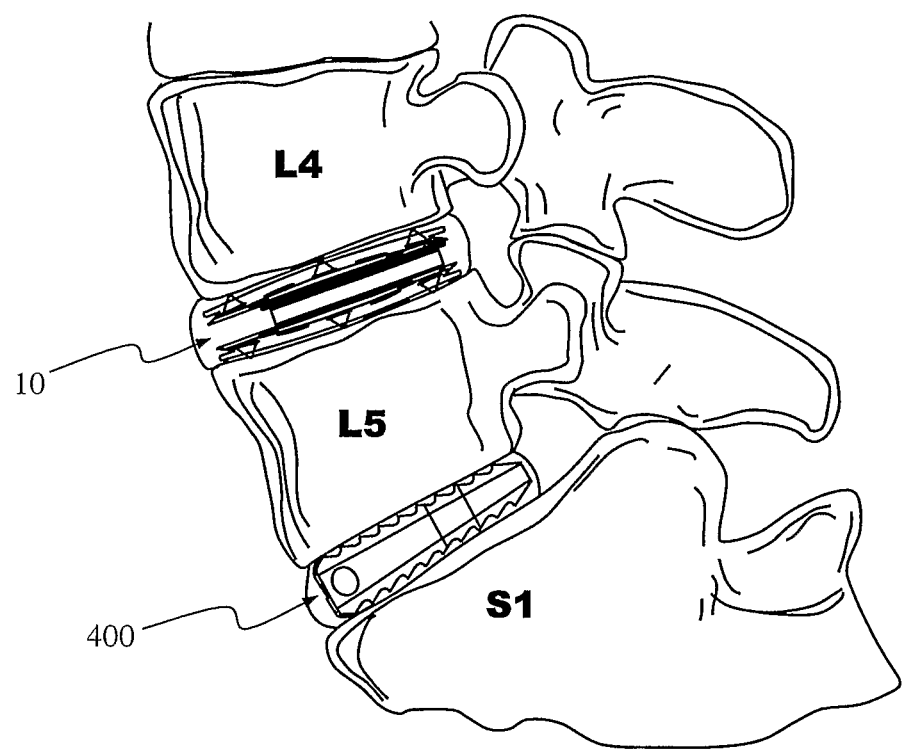

FIGS. 78-80 detail the exemplary elongated inserter 314 according to one embodiment of the present invention. The exemplary elongated inserter 314 includes an elongate tubular element 342 and an inserter shaft 344. The elongate tubular element 342 is constructed with a distal head 346 at its distal end, distal engagement members 348, 350 at its distal end, a thumbwheel housing 352 at its proximal end and a handle 354 at its proximal end. The elongate tubular element 342 is generally cylindrical and of a length sufficient to allow the device to span from the surgical target site to a location sufficiently outside the patient's body so the handle 354 and thumbwheel housing 352 can be easily accessed by a clinician or a complimentary controlling device.

As shown in FIG. 80, the elongate tubular element 342 is dimensioned to receive a spring 356 and the proximal end of the inserter shaft 344 into the inner bore 358 of the elongate tubular element 342. The inserter shaft 344 is dimensioned such that the threaded connector 360 at the distal end of the inserter shaft 344 just protrudes past the distal engagement members 348, 350 to allow engagement with the receiving aperture 322 of the cradle 312. It should be appreciated by one skilled in the art that such a construction allows the inserter shaft 344 to be able to rotate freely within the elongate tubular element 342 while stabilized by a spring 356 to reduce any slidable play in the elongated inserter 314.

The handle 354 is generally disposed at the proximal end of the elongated inserter 314. The handle 354 is fixed to the thumbwheel housing 352 allowing easy handling by the clinician. Because the handle 354 is fixed the clinician has easy access to the thumbwheel 362 and can stably turn the thumbwheel 362 relative to the thumbwheel housing 352. Additionally, the relative orientation of the thumbwheel housing 352 to the handle 354 orients the clinician with respect to the distal head 346 and distal engagement members 348, 350. By way of example only, the thumbwheel housing 352 holds a thumbwheel 362, a setscrew 364, and a spacer 366. The inserter shaft 344 is attached to the thumbwheel 362 and is freely rotatable with low friction due to the spacer 366. One skilled in the art can appreciate myriad methods of assembling a housing similar to the above described.

Figure 41:
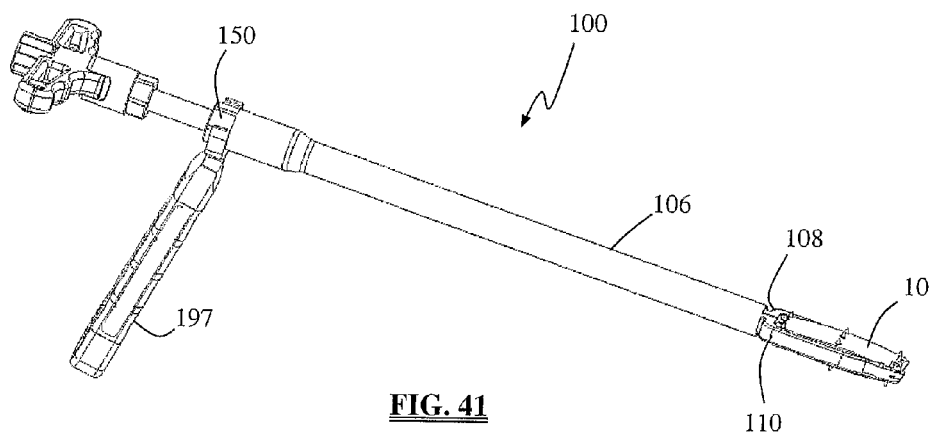
FIGS. 41-44 are perspective views of the lateral TDR system and inserter of FIG. 1, illustrating sequential steps in the use of the inserter and pusher to insert the lateral TDR system of FIG. 1 into an intervertebral space.

FIG. 79 details the distal engagement members 348, 350 of the exemplary elongated inserter 314, and FIG. 41 shows the distal head 346 of the exemplary elongated inserter 314 coupled to the cradle 312 through the purchase regions 324, 326. The distal engagement members 348, 350 are dimensioned fit slidably into the purchase regions 324, 326 with low friction to allow accurate engagement of the threaded connector 360 to the receiving aperture 322 of the cradle 312. In the presented embodiment, the outer dimension of the threaded connector 360 is smaller than the largest outer dimension of the distal head 346 and elongate tubular element 342. Alternatively, other methods of creating a gripping surface are contemplated including but not limited to knurling or facets.

In order to use the system to perform a total disc replacement procedure, the clinician must first designate the appropriate size of TDR system 210. After the cradle 312 is chosen, the distal engagement members 348, 350 and the inserter shaft 344 are inserted into the purchase regions 324, 326 of the cradle 312. At that time the cradle 312 and elongated inserter 314 are slidably engaged with one another. Before the clinician can manipulate the assembled insertion tool 310, the cradle 312 and elongated inserter 314 must be releasably secured together. In order to secure the cradle 312 onto the threaded connector 360 of the elongated inserter 314, the clinician would next employ the thumbwheel 362 to rotate the inserter shaft 344, which in turn rotates the threaded connector 360. The rotation of the threaded connector 360 will releasably engage the receiving aperture 322 of the cradle 312 and stabilize the elongated inserter 314 relative to the cradle 312, thus forming the insertion tool 310. Either at this point or prior to the coupling of cradle 312 and elongated inserter 314, the clinician will engage the cradle 312 to the lateral TDR system 210 by any suitable engagement means provided.

A clinician can utilize the secured system in either an open or minimally invasive lateral total disc replacement procedure. In either type of procedure, a working channel would be created in a patient that reaches the targeted spinal level. After the creation of that channel, the intervertebral space must be prepared. After disc space preparation, the secured device is used to place the lateral TDR system 210 into the prepared intervertebral space. As the cradle 312 (holding the lateral TDR system 210) is inserted into the intervertebral space, the lateral panels 318, 320 force the vertebrae apart, effectuating a self-distraction of the vertebrae. Once the lateral TDR system 210 is inserted into the prepared space, the cradle 312 is released from the elongated inserter 314 by rotating the thumbwheel 362 to disengage the threaded connector 360 from the receiving aperture 322. That motion removes the compressive force on the purchase regions 324, 326 between the distal head 346 and the distal engagement members 348, 350 of cradle 312 and allows the elongated inserter 314 to be slidably removed from the cradle 312. After the threaded connector 360 is disengaged from the cradle 312, the elongated inserter 314 is removed from the working channel. A separate tool (not shown) may then be used to disengage the cradle 312 from the lateral TDR system 210 and remove the cradle 312 from the intervertebral space. As the cradle 312 is removed, the vertebrae will return to their natural position, putting compressive force on the lateral TDR system 210 and ensuring the anti-migration features 222 engage the vertebrae.

The insertion tool 310 of the present invention disclosed herein may be provided with various modifications without departing from the scope of the invention. For example, the engagement mechanism between the cradle 312 and the elongated inserter 314 may be modified from the currently presented treaded interaction. The inserter could be presented in a multiple-pronged orientation, with the prongs engaging corresponding apertures in the cradle. Furthermore, the insertion tool 310 may be equipped with a mechanism to facilitate disengagement of the cradle from the lateral TDR system 210 after insertion into the intervertebral space. This may be the case, by way of example only, if the lateral TDR system 210 is dimensioned to threadedly engage the elongated inserter 312, and the cradle 312 is engaged to the elongated inserter 314 by alternative means.

The lateral TDR system 210 of the present invention disclosed herein may be provided with various modifications without departing from the scope of the invention. For example, the cutout regions 224, 226 of the first and/or second anchor plates 212, 214 may be generally convex or generally concave in addition to the generally planar configuration shown. In similar fashion, the generally arcuate cross-sections of the first articular surface 242 of the pivot 238 of the intradiscal element 220 may be generally concave in addition to the generally convex configuration shown. Moreover, the intradiscal element 220 may be prevented from translating relative to the first and/or second anchor plates 212, 214 in any suitable fashion, such as by equipping the either or both of the anchor plates 212, 214 and/or the intradiscal element 220 with a structure (e.g. a wall member extending from the anchor plate) or by altering the difference in diameters between the head 250 of retaining pin 240 and cutout region 246 of pivot 238, or the difference in diameters between the elongated member 251 or retaining pin 240 and the central aperture 248.

According to a further aspect of the present invention, the lateral TDR systems 10, 200 may be used in conjunction with other spinal implants and/or various surgical procedures, including but not limited to a "hybrid" procedure aimed at fusing at an adjacent vertebral level space to the lateral TDR systems 10, 200 through the use of interbody fusion implants. A multi-level spinal correction often seeks different outcomes for the different spinal levels. For example, the lateral TDR system 10 may be employed through a lateral approach at one level so as to minimize morbidity due to the approach while allowing for motion preservation at that level. It may, however, be difficult to reach the adjacent level through a lateral approach or it may be more advantageous to seek vertebral fusion at the adjacent level. In such a case, the lateral TDR system 10 may be employed for one level while fusion techniques and/or implants are used at the adjacent level. This is illustrated in FIGS. 82-85, wherein a hybrid procedure is performed with motion preservation at the L4-L5 level (i.e. the intervertebral space between the $4^{th}$ and $5^{th}$ lumbar vertebral bodies) and fusion at the L5-S1 level (i.e. the intervertebral space between the 5th lumbar vertebral body and the sacrum). While explained above in this specific example, it should be understood that hybrid lateral motion preservation and fusion according to the present invention may be employed in any group of spinal levels at issue, whether adjacent or several levels apart.

Figure 83:
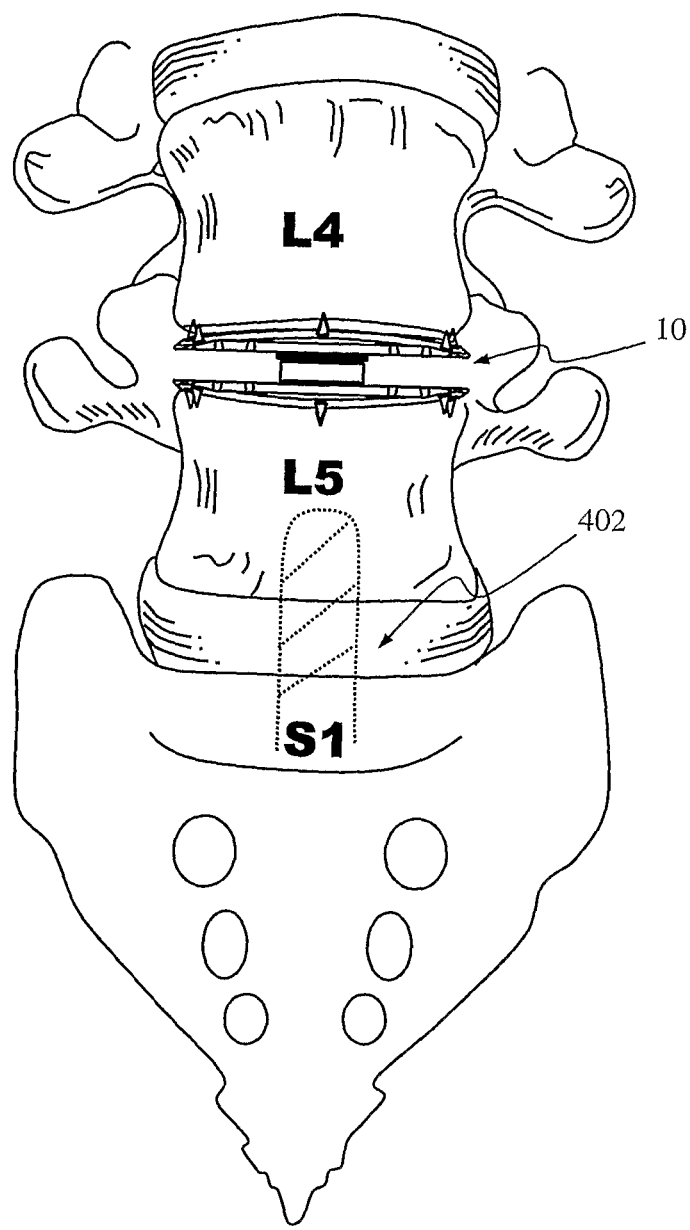
FIGS. 83-84 are anterior and lateral views, respectively, of the lateral TDR system of FIG. 2 in combined use with a trans-sacral interbody fusion device according to one embodiment of the present invention.
Figure 84:
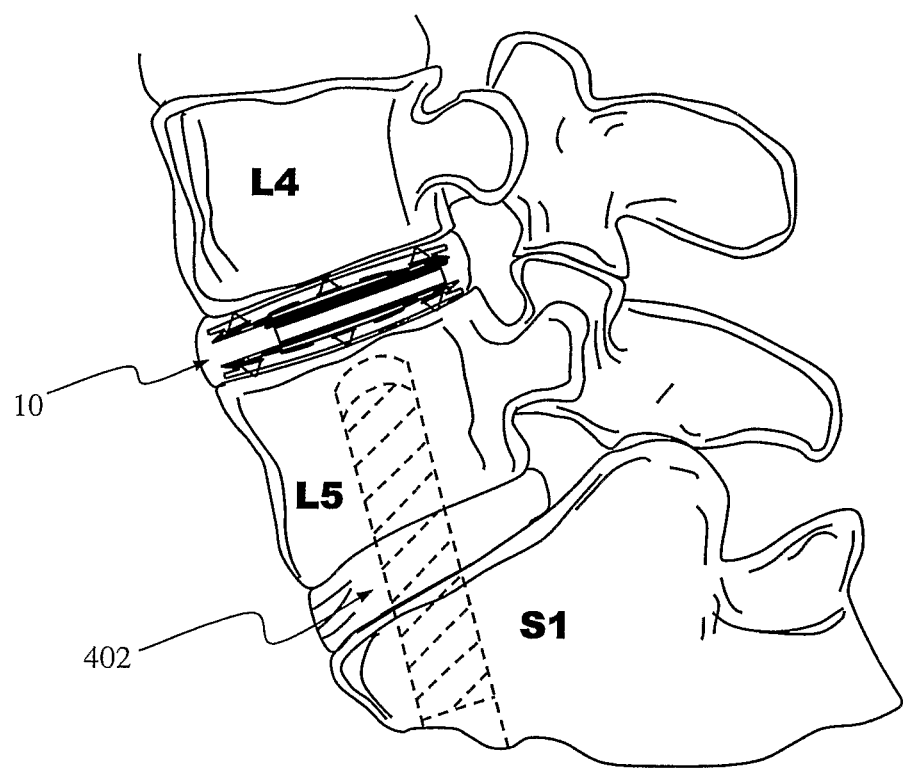

FIGS. 84-85, shown by way of example only, the lateral TDR system 10 in use with an anterior lumbar interbody fusion (ALIF) implant 400 (i.e. fusion via an anterior approach to the spine). TDR system 10 is positioned within the L4-L5 disc space and the ALIF implant 400 is positioned within the L5-S1 disc space. As will be appreciated, the ALIF implant 400 is shown here by way of example only and in practice ALIF implant 400 may take the form of any number of suitable ALIF implants known in the art. Another approach to the L5-S1 disc space is the so-called trans-sacral approach. Using the trans-sacral approach, an implant may be inserted up through the S1 sacral bone and into the L5 vertebra, bridging the L5-S1 disc space and immobilizing S1 and L5 relative to each other. As illustrated in FIGS. 83-84, TDR system 10 may be used advantageously in conjunction (hybrid) with a trans-sacral implant 402. The trans-sacral implant 402 and the method of performing trans-sacral fusion is set forth in detail in U.S. Pat. No. 7,014,633 to Andrew Cragg, the entire content of which is hereby incorporated into this disclosure by reference as if set forth in its entirety herein. While FIGS. 81-84 depict TDR system 10 in use with spinal implants 400, 402, it should be readily understood that these are mere exemplars of the hybrid lateral motion preservation procedure of the present invention. It will also be contemplated that the hybrid technique lateral motion preservation according to the present invention may involve any other surgical procedure in addition to fusion, including but not limited to total disc replacement (other lateral TDR systems of the present invention and/or non-lateral total disc replacement systems), nucleus replacement, using any of a variety of surgical approaches, including but not limited to postero-lateral, anterior, antero-lateral, lateral, and trans-sacral.

The introduction of the total disc replacement system of the present invention via a lateral approach according to the '768 PCT overcomes the drawbacks of the anterior approach total disc replacement systems of the prior art. First, the lateral total disc replacement system of the present invention is easy to accurately place in the anterior-posterior plane, which enhances the performance thereof based on optimal positioning (e.g. with an instantaneous axis of rotation in the posterior region of the disc space). Second, the lateral total disc replacement system of the present invention does not require the removal of the anterior longitudinal ligament (ALL) based on the lateral introduction into the disc space, which maintains the proper structural support of the ALL and thus ensures the sought after motion and stability of the lateral total disc replacement system of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A method for replacing an intervertebral disc comprising the step of:

establishing an operative corridor to an intervertebral disc space via a lateral, trans-psoas surgical approach that leaves the Anterior Longitudinal Ligament (ALL) intact and includes monitoring nerves in the psoas muscle with a neurophysiology based monitoring system to avoid damaging said nerves:

preparing the intervertebral disc space for receipt of a disc replacement implant, the disc replacement implant including a first anchor plate with a first surface for contacting a first vertebra adjacent the disc space and a second interior surface having, an articulation recess integrally formed therein a second anchor plate having a third surface for contacting a second vertebra adjacent the disc space and a fourth interior surface, and an intradiscal element integrally joined with the fourth interior surface, the intradiscal element configured to articulate with the articulation recess, the first anchor plate and second anchor plate together having an implant length defined by a distance along an X-axis, the X-axis being generally parallel to the coronal plane when the implant is positioned within the interbody space, an implant width defined by a distance along a Z-axis, the Z-axis being generally parallel to the sagittal plane when the implant is positioned in the intervertebral space, the implant length being between 40 mm and 55 mm and the implant width being between 18 mm and 22 mm;

simultaneously introducing the first anchor plate and second anchor plate through the lateral trans-psoas operative corridor into the intervertebral disc space such that the intradiscal element of the second anchor plate cooperates within the articulation recess of the first anchor plate to post-operatively allow motion between the first and second vertebrae.

2. The method according to claim 1, wherein said first anchor plate, second anchor plate, and said intradiscal element are formed of one or more of metals, metal alloys, ceramics, and polymers.

3. The method according to claim 2, wherein at least a portion of said first surface of said first anchor plate and at least a portion of said third surface of said second anchor plate is coated with zirconium oxide.

4. The method according to claim 1, wherein said first anchor plate, second anchor plate, and said intradiscal element are formed of the same material.

5. The method according to claim 1, wherein preparing said disc space comprises cutting the annulus of said intervertebral disc at a location contralateral to the operative corridor.

6. The method according to claim 1, comprising the additional step of:

implanting an interbody implant within an additional intervertebral disc space one of adjacent to and remote from said intervertebral disc space and one of before and after introducing said disc replacement implant in said intervertebral disc space.

7. The method according to claim 1, comprising the additional step of:

introducing said disc replacement implant into said intervertebral disc space with an insertion instrument, said insertion instrument being configured to ensure said disc replacement system is inserted in the proper anterior-posterior orientation.

8. The method according to claim 7, wherein said insertion instrument includes indicia on a handle portion that ensures the disc replacement implant is inserted in the proper orientation.

9. The method according to claim 8, wherein said indicia is at least one orientation marker visible to a clinician during insertion.

10. The method according to claim 9, wherein said orientation marker is at least one of a button and an alpha-numeric symbol.

11. The method according to claim 1, wherein said each of said first anchor plate and second anchor plate have a posterior side extending the entire, implant length and parallel to said Z-axis and an anterior side extending the entire implant length and parallel to said Z-axis.

12. The method of claim 1, wherein the implant has a height of between 8 mm and 14 mm.

13. The method of claim 1, wherein the articulation recess is offset posteriorly from a center point of the second interior surface and the intradiscal element is offset posteriorly from a center point of the fourth surface.

14. The method according to claim 13, wherein the disc replacement implant is positioned within the intervertebral disc space with the first anchor plate and second anchor plate, centered along a longitudinal midline of the disc space, such that the intradiscal element is situated posterior to the longitudinal midline.

15. The method according to claim 14, wherein said first anchor plate includes at least one anti-migration feature aligned along the longitudinal midline of said first anchor plate and said second anchor plate includes at least one anti-migration feature aligned along the longitudinal midline of said second anchor plate.

16. The method according to claim 15, comprising the additional step of:
    implanting a radiographic marker in at least one of an upper vertebra and a lower vertebra adjacent to said disc space and in line with said longitudinal midline of said disc space prior to inserting said disc replacement system into said disc space.

17. The method according to claim 15, comprising the additional steps of:
    positioning said at least one anti-migration feature of said first anchor plate and said at least one anti-migration feature of said second anchor plate in line with said radiographic marker prior to and during insertion of said disc replacement system; and
    using at least one of a medical imaging device and visual inspection to check the alignment of said at least one anti-migration feature of said first anchor plate and said at least one anti-migration feature of said second anchor plate with said radiographic marker at least one of during and after insertion.

18. The method according to claim 14, wherein said first anchor plate includes at least one anti-migration feature aligned along the lateral midline of said first anchor plate and said second anchor plate includes at least one anti-migration feature aligned along, the lateral midline of said second anchor plate.

19. The method according to claim 18, comprising the additional steps of:
    positioning said at least one anti-migration feature of said first anchor plate and said at least one anti-migration feature of said second anchor plate in line with the spinous process of at least one of the adjacent vertebrae; and
    using a medical imaging device to check the alignment of said at least one anti-migration feature with said spinous process at least one of during and after insertion.

20. The method of claim 14, wherein at least one of said first anchor plate and said second anchor plate has an angled cross-section to force the adjacent vertebral bodies into lordosis when the total disc replacement is introduced into a lumbar spine.

21. The method of claim 20, wherein the first and second anchor plate have a combined angle of between 1 and 15 degrees.

22. The method of claim 21, wherein the first and second anchor plate have a combined angle of between 5 degrees.

23. The method of claim 1, wherein the implant is positioned within the disc space such that the implant extends form the apophyseal ring at a first lateral aspect of the intervertabral disc space to the apophyseal ring at a second lateral aspect of the intervertebral disc space.

\* \* \* \* \*